(12) United States Patent
Bzik et al.

(10) Patent No.: US 7,803,389 B2
(45) Date of Patent: Sep. 28, 2010

(54) TOXOPLASMA GONDII MUTANT WITH ENHANCED HOMOLOGOUS RECOMBINATION AND USES THEREOF

(75) Inventors: David J. Bzik, Grantham, NH (US); Barbara A. Fox, Grantham, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 12/394,365

(22) Filed: Feb. 27, 2009

(65) Prior Publication Data

US 2009/0181056 A1 Jul. 16, 2009

Related U.S. Application Data

(63) Continuation-in-part of application No. PCT/US2008/081274, filed on Oct. 27, 2008.

(60) Provisional application No. 60/983,339, filed on Oct. 29, 2007, provisional application No. 61/057,972, filed on Jun. 2, 2008.

(51) Int. Cl.
  A61K 39/012 (2006.01)
  A61K 39/38 (2006.01)
  C12P 1/00 (2006.01)
  C12N 15/00 (2006.01)

(52) U.S. Cl. .................. 424/273.1; 424/184.1; 435/41; 435/440

(58) Field of Classification Search ........................ None
See application file for complete search history.

(56) References Cited

U.S. PATENT DOCUMENTS

2005/0287648 A1    12/2005   Smith et al. ............... 435/91.1

OTHER PUBLICATIONS

Kleppe et al (Tidsskr Nor Laegeforen, Sep. 30, 2001; 121(23):2717-20)(Abstract only).*
Hoppner (Horm Re. 2002, 58 Suppl. 3:7-15) (Abstract only).*
Gottstein (Schweiz Med Wochenschr Suppl. 1995; 65:89S-95S)(Abstract only).*
Waldeland et al (Journal of Parasitology, Feb. 1983; 69(1):60-5)(Abstract only).*
The Institute for Genomic Research Accession No. 583.m05492.
Aravind et al., "Prokaryotic homologs of the eukaryotic DNA-end-binding protein Ku, novel domains in the Ku protein and prediction of a prokaryotic double-strand break repair system", Genome Research 2001 11:1365-1374.
Baumann et al., "Protection of telomeres by the Ku protein in fission yeast", Molecular Biology of the Cell 2000 11:3265-3275.
Doherty et al., "Identification of bacterial homologues of the Ku DNA repair proteins", FEBS Letters 2001 500:186-188.
Featherstone et al., "Ku, a DNA repair protein with multiple cellular functions?", Mutation Research 1999 434:3-15.
Fox et al., "De novo pyrimidine biosynthesis is required for virulence of *Toxoplasma gondii*", Nature 2002 415:926-929.
Hopfner et al., "DNA double-strand break repair from head to tail", Current Opinion in Structural Biology 2002 12:115-122.
Ninomiya et al., "Highly efficient gene replacements in *Neurospora* strains deficient for nonhomologous end-joining", Proc. Natl. Acad. Sci. USA 2004 101(33):12248-12253.
Sandoval et al., "High G/C content of cohesive overhangs renders DNA end joining Ku-independent", DNA Repair 2004 3:13-21.
Walker et al., "Structure of the Ku heterodimer bound to DNA and its implications for double-strand break repair", Nature 2001 412:607-614.
Yoo et al., "Characterization of the RNA binding properties of Ku protein", Biochemistry 1998 37:1336-1343.
Burton et al. "Ku Heterodimer-Independent End Joining in *Trypanosoma brucei* Cell Extracts Relies upon Sequence Microhomology" Eukaryotic Cell 2007 6(10):1773-1781.

* cited by examiner

*Primary Examiner*—Vanessa L. Ford
(74) *Attorney, Agent, or Firm*—Licata & Tyrrell P.C.

(57) ABSTRACT

The present invention relates to a mutant *Toxoplasma gondii* which exhibits enhanced homologous recombination. The mutant of the present invention is a knockout in the KU80-dependent nonhomologous end-joining pathway which finds application in generating *T. gondii* gene knockouts and gene replacements for use in vaccine and drug development.

15 Claims, 17 Drawing Sheets

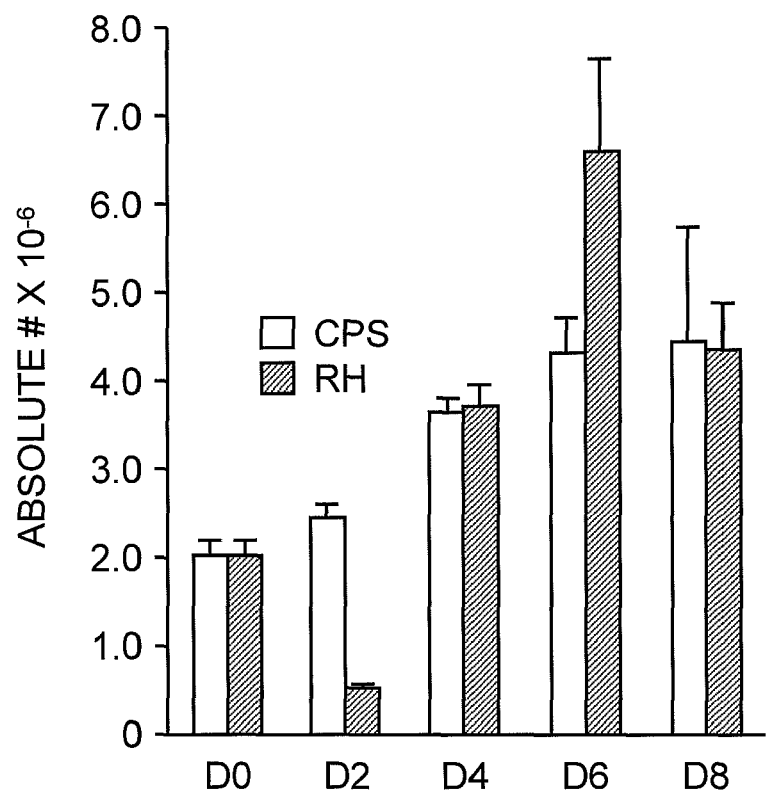
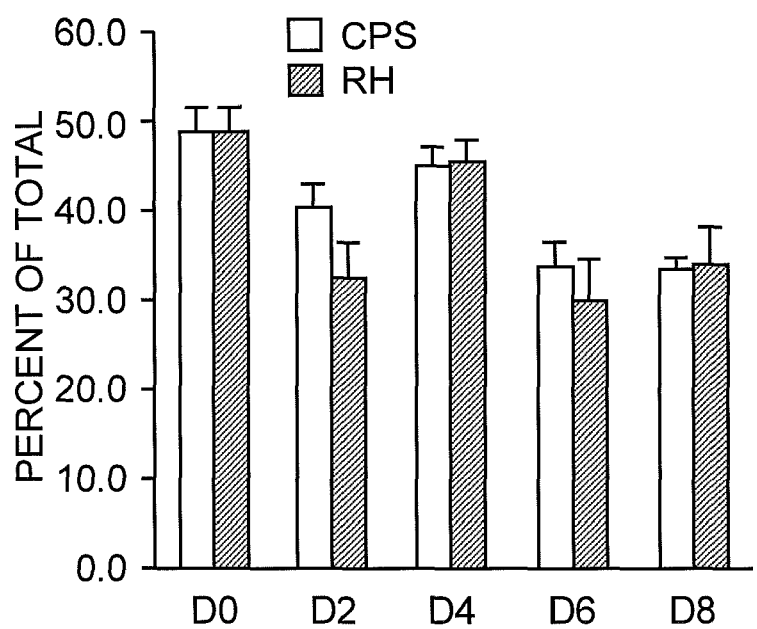
FIG. 3C

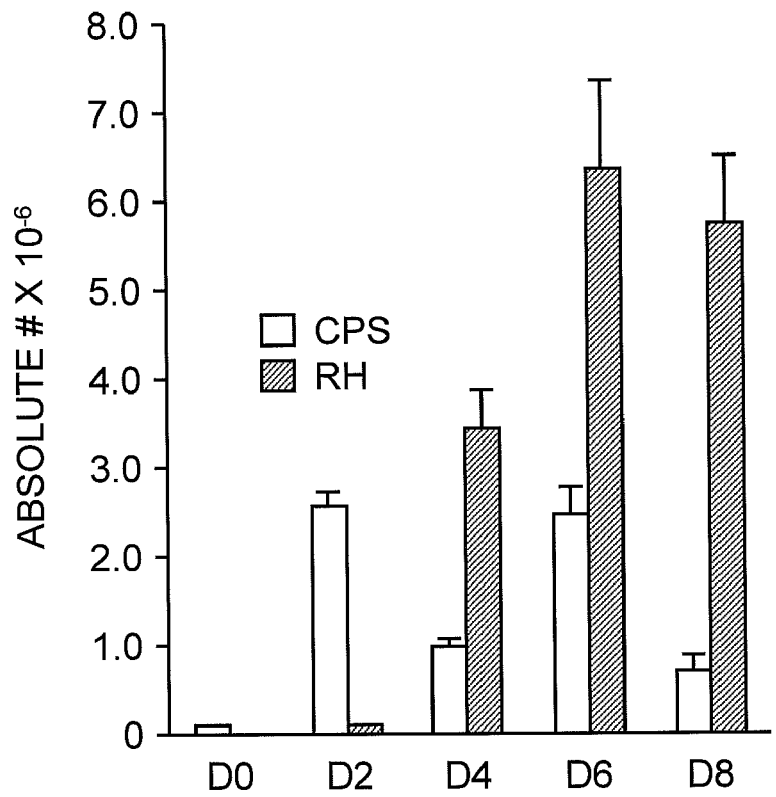
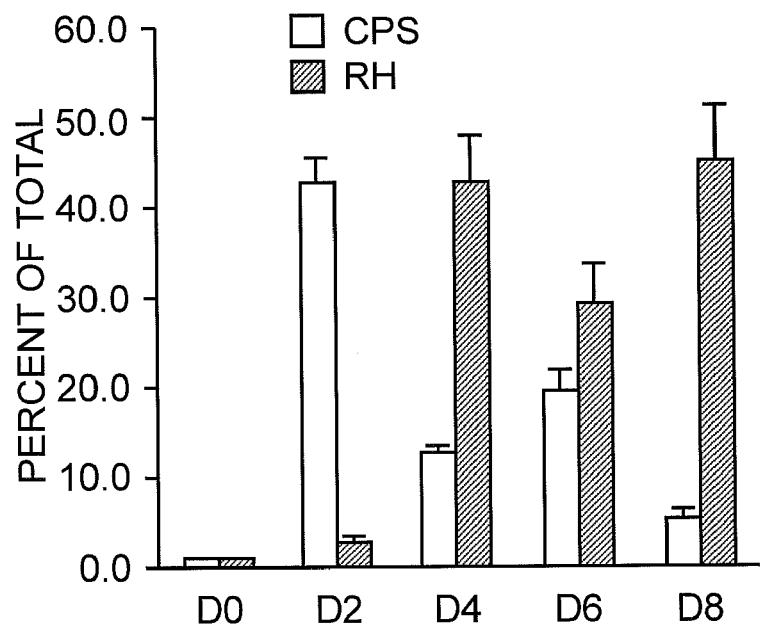
FIG. 3D

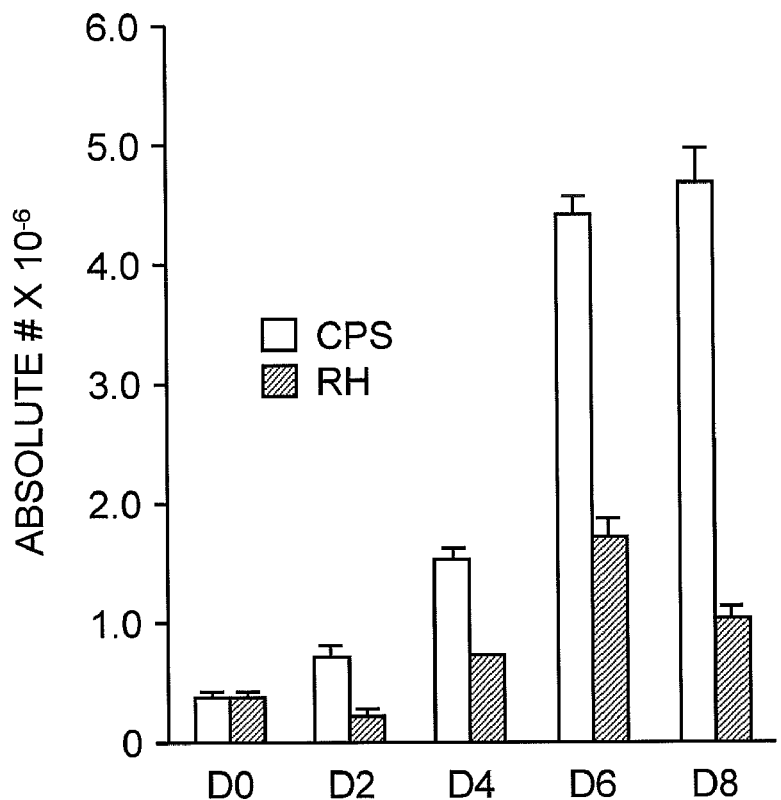
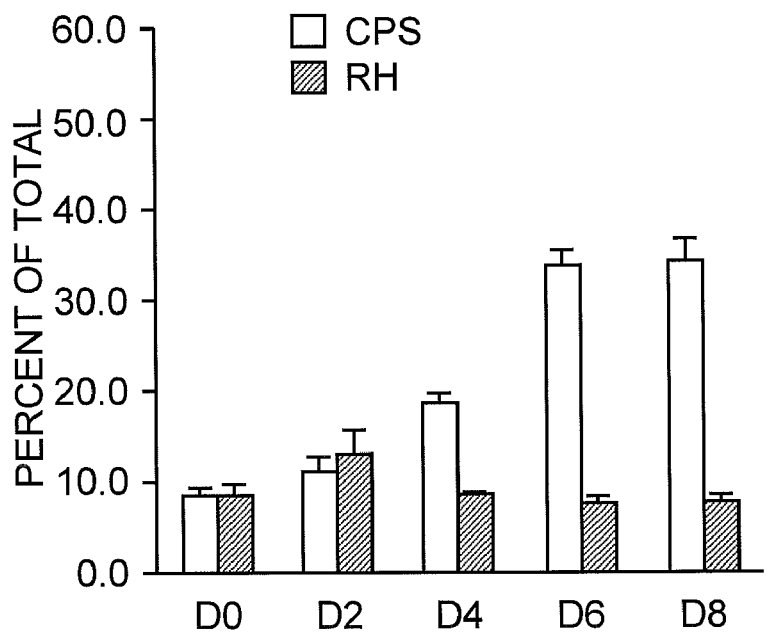
FIG. 3F

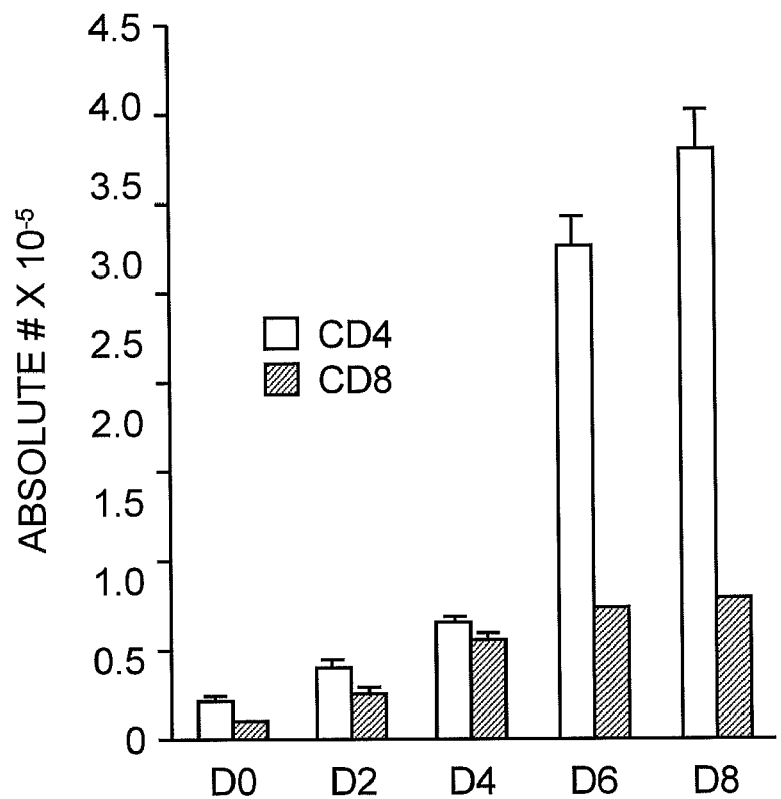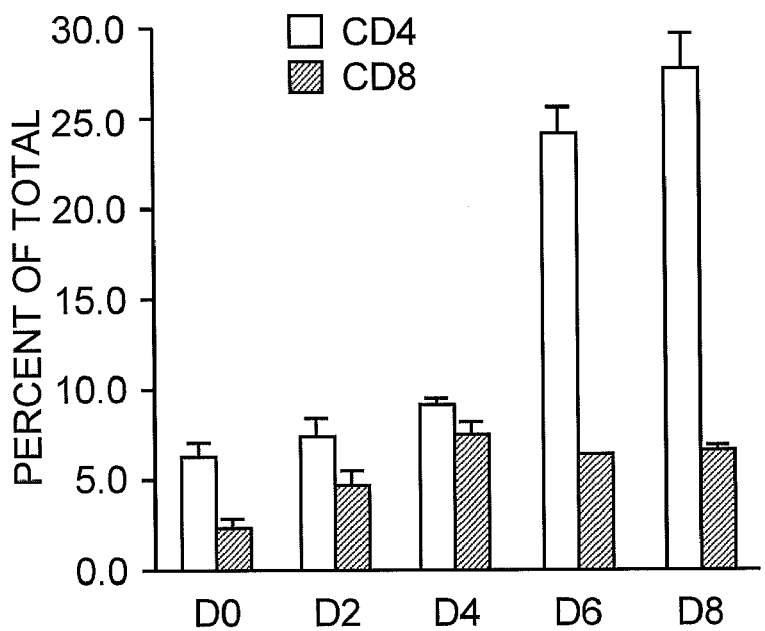
FIG. 3G

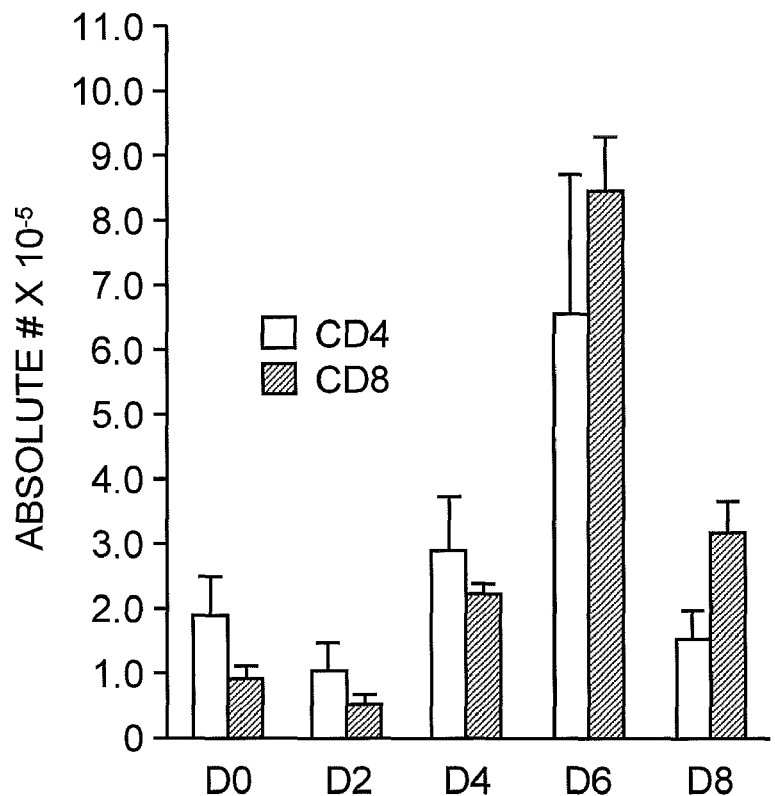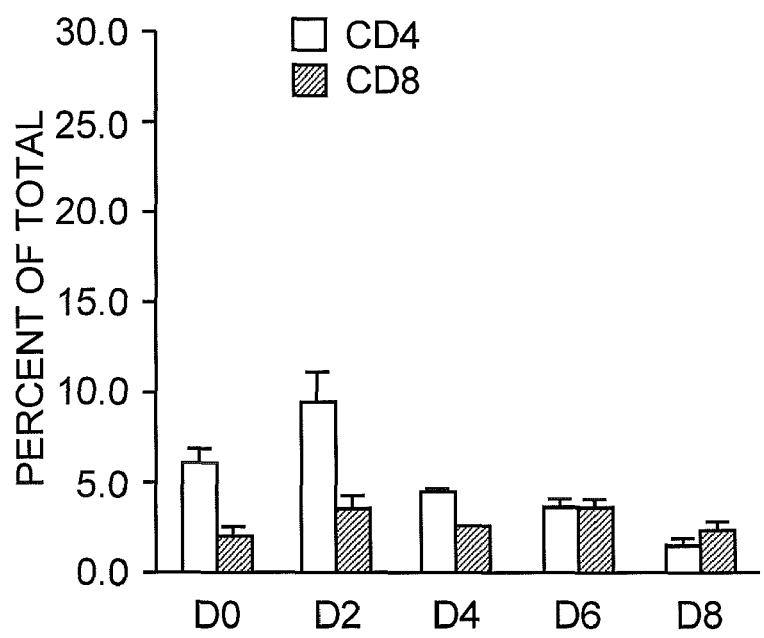
FIG. 3H

| | | | |
|---|---|---|---|
| Tg | 1 | MALPGQSFKRVIVLLLDCGATMQQTLRGDFS-DALVAQTEALSSSFASSGGASSPSPLSKKADSTPSQVPLSPDSVPSISAADRSADLSS | 89 |
| At | 1 | MARN----REGLVLVLDVGPAMRSVLPDVEKACSMLLQKKLIYNKYDEVG----IVVFGTEETGNELAREIGGYENVTVLRNIRVVDELA | 82 |
| Tg | 90 | FHAMKRAARAYVQ--RLAATSAKVDVGVVCEGSCRTDNP-LAPVEGDIQPGDTGDAEEGYKHVEVSLRPESASWKLVQELEKVKNSANRS | 176 |
| At | 83 | AEHVKQLPRGTVAGDFLDALIVGMDMLIKMYGNAHKGKKRMCLITNAACP--TKDPFEGTKDDQVST----IAMKMAAEGIKMESIVMRS | 166 |
| Tg | 177 | DAIDGLVVAVDMVEKTYGPKLSQNNVSFLVFSDCQSSPATPEDIPAVRDRLEVLGIRVHFIIVDGSVPTHPGIWRPGDAFGAEKTRNDQG | 266 |
| At | 167 | ----------NLSGDAHERVIEENDHLLTLFSSNAIAKTVNVDSPLS--------------LLGSLKTRR--VAPVTLFRGDLEIN--- | 226 |
| Tg | 267 | EHDEDWRDLKVERFYFRANDPERTPVKLGEPDTRQDGTSIFGRPDGSSEDE-RAPGAGGDAGVHIQRLYAYRYGKQLVAVSGVEQQAFK | 355 |
| At | 227 | --------PTMKIKVWVYKKVAEERLPTLKMYSDKAP--PTDKFAKHEVKVDYDYKVTAESTEVIAPEERIKGFRYGPQVIPISPDQIETLK | 308 |
| Tg | 356 | QQTTAGLVVLGVTRRDSIQRWWNLGPPEYYTCALNNRPSLVALRSLVLALQRLDSVLLCSFVWRGGYPAKLVALLPHVGGNREKRKAWQ | 445 |
| At | 309 | FKTDKGMKLLGFTEASNILRHYYMKDVNIVVPDPSKEKSVLAVSAIAREMKETNKVAIVRCVWRNGQGNVVVGVLTPN--------- | 386 |
| Tg | 446 | ATASLKESDDVKREEETNQKEAGDEDKTYGLHLIYLPVAEDMLELRLPSLPSVTPRQLRAVETIVESLTLPGSPQVSVKSGEKGGRASEK | 535 |
| At | 387 | -----VSERD------------------DTPDSFYFNVLPFAEDVREFPFPSFN-------------------------KLPSS---- | 422 |
| Tg | 536 | DEGDREAEKKPIDGEWEEVEAQRKALQAPASSPAGWQTNAPLEIAVDPSTRVHSPSPPCSSAAFPSFLPDSISSFATKSESLSLHKIHNP | 625 |
| At | 423 | -------------------WKPDEQQ------------------------QAVADNLVKMIDLAP----------SAEEVLKPDLTPNP | 459 |
| Tg | 626 | TLQRYYQLIVYR-HYNPASPPVALGEEGSETQAQTTWREAEESHQHRLHHMWARGSPVERLFTVRTPGCLDSEQPDASVEQTKEAGQRET | 714 |
| At | 460 | VLQRFYEYLELKSKSTDATLPPMDG-------TEFKRLMEQDPELSSNNKSIMDTFRGS------FEVK-------KLKKASKR---- | 525 |
| Tg | 715 | QVDAALKAAFPQATSLEAQTAGRRQREVQQKLLFGEVVRKQKELVVRDVKVSGEWTEPHFDTP-GEEPRMTAEARREETEKLERAIEEEE | 803 |
| At | 526 | -----LLR-----------------------------------------------------DKPSGSD----------DEDNRMITYDA | 546 |
| Tg | 804 | RQKKLEALKALHVHSVNPVRDFQRLLEVK-ETDLTEKAIQEMTEMIFKFLRAAGPPQGALERPTGAGRGGETSGLQNFRRQQHLGKALVC | 892 |
| At | 547 | KEN-----KIDIVGDANPIQDFEAMISRRDKTDWTEKAITQMKNLIMKLVENCTDE-------------------GD---------KALEC | 604 |
| Tg | 893 | VEALREGCRRELEGEKFNEFLAEVKAEQCRADAAADDSFRTFWNLLKSRKIGLITHAEDPRVDLEPAQSLRIYEDESVQELSTQTAMTAA | 982 |
| At | 605 | VLALRKGCVLEQEPKQFNEFLNHLFKLCQ------ERNLSHLLEHFMSKKITLIPKSE------AADSDIVDENAGDFIVKQESMLES | 680 |
| Tg | 983 | RPLDPHDVDDLLDLVE | 998 (SEQ ID NO:2) |
| At | 681 | | 680 (SEQ ID NO:3) |

FIG. 6

TOXOPLASMA GONDII MUTANT WITH ENHANCED HOMOLOGOUS RECOMBINATION AND USES THEREOF

INTRODUCTION

This application is a continuation-in-part application of PCT/US2008/081274, filed Oct. 27, 2008, which claims benefit of priority to U.S. Provisional Application Ser. Nos. 60/983,339, filed Oct. 29, 2007, and 61/057,972, filed Jun. 2, 2008, the contents of which are incorporated herein by reference in their entireties.

This invention was made with government support under Grant Nos. 1R21AI073142 and AI41930 awarded by the National Institutes of Health. The government has certain rights in the invention.

BACKGROUND OF THE INVENTION

*Toxoplasma gondii* is an obligate intracellular parasite capable of infecting most warm-blooded vertebrates and many nucleated cell types. Parasite transmission occurs orally through ingestion of tissue cysts or sporozoites from feline feces in contaminated soil, food, and water. Infection typically results in an asymptomatic primary infection that leads to a chronic latent infection affecting 30% of the world's population (Carruthers (2002) *Acta Trop.* 81:111-122). Following oral ingestion of tissue or oocyst cysts, parasites are released into the gut mucosa where they infect host cells and transform into the rapidly replicating tachyzoite stage. Rapidly replicating tachyzoites disseminate widely throughout the host reaching most organs and the brain. Host immune pressure is thought to trigger differentiation of tachyzoites into slow growing bradyzoites and development of tissue cysts. Despite the potent Th-1 acquired immunity that is elicited by primary infection, tissue cysts persist in immune privileged sites such as the brain for the life of the host. The reactivation of bradyzoites to tachyzoite differentiation in brain cysts leads to recrudescent and life threatening Toxoplasmic encephalitis in AIDS patients (Luft and Remington (1992) *Clin. Infect. Dis.* 15:211-222). *T. gondii* primary infections in pregnancy also lead to spontaneous abortion or severe CNS damage in neonates. As *T. gondii* is the 3$^{rd}$ leading cause of food-born illness in the U.S., it is a significant human pathogen and therefore understanding the mechanisms underlying the development of protective immunity in response to infection is of high importance to development of vaccines.

*T. gondii* is now a widely recognized model for host response mechanisms. During active infection, *T. gondii* induces a potent systemic Th-1 inflammatory response that results in life long CD8$^+$ T cell-mediated immune control of the infection. Infection triggers the innate response through a MyD88-dependent pathway resulting in IL-12-independent production of IFN-γ by NK and T cells leading to the recruitment of neutrophils and macrophages to the site of infection (Scanga, et al. (2002) *J. Immunol.* 168:5997-6001; Mun, et al. (2003) *Int. Immunol.* 15:1081-1087; Scharton-Kersten, et al. (1996) *Exp. Parasitol.* 84:102-114). Concomitant with the innate response, the development of the acquired Th-1 response is driven by secretion of IL-12 from neutrophils, macrophages and DCs that increases inflammatory cell infiltration, activates APCs and enhances production of IFN-γ by T cells and NK cells leading to the cell-mediated immune control (Bennouna, et al. (2003) *J. Immunol.* 171:6052-6058; Gazzinelli, et al. (1994) *J. Immunol.* 153:2533-2543).

Certain mechanisms of the immune response and key mediators of host immune control have been defined. Previous studies of host responses have typically used replicating and infectious strains of *T. gondii* that widely disseminate and cause extensive host tissue destruction and associated host-derived inflammatory responses. Other immune response models are based on studies using whole parasite antigen or parasite components (Scanga, et al. (2002) supra; Mun, et al. (2003) supra; Scharton-Kersten, et al. (1996) supra; Bennouna, et al. (2003) supra; Gazzinelli, et al. (1994) supra; Aliberti, et al. (2000) *Nat. Immunol.* 1:83-87). These host response and vaccine models reveal that immunization with weakened, but living and invasive *T. gondii* parasites results in complete protection against lethal challenge infections (Waldeland and Frenkel (1983) *J. Parasitol.* 69:60-65; Snzuki and Remington (1988) *J. Immunol.* 140:3943-3946; Bourguin, et al. (1998) *Infect. Immun.* 66:4867-4874; Kasper, et al. (1985) *J. Immunol.* 134:3426-3431).

SUMMARY OF THE INVENTION

The present invention features a mutant *Toxoplasma gondii* that exhibits enhanced homologous recombination resulting from mutation of a locus encoding a protein of the KU80-dependent nonhomologous end-joining pathway. In particular embodiments, the protein of the KU80-dependent nonhomologous end-joining pathway is KU80, KU70, or DNA ligase IV. In one embodiment, the mutation is a deletion, substitution or insertion. In another embodiment, mutation deletes all, or a substantial portion, of the coding region and/or promoter of the locus. In a further embodiment, the mutation involves replacing the coding region and/or promoter of the locus with a nucleic acid molecule encoding a selectable marker. Selectable markers of use in the present invention include hypoxanthine-xanthine-guanine phosphoribosyltransferase, thymidine kinase, hygromycin resistance, cytosine deaminase, dihydrofolate reductase, bleomycin, chloramphenicol acetyl transferase, or a combination thereof.

As an alternative to use of a selectable marker, the coding region and/or promoter of the locus can be replaced with one or more nucleic acid molecules encoding exogenous proteins. Exogenous proteins of use in this embodiment include non-*Toxoplasma gondii* antigens or proteins that produce a non-*Toxoplasma gondii* antigen (e.g., lipid or polysaccharide) from bacteria, viruses, fungi, parasites or tumors; as well as therapeutic antibodies, proteins, enzymes or peptides; and human therapeutic target proteins or enzymes.

A particular feature of the present invention is an attenuated *T. gondii* strain. Such attenuation can be achieved by pyrimidine auxotrophy created by, e.g., mutation of one or more proteins involved in pyrimidine synthesis or pyrimidine salvage. Such proteins include pyrimidine auxotrophy comprises mutation of carbamoyl phosphate synthetase II, aspartate transcarbamylase, dihydroorotase, dihydroorotase dehydrogenase, orotate phosphoribosyltransferase, orotidine 5'-monophosphate decarboxylase, uridine phosphorylase, uracil phosphoribosyltransferase, and/or a nucleobase/nucleoside transporter of pyrimidine bases or nucleosides. Attenuated *T. gondii* of this invention find use in vaccines formulated for intraperitoneal, intranasal or intravenous administration for generating an immune response in an animal to *Toxoplasma gondii* and/or non-*T. gondii* antigens.

Methods for generating one or more gene knockouts or gene replacements in *Toxoplasma gondii* and live, whole-cell screening assays are also provided.

BRIEF DESCRIPTION OF THE DRAWINGS

FIG. 1 shows the percent survival of mice immunized with cps1-1 knock-out via different routes of administration. In FIGS. 1B and 1C, statistical significance was calculated using Kaplan-Meier product limit test.

FIG. 3 shows peritoneal excaudate inflammatory cell recruitment in response to infection with cps1-1 knock-out as compared to highly virulent strain RH. C57Bl/6 mice were infected i.p. with $1 \times 10^6$ cps1-1 knock-out or $1 \times 10^3$ RH parasites and total PECs were harvested at Days 0, 2, 4, 6, and 8. FIGS. 3B-3F respectively show numbers of granulocytes (GR-1$^+$ CD68$^+$ in R3), macrophages (CD68$^+$), inflammatory macrophages (GR-1$^+$ CD68$^+$), and B lymphocytes (CD19$^+$), and T lymphocytes (CD3$^+$) upon cps1-1 vaccination and RH infection, whereas FIGS. 3G and 3H show CD3$^+$ CD4$^+$ and CD3$^+$ CD8$^+$ T lymphocyte numbers upon cps1-1 vaccination (FIG. 3G) or RH infection (FIG. 3H). The data are mean absolute numbers (upper panel) or percentages of total events recorded (lower panel) and are representative of two experiments that had similar outcomes. P values are based on unpaired two tailed Students T test.

FIG. 4 shows systemic Th-1 cytokine production in response to infection with cps1-1 or RH. C57Bl/6 mice were infected i.p. with $1 \times 10^6$ cps1-1 or $1 \times 10^3$ RH parasites and sera were taken at Days 0, 2, 4, 6, and 8. Serum levels of cps1-1- and RH-induced production of IFN-γ (FIG. 4A), IL-12p40 (FIG. 4B), and IL-12p70 (FIG. 4C) were measured by ELISA. The data presented are representative of three experiments with similar results and indicate the mean±SEM. P values are based on unpaired two tailed Students t-test and are as follows.

FIG. 5 shows PEC and splenocyte Th-1 cytokine production in response to infection with cps1-1 or RH. C57Bl/6 mice were infected i.p. with $10^6$ cps1-1 or $10^3$ RH and whole PECs or splenocytes were harvested at Day 0, 2, 4, 6, and 8. PECs (FIGS. 5A-5C) were plated at $1 \times 10^6$ cells/ml and splenocytes (FIGS. 5D-5F) were plated at $5 \times 10^6$ cells/ml. All cells were cultured for 24 hours. Supernatants were then assayed for IFN-γ (FIGS. 5A and 5D), IL-12p40 FIGS. 5B and 5E), and Il-12p70 (FIGS. 5C and 5F) by ELISA. Day 0 controls represent control injection of PBS i.p. All experiments were performed with n=4 mice per group. The data presented are representative of two experiments with similar results and indicate the mean±SEM. P values are based on the unpaired two tailed Students t-test and are as follows.

FIG. 6 shows an amino acid sequence comparison between KU80 from *T. gondii* (Tg) and KU80 from *Arabidopsis thalianai* (At).

FIG. 8 depicts the construction of *T. gondii* strains disrupted in Ku80.

FIG. 10 shows homologous recombination rates in *Toxoplasma gondii*.

DETAILED DESCRIPTION OF THE INVENTION

Figure 1A:
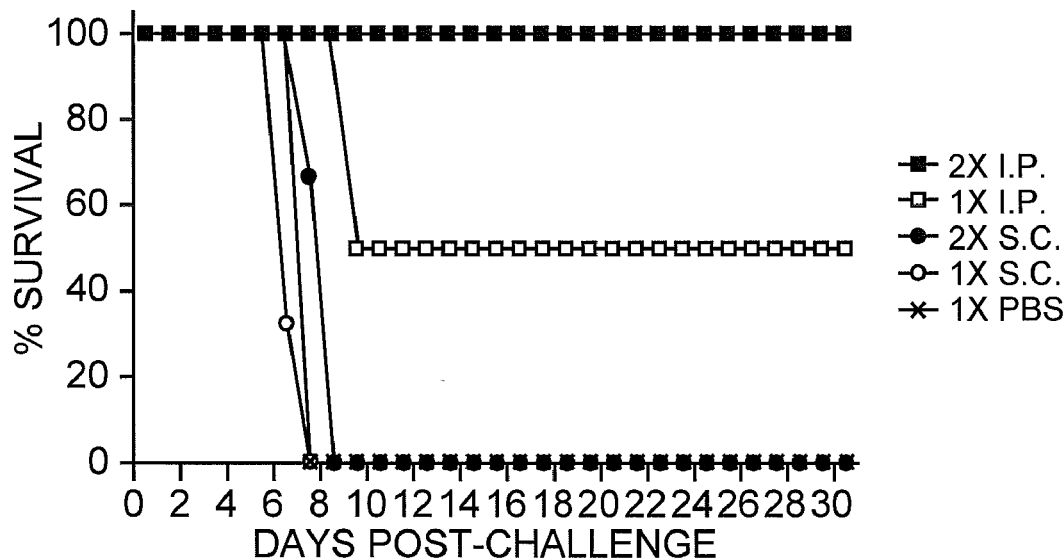
FIG. 1A, C57Bl/6 mice were unimmunized or immunized with either 1× s.c., 2× s.c., 1× i.p. or 2× i.p. and challenged 1 month after final immunization with $10^3$ RH and percent survival was measured.

While recombination mechanisms relying on sequence microhomology have been identified in parasites (Burton, et al. (2007) *Euk. Cell* 6:1773-1781), nonhomologous end-joining (NHEJ) mechanisms in parasites have not been previously described in the art. It has now been found that *Toxoplasma gondii* possesses NHEJ activity. By knocking out the function of the NHEJ pathway, strains exhibiting a high percentage of homologous recombination were obtained. Specifically, a strain lacking the KU80 coding region was generated. Using this ΔKu80 knockout strain, nearly 100% of transformants exhibited a double cross-over homologous recombination event resulting in gene replacement at the uracil phosphoribosyltransferase locus or the carbamoyl phosphate synthetase II locus. While NHEJ is functionally knocked out in the strains disclosed herein, with the exception of an increase in sensitivity to DNA damaging agents such as ionizing radiation and phleomycin, the strains grew normally, appeared normal, and could be maintained continuously in culture.

Accordingly, a mutant strain of *T. gondii* lacking function of the KU80-dependent NHEJ is useful for the construction of gene knockouts and gene replacements in *T. gondii*. Such gene knockouts and gene replacements can be used in the identification of drug targets, vaccine candidates, and characterization of virulence factors. The KU80-dependent NHEJ mutant is also useful for high-throughput knockout of *T. gondii* genes enabling a genome-wide knockout approach to individually inactivate each of the parasite's approximately 8000 genes. The KU80-dependent NHEJ mutant is also useful for creating *T. gondii* strains with several or many targeted gene knockouts or other genetic alterations based on targeted double homologous recombination. KU80-dependent NHEJ mutants are useful, for example, to construct crippled strains of *T. gondii* that in addition to being severely attenuated in their virulence also exhibit other desirable defects such as loss of ability to develop into tissue cysts, loss of sexual stages, loss of oocyst formation, or other developmental or phenotypic defects or changes that would enhance the efficacy or safety of vaccines based on KU80-dependent NHEJ mutants. Furthermore, the KU80-dependent NHEJ mutant is useful for the identification of drug targets as well as for screening candidate drugs that have anti-parasite activity against parasites such as *Plasmodium* species, *Cryptosporidium* species, or the like. For example, the KU80-dependent NHEJ mutant enables the rapid replacement of a *T. gondii* gene encoding a protein of interest with the corresponding or homologous gene from another parasite (e.g., *Plasmodium* or *Cryptosporidium*), thereby enabling a high-throughput drug screen to identify inhibitors of the exogenous protein. Similarly, such strains enable the rapid design of *T. gondii* strains carrying and expressing foreign antigens representing components of vaccines that are capable of vaccination against *T. gondii* and non-*T. gondii* diseases. A KU80-dependent NHEJ mutant strain for the first time also enables rapid development of precise and defined genetic descriptions of *T. gondii* strains necessary for their potential use(s) in treating human disease(s).

KU is known in the art as an ATP-dependent DNA helicase II protein involved in repairing DNA double-strand breaks by non-homologous end-joining (Hopfner, et al. (2002) *Curr. Opin. Struct. Biol.* 12:115-122; Featherstone & Jackson (1999) *Mutat. Res.* 434:3-15; Sandoval & Labhart (2004) *DNA Repair* (Amst) 3:13-21). KU is a heterodimer composed of 70 kDa and 80 kDa subunits (Walker, et al. (2001) *Nature* 412:607-614). Both of these subunits have strong sequence similarity and it has been suggested that they evolved by gene duplication from a homodimeric ancestor in eukaryotes (Hopfner, et al. (2002) supra). The prokaryotic KU members are homodimers and they have been predicted to be involved in the DNA repair system, which is mechanistically similar to the eukaryotic non-homologous end joining (Aravind & Koonin (2001) *Genome Res.* 11:1365-1374; Doherty, et al. (2001) *FEBS Lett.* 500:186-188). Yeast KU has been suggested to be involved in telomeric structure maintenance in addition to non-homologous end-joining (Baumann & Cech (2000) *Mol. Biol. Cell* 11:3265-3275). Furthermore, *Neurospora crassa* strains lacking KU70 and KU80 exhibit 100% homologous recombination, compared to 10 to 30% for a wild-type recipient (Ninomiya, et al. (2004) *Proc. Natl. Acad. Sci. USA* 101: 12248-12253). Some of the phenotypes of KU-knockout mice may indicate a similar role for KU at mammalian telomeres (Yoo & Dynan (1998) *Biochemistry* 37:1336-1343 1998).

Having demonstrated that a mutant *T. gondii* with a KU80 knockout exhibits a high percentage of homologous recombination as compared to wild-type *T. gondii*, the present invention features a mutant *T. gondii* which exhibits enhanced homologous recombination, wherein said mutant results from mutation of the KU80-dependent NHEJ pathway. Within the context of the present invention, a *T. gondii* mutant resulting from mutation of the KU80-dependent NHEJ pathway is intended to mean a mutation which decreases or abolishes the activity of a protein of the KU80-dependent NHEJ pathway. Such mutants are also referred to herein as knockouts.

In so far as KU80 has been demonstrated herein as a crucial component of the NHEJ pathway, this pathway is referred to herein as being KU80-dependent. While knockouts of the KU70 gene and DNA Ligase IV were attempted, knockout strains were not obtained. Not wishing to be bound by theory, it is possible that the targeting plasmids employed or the gene annotations relied on were incorrect thereby resulting in a failure to obtain knockouts at these two loci. In so far as Ku80 and Ku70 are expected to participate as a heterodimer complex, which first binds free DNA ends, wherein near the end of the NHEJ process, DNA ligase IV comes in and joins the broken DNA ends thereby healing the break, it is contemplated that any enzyme in the KU80-dependent NJEH pathway can be mutated to provide a *T. gondii* strain which exhibits enhanced homologous recombination. In this regard, the present invention embraces mutation of one or more loci of the KU80-dependent NJEH pathway including, but not limited to KU80, KU70, and DNA ligase IV.

As is conventional in the art, a gene or locus is the coding region and expression control sequences (e.g., promoter, enhancer, and the like) of a protein. In the context of the present invention, a mutation includes a substitution, deletion, or insertion at the desired locus which decreases or abolishes the activity of the protein encoded by said locus. For example, amino acid substitutions or insertions at the enzyme active site are expected to significantly decrease or abolish activity. Similarly, amino acid substitutions or insertions which destabilize (e.g., enhance degradation) the desired mRNA or protein can be used to decrease or abolish the activity a protein of the KU80-dependent NHEJ pathway. Moreover, promoter mutations which decrease or abolish expression of a protein of the KU80-dependent NHEJ pathway can be used to decrease or abolish activity. In particular embodiments, a mutant of the present invention lacks all or a substantial portion (e.g., more than 50, 60, 70, 80 or 90%) of the nucleic acids encoding a protein of the NHEJ pathway, so that homologous recombination in the mutant is enhanced. As is conventional in the art, the nucleic acids encoding a protein of interest include the nucleic acids beginning at the initiation codon (i.e., ATG) and ending at the termination codon (e.g., TGA, TAA and TAG). In particular embodiments, a mutant of the present invention lacks all, or a substantial portion, of the nucleic acids encoding KU80, KU70, or DNA ligase IV protein.

Nucleic acids encoding *T. gondii* KU80 are identified using moderately stringent hybridization conditions (e.g., at 42° C., 2×SSC) of a KU80 nucleic acid sequence disclosed herein (e.g., SEQ ID NO:1) or a KU80 nucleic acid sequence known in the art (e.g., from another species) with the KU80 nucleic acid sequence of the *T. gondii* genome. KU80 has been identified in a variety of species and is found under GENBANK Accession Nos. NP_066964 (*H. sapiens*), NP_033559 (*M. musculus*), NP_803154 (*R. norvegicus*), NP_596791 (*S. pombe*), NP_013824 (*S. cerevisiae*), NP_982917 (*E. gossypii*), XP_322163 (*N. crassa*), NP_564520 (*A. thaliana*), and NP_001051947 (*O. sativa*). An exemplary *T. gondii* KU80 nucleic acid sequence is set forth herein as SEQ ID NO:1, wherein the ATG start codon is at nucleotide 8742, the TAG termination codon is at nucleotide 13922, and exons 1-4 are respectively located at nucleotide 8742-9338, 10199-11003, 11331-11700, and 12053-13922 of SEQ ID NO:1. The resulting KU80 protein is set forth herein as SEQ ID NO:2. The nucleic acid sequence encoding KU80 spans 2,749,500 to 2,729,500 on chromosome XI of *T. gondii* and is annotated in the *T. gondii* ME49 strain sequence database (provided by The Institute for Genomic Research), under Accession No. 583.m05492, as encoding a hypothetical protein. Indeed, there are only short stretches of sequence identity and similarity at the amino acid level between KU80 from *T. gondii* and KU80 from *A. thaliana* (FIG. 6).

Similarly, nucleic acids encoding *T. gondii* KU70 or DNA ligase IV are readily identified by the skilled artisan based upon moderately stringent hybridization (e.g., at 42° C., 2×SSC) of a KU70 or DNA ligase IV nucleic acid sequence or a KU70 nucleic acid sequence known in the art (e.g., from another species) with the KU70 or DNA ligase IV nucleic acid sequence of the *T. gondii* genome. For example, KU70 has been identified in a variety of species and is found under GENBANK Accession Nos. NP_001460 (*H. sapiens*), NP_034377 (*M. musculus*), NP_620780 (*R. norvegicus*), NP_588445 (*S. pombe*), NP_014011 (*S. cerevisiae*), XP_328996 (*N. crassa*), NP_564012 (*A. thaliana*), and NP_001059061 (*O. sativa*). Likewise, DNA ligase IV has been identified in a variety of species and is found under GENBANK Accession Nos. NP_001091738. (*H. sapiens*), NP_001099565 (*R. norvegicus*), and NP_795927 (*M. musculus*).

A mutant of the present invention can be generated using any suitable method conventionally employed for producing gene knockout mutants of *T. gondii*. For example, the mutant can be obtained by the single cross-over integration, e.g., as disclosed by Fox & Bzik ((2002) *Nature* 415(6874):926-9) or using a double-crossover gene replacement, e.g., as disclosed by Mercier, et al. ((1998) *Infect. Immun.* 66:4176-82). See also Wang, et al. (2002) *Mol. Biochem. Parasitol.* 123(1):1-10. In general, the generation of a mutant *T. gondii* includes isolating the nucleic acid molecule encoding the KU80-dependent NHEJ pathway protein from *T. gondii* (e.g., as described herein); replacing, mutating, substituting or deleting all or a portion (e.g., one or more bp) of the gene to disrupt the promoter, regulatory sequence(s) and/or coding region of the protein; and integrating the disrupted molecule (e.g., via single- or double-crossover homologous recombination events) into the genome of *T. gondii*. Upon selection, i.e., marker protein expression or genomic DNA analysis, a mutant with a KU80-dependent NHEJ pathway protein knockout is obtained. In particular embodiments, the selectable marker is selected for by positive and negative selection (e.g., HXGPRT), such that the selectable marker can be easily deleted from the targeted locus by homologous recombination and, upon negative selection, recovered for use again in a sequential process of positive and negative selection to create strains harboring multiple gene knockouts or replacements in the KU80-dependent NHEJ pathway knockout strain(s). Disruption of all or a portion of a gene of interest can be achieved by, e.g., replacing the coding sequence with a nucleic acid molecule encoding selectable marker, replacing the coding sequence with a nucleic acid molecule encoding an exogenous protein, substituting the promoter with a mutated promoter which can no longer be recognized by *T. gondii* transcription proteins (i.e., a promoter mutation), etc. As is known to the skilled artisan, subsequent restriction endonuclease digestion and Southern blot analysis of the mutant *T. gondii* genomic DNA can be used to confirm the knockout.

As will be appreciated by the skilled artisan, any suitable marker-encoding nucleic acid can be used to identify a *T. gondii* which has been transformed so long as it can be phenotypically detected in the mutant strain. Suitable marker proteins include, but are not limited to, positive and negative selectable markers such as HXGPRT, thymidine kinase, hygromycin resistance, cytosine deaminase, DHFR (dihydrofolate reductase), bleomycin, chloramphenicol acetyl transferase, or combinations thereof. It is contemplated that the nucleic acid molecule encoding the marker protein can be used to replace or substitute all or a portion of the promoter or coding sequence of the locus of a KU80-dependent NHEJ pathway protein to generate a knockout or mutant.

While the mutant of the present invention can be produced from a virulent type I strain such as RH (as exemplified herein), a type II strain as well as a type III strain can also be employed so that the underlying development of tissue cysts as well as oocysts in *Toxoplasma* infection can be analyzed.

KU80 knockout strains disclosed herein retained the same level of virulence as parental RH in that fewer than 50 tachyzoites were uniformly lethal in B6 (c57/black6) mice. Because the *T. gondii* mutants of the present invention are virulent in a mouse model, particular embodiments embrace producing a KU80-dependent NHEJ pathway mutant which is attenuated. As is conventional in the art, the term attenuated refers to a weakened and/or less vigorous strain of *T. gondii*. Desirably, the attenuated mutant of the invention is capable of stimulating an immune response and creating immunity but not causing illness. Attenuation can be achieved by conventional methods including, but not limited, the generation of a pyrimidine auxotroph. A pyrimidine auxotroph of the invention can be generated by disrupting mechanisms for pyrimidine acquisition including, mutating proteins involved in pyrimidine synthesis as well as pyrimidine salvage (e.g., enzymes or transporters). Specifically, pyrimidine auxotrophs can be produced by knocking out or mutating one or more of CPSII (carbamoyl phosphate synthetase II; Gene loci ID 583.m05492), OMPDC (orotidine 5'-monophosphate decarboxylase; Gene loci ID 55.m04842), OPRT (orotate phosphoribosyltransferase; Gene loci ID 55.m04838), DHO (dihydroorotase; Gene loci ID 83.m00001), aspartate transcarbamylase (ATC), dihydroorotase dehydrogenase (DHOD), uridine phosphorylase (UP), uracil phosphoribosyltransferase, purine nucleoside phosphorylase (e.g., PNP), or a nucleobase/nucleoside transporter of pyrimidine bases or nucleosides (e.g., NT2 or NT3). Indeed, any single knockout or combination of knockouts is contemplated to achieve an attenuated strain. By way of illustration, the present embraces an attenuated strain or vaccine strain constructed by a single knockout in any of the six de novo pyrimidine biosynthetic genes (CPS, ATC, DHO, DHOD, OPRT or OMPDC), knockout of two or more genes of the de novo pyrimidine synthetic pathway, or knockout of a de novo pyrimidine synthesis gene in combination with a knockout in a pyrimidine salvage gene (e.g., coding for enzymes UP, PNP, or uracil phosphoribosyltransferase) and/or in combination with a knockout of a nucleobase/nucleoside transporter of pyrimidine bases or nucleosides. Such mutations can be generated by substitution, deletion or insertion as discussed and exemplified herein. It is contemplated that because an attenuated pyrimidine auxotroph of *T. gondii* (e.g., a CPSII knockout) provides protection against infection by parasitic *T. gondii* and induces a Th-1 immune response, any attenuated mutant of *T. gondii* can be used as a vaccine against *T. gondii* without the complication of dead host cells and host-derived inflammation. Thus, particular embodiments of the present invention embrace a vaccine including an attenuated pyrimidine auxotroph of *T. gondii* with mutation of a locus encoding a protein of the KU80-dependent NHEJ pathway.

In addition, or alternative to attenuation, mutants of the invention can be multiply crippled strains of *T. gondii* that exhibit other desirable defects such as loss of ability to develop into tissue cysts, loss of sexual stages, loss of oocyst formation, or other developmental or phenotypic defects or changes that would enhance the efficacy or safety of vaccines based on mutants of the invention. For example, while certain proteins have been shown to contain T-cell epitopes (e.g., GRA4, GRA6, and ROP7) and may be important in immunity, other proteins signal to host cells (e.g., ROP16, ROP18) and may present tools to manipulate mammalian cells. See Mercier, et al. (1998) *Infect. Immun.* 66:4176-4182; Lecordier, et al. (1999) *Mol. Biol. Cell.* 10(4):1277-87; Igarashi, et al. (2008) *Gen. Mol. Res.* 7(2):305-313. Therefore, certain embodiments of this invention embrace mutating or deleting one or more of the GRA genes (i.e., GRA2, GRA3, GRA4, GRA5, GRA6, GRA7, GRA8, and GRA9) and/or ROP genes (i.e., ROP16 and ROP18) to modify or improve the ability of attenuated *Toxoplasma* to present antigens in vaccine formulations. Such an approach could improve vaccine efficacy and provide insight into how to manipulate host cells for new therapeutics. The GRAs occupy the vacuole space or vacuole membrane, which are key intersections that exogenous antigens (i.e. a vaccine formulation expressed by attenuated *T. gondii*) must pass through to get presented onto the MHCI or MHCII of the host cell.

According to another feature of the invention, an attenuated pyrimidine auxotroph of *T. gondii* with mutation of a locus encoding a protein of the KU80-dependent NHEJ pathway can be used for intracellular vaccination by delivering exogenous antigens from non-*T. gondii* disease agents (i.e., antigens not naturally expressed by the *T. gondii*). In one embodiment, the exogenous antigen is expressed by *T. gondii*, secreted into the parasite vacuole and eventually into the cytosol of the mammalian host cell. The *T. gondii*-expressed exogenous antigen subsequently enters the mammalian antigen presenting cell's (APC) antigen processing and presenting pathway as a substrate for generation of class I and class II peptides which generate CD8 and CD4 T cell responses. Accordingly, in one embodiment of the present invention, an attenuated mutant of the invention harbors a nucleic acid molecule encoding an exogenous protein which is a non-*T. gondii* antigen. In this regard, the inventive auxotrophic mutant can be used to vaccinate against both *T. gondii* and against any non-*T. gondii* antigen(s) encoded by gene(s) expressed in the *T. gondii* mutant. This includes both protein antigens and also non-protein antigens that could be produced by genes within the *T. gondii* carrier, such as polysaccharides and lipids. While certain embodiment embrace the expression of antigens from pathogenic organisms, e.g., bacteria, fungi, viruses, and parasites, other embodiments include any other antigen to which an immune response would be desired, e.g., host antigens such as tumor antigens.

Specific examples of exogenous antigens include tetanus toxoid (tetC); malarial antigens such as circumsporozoite protein (CSP) and merozoite surface protein-1 (MSP-1); *Bacillus anthracis* protective antigen; *Yersinia pestis* antigens (e.g., F1+V and F1-V fusion); antigens from intracellular bacterial pathogens such as *Francisella tularensis, Mycobacteria, Legionella, Burkholderia* (e.g., *B. pseudomallei* and *B. mallei*), *Brucella* species and *Coxiella*; antigens from viruses, particularly intracellular invaders such as HIV; other toxoids such as botulinum toxoid or Epsilon toxin; tumor antigens; multiagent biodefense antigens; antigens from non-biothreat infectious agents; plague antigens; and combinations of any of these. As indicated above, it is also contemplated that exogenous genes encoding enzymes which synthesize non-protein antigenic products, e.g., lipids or polysaccharides, can be expressed in the *T. gondii* platform. Care should be taken to ensure that antigens being expressed in *T. gondii* are not functional virulence factors. Therefore, it may be desirable to use known protective antigens not representing virulence factors or use mutated genes that do not encode complete toxin or virulence factors.

One advantage of multivalent vaccines is that protection against multiple disease agents can be attained with a single vaccine formulation. The protective immune response to a *T. gondii* uracil auxotroph clearly involves both a humoral (antibody) response and the cell-mediated component of immunity, thus a diverse immune response to any expressed antigen is possible. In this regard, the instant *T. gondii*-based vaccine can serve as an agent of protection and of adjuvancy for any exogenous antigen(s) expressed.

It is further contemplated that an attenuated or non-attenuated mutant of *T. gondii* can be used to express any other genes one would want to express within a mammalian host cell. This could include genes encoding therapeutic peptides or proteins, e.g., therapeutic antibodies (e.g., Trastuzumab) proteins (e.g., interferons, blood factors, insulin, erythropoietin, and blood clotting factors), or enzymes (e.g., asparaginase, catalase, lipase, and tissue plasminogen activator) used in the treatment of diseases or conditions; as well as proteins, enzymes or peptides of use in screening assays to identify inhibitors or activators (i.e., effectors) of the same. Such proteins are routinely expressed in other systems, e.g., yeast, mammalian cells lines, bacteria or insect cells, such that one skilled in the art could readily obtain nucleic acids encoding such proteins and express them in a mutant *T. gondii*.

The *T. gondii* mutant of the present invention can accommodate multiple expression constructs. Therefore, nucleic acid molecules encoding exogenous proteins, antigens and the like can be integrated into the *T. gondii* genome, e.g., as part of the nucleic acid molecule used to disrupt the promoter, regulatory sequences, or open reading frame of a protein of the KU80-dependent NHEJ pathway or at any other suitable location in the genome (e.g., at non-essential locus).

The basic criteria for exogenous protein expression are that the gene is a non-*T. gondii* gene or coding sequence and the gene or coding sequence is able to be expressed directly or indirectly from a recombinant molecule in a *T. gondii* cell. In this regard, it is desirable that the promoter employed is recognizable by *T. gondii*. Moreover, it is desirable that the promoter promotes transcription of the protein coding sequence when the *T. gondii* is inside mammalian cells. To this end, particular embodiments embrace the use of a *T. gondii* promoter. Known promoter and other regulatory elements (e.g., 5' UTR, 3' UTR, etc.) which can be operably linked to the coding sequence of an exogenous protein of interest so that the exogenous protein is expressed in *T. gondii* include, but are not limited to, sequences from the *T. gondii* SAG1 gene (Striepen, et al. (1998) *Mol. Biochem. Parasitol.* 92(2):325-38) or the *T. gondii* NTPase gene (Robibaro, et al. (2002) *Cellular Microbiol.* 4:139; Nakaar, et al. (1998) *Mol. Biochem. Parasitol.* 92(2):229-39). Alternatively, suitable regulatory sequences can be obtained by known trapping techniques. See, e.g., Roos, et al. (1997) *Methods* 13(2):112-22. Promoters of use in accordance with the present invention can also be stage-specific promoters, which selectively express the exogenous protein(s) or antigen(s) of interest at different points in the obligate intracellular *T. gondii* life cycle. Moreover, it is contemplated that an endogenous promoter can be used to drive expression of the exogenous protein or antigen by, e.g., site-specific integration at the 3' end of a known promoter in the *T. gondii* genome.

When employed as a delivery vector or a vaccine for generating an immune response or protection against infection by *T. gondii* and/or a non-*T. gondii* disease, particular embodiments provide that the mutant *T. gondii* is in admixture with a pharmaceutically acceptable carrier. Suitable carriers and their formulation are described, for example, in Remington: The Science and Practice of Pharmacy, Alfonso R. Gennaro, editor, 20th ed. Lippincott Williams & Wilkins: Philadelphia, Pa., 2000. Furthermore, it has now been shown that ex vivo loading of dendritic cells, macrophages, and peritoneal cells with cps1-1, then immunizing an animal with these loaded cells leads to successful immunization. For example, dendritic cells loaded with a CPSII mutant provide the strongest immune response in animals and produce long lasting CD8 T cell responses and long lasting immune memory. Accordingly, it is contemplated that a *T. gondii* mutant of the invention which is also an pyrimidine auxotroph can be administered via loading of dendritic cells, macrophages, and/or peritoneal cells.

Administration of a mutant *T. gondii* disclosed herein can be carried out by any suitable means, including parenteral injection (such as intraperitoneal, subcutaneous, or intramuscular injection), orally, or by topical application (typically carried in a pharmaceutical formulation) to an airway surface. Topical application to an airway surface can be carried out by intranasal administration (e.g., by use of dropper, swab, or inhaler which deposits a pharmaceutical formulation intranasally). Oral administration can be in the form of an ingestible liquid or solid formulation. In particular embodiments, a *T. gondii* mutant is formulated for administration via intraperitoneal, intranasal or intravenous routes.

An attenuated mutant *T. gondii* or vaccine containing the same can be employed in various methods inducing an immune response and protecting a subject against infection by *T. gondii* and/or a non-*T. gondii* disease. Such methods generally involve administering to a subject in need of treatment (e.g., a subject at risk of being exposed to an infectious disease or at risk of developing cancer) an effective amount of an attenuated mutant *T. gondii* or vaccine of the present invention thereby generating an immune response to the antigen expressed by the attenuated mutant *T. gondii* or vaccine and protecting the subject against infection by *T. gondii* and/or the non-*T. gondii* disease. An effective amount, as used in the context of the instant invention, is an amount which produces a detectable Th-1 immune response or antibody response to an antigen thereby generating protective immunity against the pathogen or disease from which the antigen was derived or associated. As such, an effective amount prevents the signs or symptoms of a disease or infection, or diminishes pathogenesis so that the disease or infection is treated. Responses to administration can be measured by analysis of subject's vital signs, monitoring T cell or antibody responses, or monitoring production of IFN-γ, IL-12p40, and/or IL-12p70 according to the methods disclosed herein or any suitable method known in the art.

Administration can be given in a single dose schedule, or a multiple dose schedule in which a primary course of treatment can be with 1-10 separate doses, followed by other doses given at subsequent time intervals required to maintain and or reinforce the response, for example, at 1-4 months for a second dose, and if needed, a subsequent dose(s) after several months.

The exact dosage for administration can be determined by the skilled practitioner, in light of factors related to the subject that requires prevention or treatment. Dosage and administration are adjusted to provide sufficient levels of the composition or to maintain the desired effect of preventing or reducing signs or symptoms of the disease or infection, or reducing severity of the disease or infection. Factors which may be taken into account include the severity of the disease state, general health of the subject, age, weight, and gender of the subject, diet, time and frequency of administration, drug combination(s), reaction sensitivities, and tolerance/response to therapy.

While the instant compositions and methods find application in the prevention and treatment of diseases or infections of mammals, in particular humans, the invention should be construed to include administration to a variety of animals, including, but not limited to, cats, dogs, horses, cows, cattle, sheep, goats, birds such as chickens, ducks, and geese. In this regard, the instant invention is also useful against potential bioterrorism aimed at agriculture and populace, e.g., *Brucella* and anthrax. As such, the instant *T. gondii* vector platform can be employed by both pharmaceutical and agribusiness to produce multivalent vaccines with intracellular delivery to create commercial multiagent vaccines for people and livestock.

Based on the ability of the instant *T. gondii* mutant to mediate specific and defined gene targeting events, this mutant will for the first time enable precise and appropriate genetic descriptions of vaccine strains or other genetically modified strains that are necessary for safe use in humans as well as FDA approval. Consequently, this mutant will enable the development of completely safe multiply attenuated *T. gondii* strains with no detectable virulence as well as strains that carry genes encoding one or more exogenous antigens, proteins, or peptides having therapeutic value as vaccine components, drug components, or signaling components. The potential therapeutic uses of the described technology extend to many human diseases and conditions, as well as infectious diseases.

Based upon the high percentage of homologous recombination events that can take place upon introducing a gene knockout or gene replacement construct into a mutant *T. gondii* of the invention, this invention also features a method for generating a gene knockout or gene replacement in *T. gondii*. In general, a gene of interest (e.g., encoding an enzyme or signal transduction protein) is inserted into a gene knockout construct, and as with the generation of the instant KU80 knockout strain, all or a portion of the gene of interest is replaced, mutated, substituted or deleted to disrupt or replace the promoter, regulatory sequence(s) and/or open reading frame of the gene or interest. As demonstrated herein, target flank sequences of approximately 500 base pairs of homology are sufficient for efficiently targeting gene knockouts in *T. gondii*. Moreover, the selectable marker can be deleted from the targeted locus by negative selection and the same selectable marker (for example HXGPRT) can be used to target another locus to construct mutant strains that contain sequentially developed multiple knockouts. For example, the promoter of the gene of interest can be replaced with an exogenous promoter which can be regulated by, e.g., light, tetracycline, a heavy metal, etc. As another example, the coding region of a gene of interest (e.g., including promoter and terminator sequences) can be replaced with a heterologous coding region from another organism. In this regard, proteins from other parasites such as *Plasmodium* or *Cryptosporidium* species can be introduced into *T. gondii*. As yet a further example, the coding sequence of a gene of interest can be replaced with a selectable marker to produce a strain deficient in the expression of the gene of interest. The gene knockout or gene replacement construct is then introduced into a KU80-dependent NHEJ knockout strain of *T. gondii*, and knockout mutants or replacement mutant of the gene of interest are screened for. Screening can include selection for marker expression, genomic DNA analysis, as well as phenotypic screening.

In so far as mutant *T. gondii* of the present invention can be modified to express any protein of interest, particular embodiments of this invention feature the use of a transgenic *T. gondii* strain expressing a human therapeutic target protein or enzyme in live, whole-cell screening assays for identifying effectors (i.e., inhibitors or activators) of said target protein or enzyme. Such whole-cell screening assays are routinely practiced in the art using other systems, e.g., yeast, mammalian cell lines, or bacteria, and can be readily adapted for use with *T. gondii*-infected cells. In accordance with such a method, a cell (i.e., a mammalian cell) harboring a mutant *T. gondii* of the invention which expresses a human therapeutic target protein or enzyme is contacted with a test agent and it is determined whether the test agent modulates the expression or activity of the protein or enzyme. The modulation of expression can be determined by conventional assays (e.g., western analysis, northern analysis, ELISA, etc.). Methods for determining whether an agent modulates activity will be dependent on the protein or enzyme be assayed. For the purposes of the present invention, a human therapeutic target protein or enzyme is any human protein, which is known to be involved in the manifestation of a disease or condition (e.g., oncogenes). In this regard, inhibition or activation of the human therapeutic target protein or enzyme results in the prevention or treatment of the disease or condition. Human therapeutic target proteins or enzymes are well-known to those skilled in the art.

The addition to the above-described uses, the mutants of this invention also find application as "sensors" of the intracellular mammalian cell environment. The cellular events inside of living mammalian cells during drug treatments for cancer, autoimmune disease and any other disease state or treatment state is typically difficult to measure, but is of major commercial interest. Many conventional treatments work by starving cells of pyrimidines or purines, or by adding pyrimidines (5-fluorouracil for cancer) or purines (mercaptopurine for cancer) derivatives. In this regard, *Toxoplasma* mutants have been made that sense the concentration of specific molecules present in the host cell.

For example, the pyrimidine auxotrophs disclosed herein rely on host cell uracil and uridine (and deoxyuridine) for growth. The double knockout in de novo synthesis and parasite uridine phosphorylase relies strictly on uracil. Thus, these mutants can both "sense" the host cell environment for these compounds measured by parasite growth rate, and also "sense" cytotoxic concentrations of 5-fluorouracil or 5-fluorouridine (or deoxyuridine) concentrations based on stasis and/or death of the intracellular parasite. The purine mutants deficient in IMPDH, or the double knockout in IMPDH (inosine monophosphate dehydrogenase) and PNP (purine nucleoside phosphorylase) can likewise be used to sense purine levels. For example, the IMPDH knockout can measure host cell concentrations of guanosine, guanine, and xanthine, and the double knockout more specifically can measure the concentration of just the nucleobases guanine and xanthine. In addition, *Toxoplasma* is a cholesterol auxotroph and must get its cholesterol from the host cell environment, such that cholesterol levels can likewise be sensed by *Toxoplasma*. Generating additional single or double mutants will provide *Toxoplasma* mutants that sense a single specific molecule in the host cell environment (for example the case above with just uracil). Indeed, any molecule that the parasite needs from the host can be sensed by a mutant strain of this invention simply by making the appropriate parasite mutant strain.

As with *T. gondii*, a KU80 homologue was also identified in the related coccidia parasite *Eimeria tenella* by searching raw data from the Sanger Institute genome database. It is contemplated that knockout of the *E. tenella* KU80 will likely enhance homologous recombination in this organism as well. Indeed, it is contemplated that a KU80 homolog will be present in a variety of coccidian parasites from the Suborder Eimeriina, including the families Lankesterella, Aggregatidae, Cryptosporridae, Calypytosporidae, Eimeriidae, and Sarcocystidae, wherein knockout of KU80 will provide a valuable tool for the research and development of therapies and vaccines against these parasites.

The following non-limiting examples are provided to further illustrate the present invention.

EXAMPLE 1

*T. gondii* Vaccine to Elicit Cell-Mediated Immunity

This example describes the host immune response to cps1-1 using various routes of immunization, as well as APC cell-dependence of immune control of infection, the type of immunity responsible for long lasting protection and, the dynamics of cell and cytokine profiles during the first eight days of exposure to cps1-1.

Parasitic Material. Most of the work described herein used the RH strain of *Toxoplasma gondii* which is the most commonly used laboratory strain amongst *Toxoplasma* researchers (Pfefferkorn, et al. (1976) *Exp. Parasitol.* 39:365-376). Due to its long history of continuous passage in the laboratory, this strain is highly virulent in animals and grows rapidly in culture making it ideal for obtaining large amounts of material. However, it has lost the ability to go through the complete sexual cycle in cats.

Detailed methods for storage and replication assays of *T. gondii* are routine and well-known, for example, Roos, et al. (1994) *Meth. Microb. Path.* 45:23-65; Fox, et al. (1999) supra. The attenuated uracil auxotroph, i.e., CPSII mutant, is as described by Fox & Bzik ((2002) supra).

Molecular Methods. Molecular methods including DNA isolation, restriction, Southern blot analysis, hybridization, and PCR reactions used herein are all well-known, for example, Bzik, et al. (1987) *Proc. Natl. Acad. Sci. USA* 84:8360-8364 and Fox, et al. (1999) supra. Transfection of *T.* gondii was also performed in accordance with routine procedures (Roos, et al. (1994) supra and Fox et al. (1999) supra).

Animal Studies. Adult 6-8 week old C57BL/6 and C57BL/6 B cell-deficient mice (μMT) (Kitamura, et al. (1991) *Nature* 350:423-426) were obtained from Jackson Labs Bar Harbor, Me.) as were Balb/c inbred mice and balb/c mice bearing a homozygous knock-out of interferon gamma (gko) Mice were maintained in Tecniplast Seal Safe mouse cages on vent racks. μMT mice were maintained in sterile conditions.

Tachyzoite parasites were aseptically handled and purified from freshly lysed monolayers of infected HFF cells through a sterilized 3 micron polycarbonate membrane (Nucleopore, Cambridge, Mass.). Parasite concentration was scored microscopically in a hemocytometer. Purified parasites were pelleted at 1500 g for 10 minutes and washed in sterile EMEM media with no supplements and without disturbing the parasite pellet. The centrifuge tube was centrifuged once more for 2 minutes and the supernatant removed and replaced with EMEM media containing no supplements in a volume of EMEM to give a 10 times higher concentration (per/ml) of parasites than the highest dose. This was done so inoculation of 0.1 ml of this solution would equal the highest parasite dose. Parasites were gently resuspended in sterile EMEM (no additions).

Mice were immunized with $1 \times 10^6$ cps1-1 tachyzoites i.p, s.c, or i.v. once respectively or twice 14 days later with the same tachyzoite dose. At indicated times following the last immunization, mice were challenged with either low $1 \times 10^2$ or high ($1 \times 10^3$ or $1 \times 10^4$) doses of viable RH or PLK Tachyzoites i.p. (Villegas, et al. (1999) *J. Immunol.* 163:3344-3353).

Following inoculation of mice the residual volume of unused tachyzoite parasites was returned to the sterile hood and dilutions were made to represent 200 and 400 parasite plaques on 25 $cm^2$ HFF flasks assuming 100% recovery of parasites after centrifugation/resuspension and 100% percent viability. Then, following a 7 day plaque assay, actual plaques were counted, post-inoculation of mice, and the percent viable PFU ratio to parasite counts in the hemocytometer were determined microscopically in every experimental infection. Uniformly, all of the mutants described herein as well as RH parasites always fell in the range of 0.4 to 0.6 viable PFU per parasite counted using these conditions. Following inoculation of mice, mice were observed daily for signs of infection (or distress) or death.

Ex vivo Infection. Dendritic cells (DCs) were obtained from the spleens of wild-type mice and purified using EASY-SEP CD11c positive selection per the manufacturer's instructions. Briefly, spleens were harvested and injected with 1-2 ml of DNAse I/Liberase CI (Roche, Indianapolis, Ind.) followed by incubation at 37° C. for 30 minutes. Spleens were then ground through a 70-μm mesh nylon strainer and collected. DCs were then purified by CD11c magnetic positive selection and purity was verified as per manufacturer's instructions (StemCell Technologies Inc., Vancouver, BC). PECs were obtained from naïve mice and from a portion of those cells peritoneal-derived macrophages were obtained. PECs were plated at $4 \times 10^6$ cells/ml in DMEM with 10% FBS and 1× antimicrobe/antimycotic and incubated for 4 hours at 37° C. Non-adherent cells were physically removed by washing gently with medium and remaining adherent cells were examined for macrophage purity via flow cytometry for percentage of CD11b+ cells (>90%) (Da Gama, et al. (2004) *Microbes Infect.* 6:1287-1296). The DCs, PECs, and PEC-derived macrophages obtained were plated at $2 \times 10^6$ cells/ml in infection medium consisting of EMEM with 1% FBS, 1× antimicrobic/antimycotic and supplemented with 250 nM uracil (SIGMA, St. Louis, Mo.). Purified cps1-1 tachyzoites were inoculated into the wells containing specific cell populations at $5 \times 10^5$ parasites/ml and infected cultures were incubated for 12 hours at 37° C. Infected cells were examined by light microscopy and at the time of harvest typically contained 4-8 cps1-1 tachyzoites. DCs, macrophages and PECs were washed to remove any residual extracellular tachyzoites, harvested and resuspended in PBS at $5 \times 10^5$ cells/ml followed by inoculation into naïve recipient mice via tail vein injection.

Cps1-1 Tachyzoites Induce a Completely Protective Long Lasting Immune Response Against High Dose Lethal Challenge with Hypervirulent RH Tachyzoites. Having demonstrated herein that live attenuated cps1-1 tachyzoites protect Type II *T. gondii* resistant BALB/C mice against a low dose lethal challenge in a single inoculation dose, immunization with live attenuated cps1-1 and mechanisms of immune protection elicited in the priming phase of the highly sensitive C57BL/6 mouse background was analyzed. Live attenuated cps1-1 tachyzoites were effective in producing immunological protection against high dose lethal challenge in C57Bl/6 mice. C57BL/6 mice were immunized intraperitoneally twice with $1 \times 10^6$ cps1-1 tachyzoites, 14 days apart, then challenged i.p. 4 weeks after the final immunization with a high $1 \times 10^3$ lethal dose of RH tachyzoites. Mice immunized with the cps1-1 vaccine were completely protected (100%) when followed up to 30 days post-challenge, whereas naïve mice uniformly succumbed to infection by day 10 post-challenge. Cps1-1 immunized mice were continuously monitored over 18 months post-challenge and uniformly survived challenge infection to old age, indicating that the cps1-1 vaccine induces long lasting protective immunity.

Intravenous Immunization with cps1-1 Tachyzoites Alone or ex vivo cps1-1 Infected DCs or PECs Induce Long Lasting Protective Immunity. Numerous studies have reported that the route of immunization is a critical factor in determining vaccine effectiveness (Bourguin, et al. (1998) Infect. Immun. 66:4867-4874; McLeod, et al. (1988) J. Immunol. 140:1632-1637; Aline, et al. (2004) Infect. Immun. 72:4127-4137). To explore the importance of the route of vaccination to the development of long lasting immunity in the cps1-1 model, C57Bl/6 mice were immunized either once i.p., or subcutaneously (s.c.), or twice i.p, or s.c. with $1 \times 10^6$ cps1-1 tachyzoites. Four weeks post-immunization, mice were challenged i.p. with a high $5 \times 10^4$ dose of high in vitro passaged hypervirulent Type II strain PLK tachyzoites and percent survival was monitored to 30 days post-challenge (Howe, et al. (1996) Infect. Immun. 64:5193-5198; Sibley & Howe (1996) Curr. Top. Microbiol. Immunol. 219:3-15). Mice immunized twice i.p. were completely protected against this high dose PLK challenge while mice immunized once i.p. showed lower survival (FIG. 1). Unexpectedly, mice immunized s.c. did not survive challenge infection (FIG. 1). The previously observed protection conferred by immunization with temperature-sensitive strain ts-4 tachyzoites (McLeod, et al. (1988) supra) must require parasite replication which does not occur in the non-replicating cps1-1 vaccine.

Figure 1B:
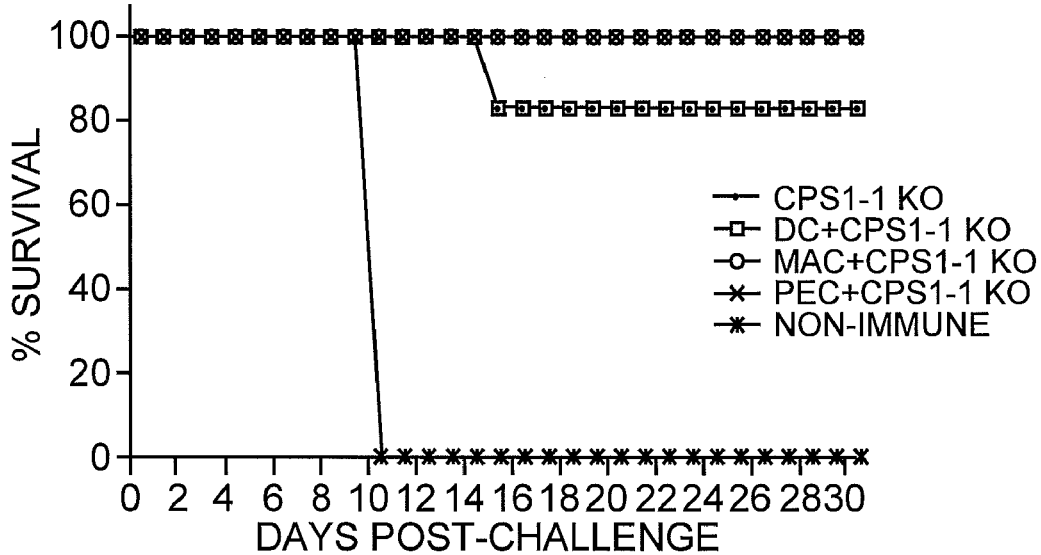
FIGS. 1B and 1C, C57BL/6 mice were unimmunized or immunized once with either cps1-1 knock-out alone or DC, pMAC, or PEC loaded ex vivo for 12 hours with cps1-1 knock-out. Two months (FIG. 1B) or 6 months (FIG. 1C) post-i.v. immunization, mice were challenged with $10^2$ tachyzoites of RH i.p. and percent survival was measured out to 30 days post-challenge. Data represents one experiment performed with 6 mice per immunization group.
Figure 1C:
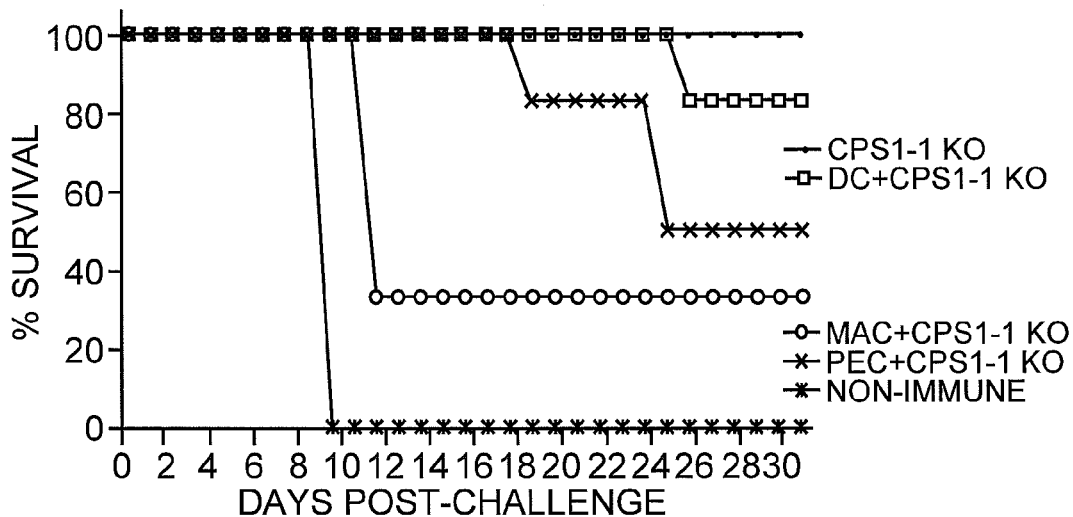

To further elucidate effective routes of cps1-1 immunization, it was determined whether immunizations given intravenously (i.v.) were capable of inducing protective immunity against lethal RH challenge. Mice were immunized once with $1 \times 10^6$ cps1-1 tachyzoites i.v. then challenged 2 months (FIG. 1A) or 6 months (FIG. 1B) post-immunization with a low dose ($1 \times 10^6$) of RH tachyzoites i.p. and survival was monitored. All mice immunized i.v. with cps1-1 survived challenge whereas all naïve control mice given PBS alone succumbed to challenge infection. Unexpectedly, naïve mice infected i.v. with RH tachyzoites succumbed 2 days earlier than naïve mice injected i.p., indicating that parasitemia is critical to lethal pathogenesis. Since the i.v. route was effective in inducing long lasting protective immunity in a single inoculation dose and previous studies exploring the use of professional APCs loaded ex vivo with antigen have achieved protection against lethal challenge, the effectiveness of specific host APC types in the development of protective immunity was examined (Bourguin, et al. (1998) Infect. Immun. 66:4867-4874; Aline, et al. (2004) Infect. Immun. 72:4127-4137). Mice were immunized once with ex vivo cps1-1 infected DCs, PECs and macrophages derived from resident PECs i.v. and then were challenged at 2 (FIG. 1A) or 6 months (FIG. 1B) post-immunization with a low dose of RH tachyzoites and survival was monitored. Immunization with ex vivo cps1-1 infected DCs, PECS, or PEC-derived macrophages resulted in nearly complete survival of RH challenged mice at 2 months post-immunization and was not significantly different from mice immunized with cps1-1 i.v. (FIG. 1A). When lethal challenge was administered at 6 months (FIG. 1C), differences in percent survival of mice immunized with ex vivo cps1-1 infected DCs (83% survival), PECs (50% survival), and PEC-derived macrophages (33% survival) were observed and all cps1-1 immunized mice survived longer than PBS naïve control mice (all p-values=0.0009). Percent survival of mice immunized with ex vivo cps1-1 infected DCs and PECs was of similar statistical significance to mice immunized i.v. with cps1-1 tachyzoites, indicating that although peritoneal macrophages were effective at inducing protection at 2 months, this protection was not as long lasting as that induced by ex vivo cps1-1 infected DCs and PECs (compare FIGS. 1B and 1C)

Figure 2A:
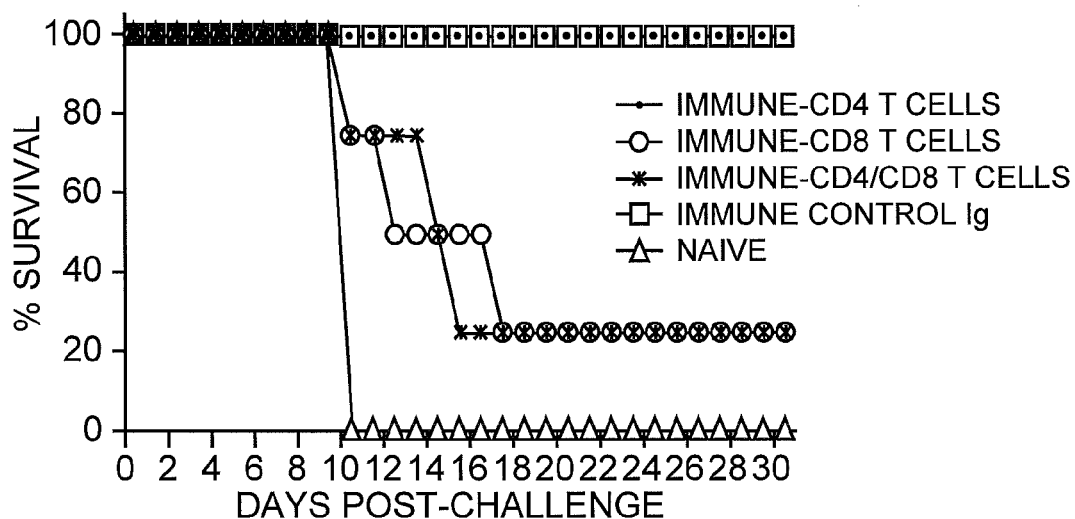
FIG. 2 shows the effect of antibody depletion of T cells, lack of B cells, and adoptive transfer of immune cells on survival against lethal challenge. C57Bl/6 wild-type and μMT mice were immunized following an established protocol. One month after final immunization, wild-type mice were treated with either control Ig or antibody specific for CD4, CD8, or both CD4 and CD8 (FIG. 2A).
FIG. 2B, both immunized and unimmunized μMT mice were left untreated, simultaneously challenged with $10^3$ RH parasites i.p. and percent survival was measured.
FIG. 2C, C57Bl/6 mice were immunized as described above, then three weeks post-final immunization whole splenocytes, CD19$^+$ and CD8$^+$ splenocytes were harvested and either $4 \times 10^7$ whole splenocytes, $1 \times 10^7$ CD8$^+$ T cells, or $5 \times 10^6$ CD19$^+$ B cells were transferred to naïve recipient mice. Twenty-four hours after transfer mice were challenged with $10^3$ RH parasites and monitored for survival. All experiments were performed with n=4 per group and repeated twice with similar results. The data are representative of the two experiments with similar results.
Figure 2B:
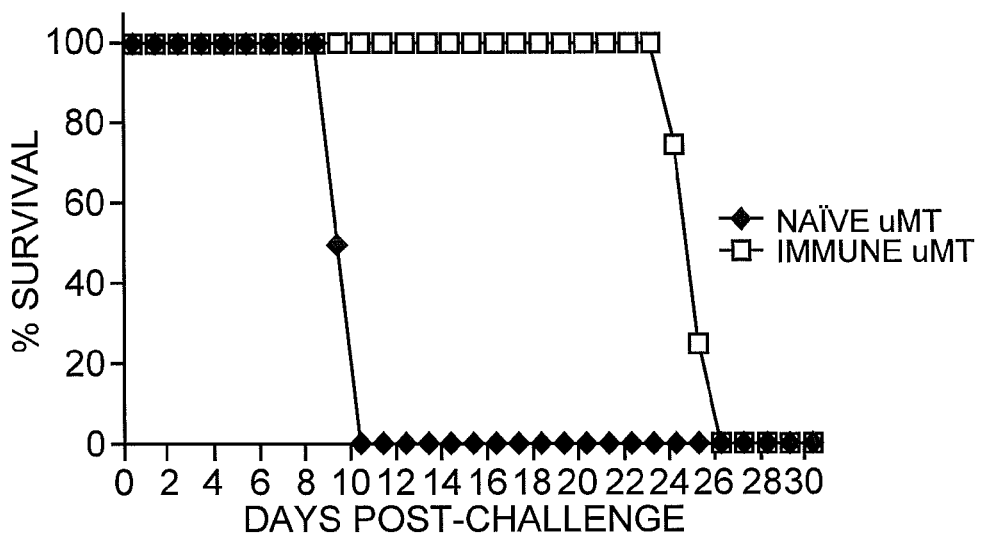

The Potent Long Lasting Protective Immune Response Elicited by Immunization with Live Attenuated cps1-1 Vaccine is Primarily CD8+ T Cell-Mediated and Can Be Adoptively Transferred. The paradigm of a Th-1 inflammatory response inducing cell-mediated immunity providing long term protection involving both CD8+ and CD4+ T cells for resistance to active T. gondii infection is well-established (Suzuki and Remington (1988) J. Immunol. 140:3943-3946; Gazzinelli, et al. (1991) J. Immunol. 146:286-292). Although during the innate response NK cells may play a role in controlling the initial parasite infection, the primary effector cell population responsible for the adaptive cell-mediated protective response is CD8+ T cells (Subauste, et al. (1991) J. Immunol. 147:3955-3959; Hakim, et al. (1991) J. Immunol. 147:2310-2316). To determine whether CD8+ T cells are the primary effector cells responsible for the adaptive immune response after i.p. immunization with cps1-1, antibody depletion of specific T cell populations from immunized mice was used and survival of T cell-depleted mice was measured against lethal challenge. As a control for determining if T cells are the primary effector arm of adaptive immunity responsible for long lasting protection in the present vaccine model, B cell-deficient (µMT) mice were also immunized to assess whether B cells are required for immune responses leading to protective immunity. Wild-type C57Bl/6 and µMT mice were immunized i.p. with cps1-1. C57Bl/6 mice were then antibody depleted of either CD8+ T cells, CD4+ T cells, or both CD4+ and CD8+ T cells whereas µMT mice were not treated. All immunized mice were high dose challenged with $1 \times 10^3$ RH tachyzoites i.p. and monitored for survival. It was observed that 100% of CD4+ T cell-depleted mice survived whereas only 25% of either CD8+- or CD8+/CD4+-depleted mice survived the challenge infection (FIG. 2A) Although cps1-1 immunized µMT mice survived longer than non-immunized naïve µMT mice, all immunized µMT mice succumbed to infection by day 27 post-challenge (FIG. 2B). This result indicates that B cells may adopt a subordinate role as effector cells via antibody production, or that during host response to immunization a deficiency occurs in the development of an effective memory CD8+ T cell population leading to a less potent protective response (Sayles, et al. (2000) Infect. Immun. 68:1026-1033; Langhorne, et al. (1998) Proc Natl. Acad. Sci. USA 95:1730-1734; Matter, et al. (2005) Eur. J. Immunol. 35:3229-3239). These results demonstrate that CD8+ T cells are the main effector cell involved in the protective immunity induced by immunization with cps1-1.

Figure 2C:
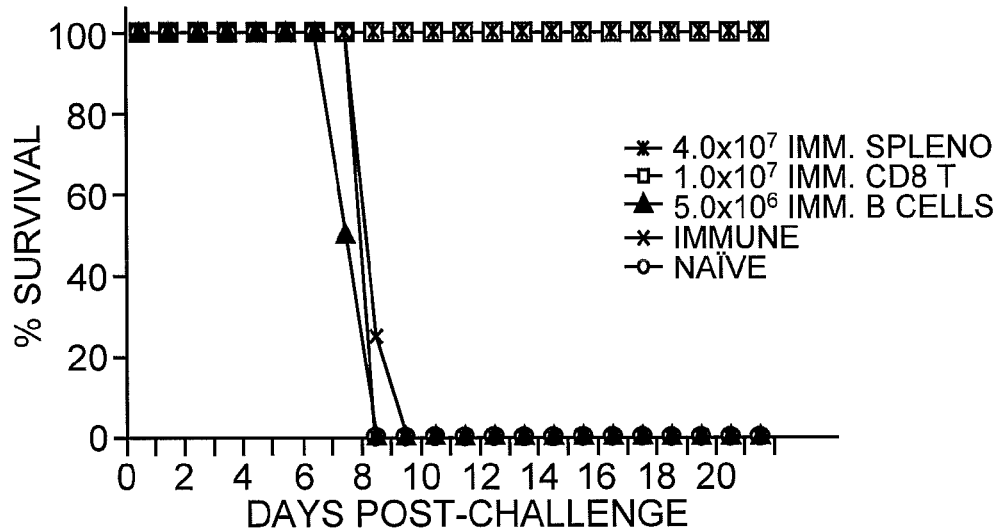

Adoptive transfer was also carried out to confirm that CD8+ T cells were the primary effector mechanism against T gondii infection that develop in response to immunization with cps1-1. Splenocytes were harvested 30 days after cps1-1 immunization and purified CD8+ T cells, B cells, or whole splenocytes were adoptively transferred into naïve recipients. Recipient naïve mice were then challenged with $1 \times 10^3$ RH tachyzoites and percent survival was monitored. Mice receiving $1 \times 10^7$ whole splenocyte-derived cells or $5 \times 10^6$ B cells succumbed to infection by day 10 post-challenge. In contrast, all naïve mice receiving $1 \times 10^7$ purified CD8+ T cells or $4 \times 10^7$ whole spleen cells survived challenge infection (FIG. 2C). These results confirm that T. gondii-specific CD8+ T cells induced by immunization with cps1-1 are the primary effector cells required for adaptive immunity and long lasting protective immunity.

IgG2a is Present in Serum from cps1-1 Immunized Mice Indicative of a Th-1 Immune Response. Specific antibody subclasses are one indicator of the type of T helper cell response induced by infection. A T helper type I cell-biased population induces the production of the immunoglobulin subclass IgG2a (Snapper & Paul (1987) Science 236:944-947; Sornasse, et al. (1992) J. Exp. Med. 175:15-21). Infection with virulent T gondii parasites, as well as immunization with an attenuated temperature sensitive mutant (ts-4) or DCs pulsed with T. gondii antigens, result in IgG positive serum titers that predominantly include the IgG2a subclass (Bourguin, et al. (1998) supra; Waldeland, et al. (1983) J. Parasitol. 69:171-175; Johnson & Sayles (2002) Infect. Immun. 70:185-191). C57Bl/6 mice were immunized with cps1-1 and sera were collected four weeks after the final immunization and examined for titers of whole IgG, IgG1 and IgG2a. Anti-toxoplasma serum titers of total IgG and subclasses IgG1 and IgG2a were nearly equivalent (Table 1). These results for serum IgG titers were similar to those previously reported in response to immunization with ts-4 (Waldeland, et al. (1983) supra). The presence of significant levels of IgG2a in sera from cps1-1 immunized mice indicates the induction of a Th-1-biased T helper cell response.

TABLE 1

| IgG | Mean Titer | SEM | Mean A450 | SEM |
| --- | --- | --- | --- | --- |
| IgG H + L | 14103.8 | 781.8 | 0.546 | 0.011 |
| IgG1 | 12020.3 | 2921.9 | 0.095 | 0.009 |
| IgG2a | 13616.1 | 1126.3 | 0.398 | 0.027 |

Titers were calculated via dilution at which samples from immunized mice were equivalent to unimmunized control sera. Absorbance at 450 nm was recorded for 1:100 dilutions. All experiments were performed with n=4 mice per group. The data are representative of two experiments with similar results and indicate the mean±SEM.

Figure 3A:
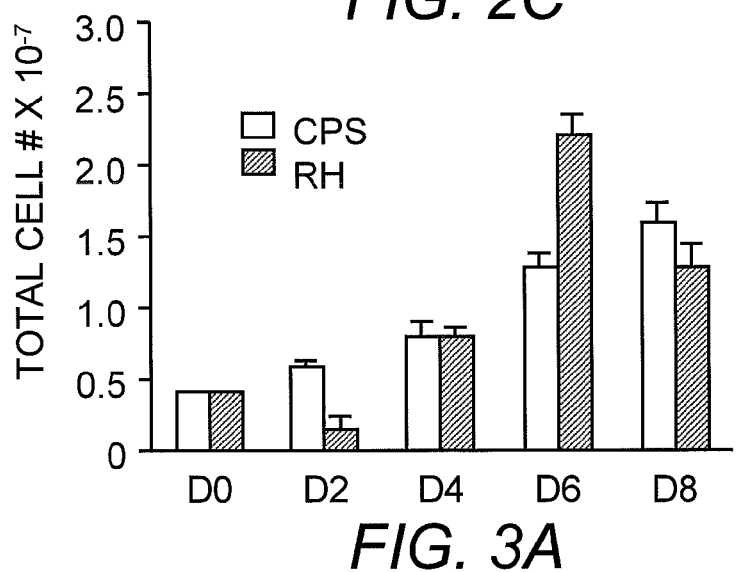
FIG. 3A, total PECs were analyzed by flow cytometry and total cell numbers recovered are presented.

Inflammatory Cell Infiltrate Response to cps1-1, in the Absence of Replication and Growth Associated Host Tissue Destruction is Faster and Less Potent Than Response to RH Infection. During *T gondii* infection, inflammatory cells infiltrate into the site of infection, indicate the type and magnitude of an immune response, and potentially relevant mechanisms in directly or indirectly controlling the infection (Bennouna, et al. (2003) *J. Immunol.* 171:6052-6058; Mordue & Sibley (2003) *J. Leukoc. Biol.* 74:1015-1025; Kelly, et al. (2005) *Infect. Immun.* 73:617-621; Robben, et al. (2005) *J. Exp. Med.* 201:1761-1769; Scharton-Kersten, et al. (1996) *J. Immunol.* 157:4045-4054). Knowledge regarding inflammation, such as cellular infiltrates in response to *T gondii* infection, has been elucidated with replication-competent strains that induce extensive growth-associated host tissue destruction (Scharton-Kersten, et al. (1996) *Exp. Parasitol.* 84:102-114; Gavrilescu, et al. (2001) *J. Immunol.* 167:902-909). Therefore, the magnitude and kinetics of inflammatory cell infiltrates was examined in the absence of parasite replication-associated host tissue destruction after immunization with cps1-1. For comparison, the inflammatory cell infiltrate response to RH infection, which causes significant levels of replication associated host tissue destruction, was measured. C57BL/6 mice were inoculated i.p. with either $1\times10^6$ cps1-1 or $1\times10^3$ RH tachyzoites intraperitoneally, and total PECs were isolated on days 0, 2, 4, 6, and 8 post-inoculation as described herein and enumerated (FIG. 3A). A significant ($p=0.005$) increase in cell numbers occurred by Day 2 post-cps1-1 inoculation followed by a steady and 3-fold significant increase ($p=0.0001$) by Day 6 and Day 8 as compared to Day 0 naïve controls (FIG. 3A). In contrast, RH infection induced an unexpected significant decrease ($p=0.024$) in total PEC numbers on Day 2 post-infection (FIG. 3A). This decrease in cell number was quickly resolved by Day 4 and the highest cell numbers were seen by Day 6 then declined by Day 8 post-infection, most likely due to significant necrosis and tissue destruction. The overall magnitude of inflammatory cell infiltrate into the site of infection was greater during RH infection than with cps1-1 immunization. While the level of cellular infiltrate was significantly greater at Day 2 post-infection with cps1-1 ($p=0.003$) than with RH infection, this was reversed by Day 6 post-infection, where RH PECs were 1.5-fold greater ($p=0.002$) than seen in cps1-1-treated mice. Total cell numbers of PECs measured at Day 8 were not significantly different between RH and cps1-1. These results reveal that i.p. inflammatory cellular infiltrate response to cps1-1 was earlier than with RH, indicating an inactivation or inhibition of the early innate immune response induced by the rapidly replicating RH parasite allowing it to gain a foothold and contribute to its lethal virulence. Moreover, the overall level of PEC infiltrate in response to cps1-1 inoculation was significantly lower than RH infection, indicating that replication-associated host tissue destruction contributed to the magnitude of the inflammatory response.

Recruitment of Specific Inflammatory Cells into the Site of Infection Occurs Earlier and is Less Potent in the Absence of Rapid Replication and Growth-Associated Host Tissue Destruction. As inflammatory cell types such as granulocytes (PMNs), macrophages, and B and T lymphocytes are important for the development of protective immunity and for direct control of primary *T. gondii* infection, it was of significant interest to investigate the absolute numbers and percent composition of the specific cell types contained in PECs infiltrating in response to the protective cps1-1 vaccine compared to virulent (RH) infection to examine which cell populations contribute to the control and development of long term protective immunity in the absence of rapid replication and growth-associated host tissue destruction (Mordue & Sibley (2003) *J. Leukoc. Biol.* 74:1015-1025; Scharton-Kersten, et al. (1996) *J. Immunol.* 157:4045-4054; Bliss, et al. (2000) *J. Immunol.* 165:4515-4521). Initial flow cytometric analysis of total PECs identified three general cell populations when using forward scatter (FSC) and side scatter (SSC) analyses. $FSC^{low}\ SSC^{low}$ were classified as lymphocytes (gate R1), $FSC^{high}\ SSC^{low-mid}$ were classified as macrophages/monocytes (gate R2), and $FSC^{mid}\ SSC^{high}$ were classified as granulocytes/neutrophils (gate R3) (Bliss, et al. (2000) *J. Immunol.* 165:4515-4521; Schleicher, et al. (2005) *Blood* 105:1319-1328; Henderson, et al. (2003) *Blood* 102:328-335). Based on these criteria three individual gates were drawn to isolate each region for analysis and whose sum of data were verified and found to be equivalent to results of total events.

Figure 3B:
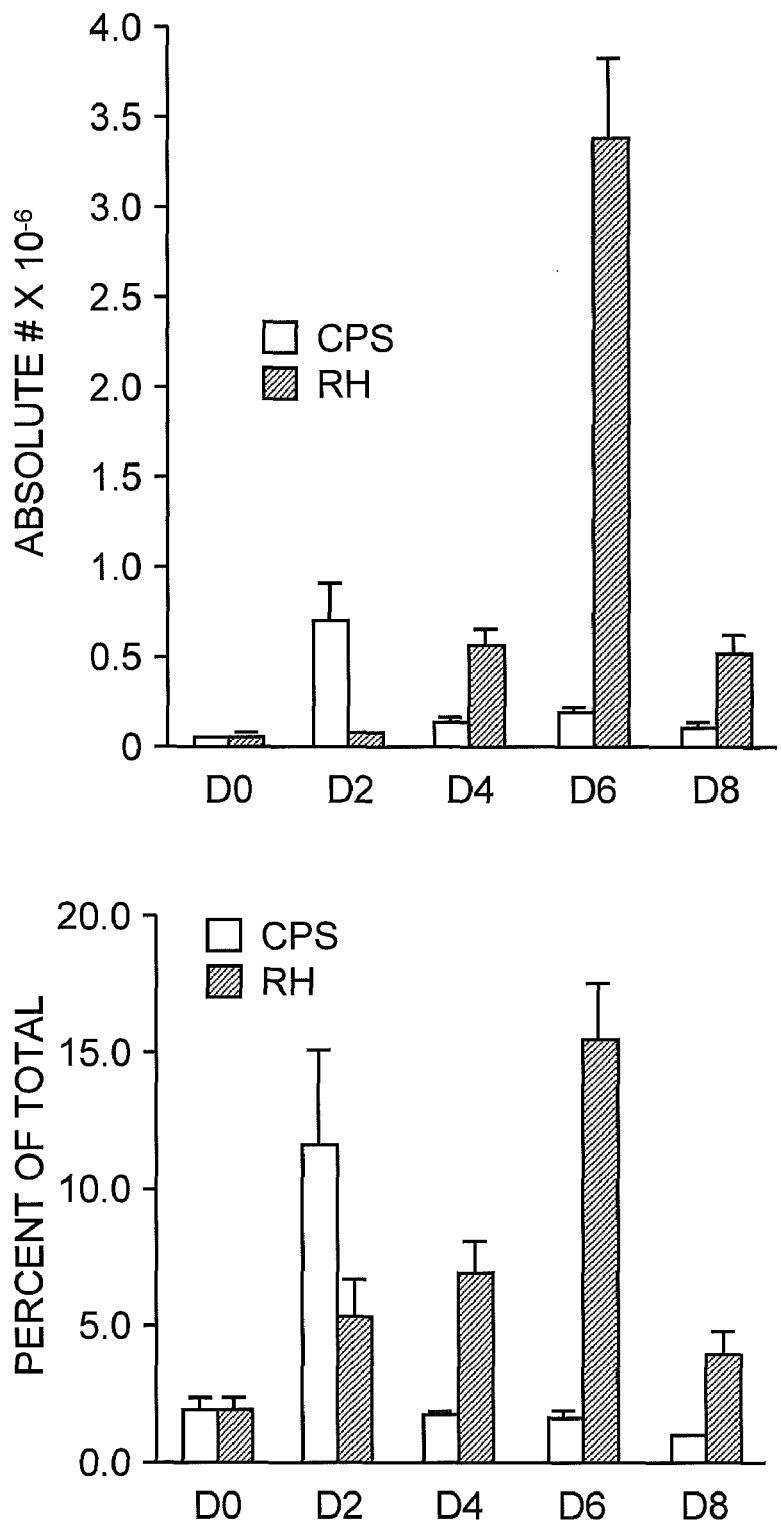

Granulocytes. Granulocytes are rapid responders and quickly infiltrate after *T. gondii* infection. These cells are required for early control of infection and are an early source of IL-12, which may set the stage for a Th-1-skewed response and early IFN-γ production (Bliss, et al. (2000) *J. Immunol.* 165:4515-4521; Khan, et al. (2001) *J. Immunol.* 166:1930-1937; Bliss, et al. (2001) *Infect. Immun.* 69:4898-4905; Del Rio, et al. (2001) *J. Immunol.* 167:6503-6509). To carry out this analysis, a double stain of Gr-1 and CD68 was used and the percent of total events in the granulocyte (R3) region were measured. The results from R3 were confirmed by back-gating from all three gates for Gr-1$^+$ CD68$^-$ cells and by staining for Gr-1 alone. From this analysis it was determined that R3 contained ≧95% of the granulocytes detected (Bliss, et al. (2000) *J. Immunol.* 165:4515-4521). After cps1-1 vaccination i.p. a significant 9-fold increase in the absolute number of granulocytes ($p=0.026$) was observed by Day 2 post-inoculation. After Day 2 the total numbers of granulocytes returned to uninfected control levels (FIG. 3B, upper panel). When the percent of Gr-1$^+$ CD68$^-$ cells in total events was measured, the identical pattern of granulocyte infiltration was observed with a significant increase by Day 2 post-infection ($p=0.033$) from 1.8% to 11.5% followed by a decrease to 1.6% by Day 4 (FIG. 3B, lower panel). In contrast to cps1-1, the absolute numbers of granulocytes responding to RH infection did not significantly increase until Day 4 where a 6.8-fold increase ($p=0.001$) over Day 0 was measured. This increase in granulocyte numbers continued through Day 6 with a 6.0-fold increase over Day 4 ($p=0.001$) followed by a significant reduction at Day 8 ($p=0.001$) (FIG. 3B, upper panel). This pattern was also observed in terms of the percent of total infiltrating cells being granulocytes, wherein at Day 2 post-infection 5.2% of the total cells were granulocytes, at Day 6 post-infection 15.3% of the total cells were granulocytes, and at Day 8 a 4-fold decrease was observed (FIG. 3C, lower panel). Recruitment of granulocytes after cps1-1 vaccination occurred more rapidly (peak by Day 2) as compared to RH infection (peak by Day 6) as indicated by both absolute numbers and percentages of total events (FIG. 3B). After Day 2, RH infection induced significantly greater granulocyte infiltration than did cps1-1 vaccination and these differences may have been due to a difference in initial antigen load, a delay in granulocyte infiltration by virulent RH infection, or granulocyte infiltration in response to RH infection associated host tissue destruction.

Macrophages. The level and kinetics of macrophage infiltration after infection with RH or vaccination with cps1-1 was also determined. Macrophages encompass the greatest percentage of resident PECs (~50%) in the uninfected steady state (FIG. 3C). There is evidence that macrophages are preferentially targeted for invasion by *T. gondii*. Either Gr-1$^+$ or Gr-1$^-$ macrophages respond to infection, provide a host cell environment amenable to parasite growth and replication, and provide a first line of host defense (Mordue & Sibley (2003) *J. Leukoc. Biol.* 74:1015-1025; Robben, et al. (2005)

*J. Exp. Med.* 201:17611769). To measure the absolute number and percent of macrophages in total PECs, an intracellular stain for CD68 or macrosialin was employed. In addition to CD68, PECs were also stained with the surface marker Gr-1 to detect the *T. gondii*-specific double-positive staining Gr-1$^+$ CD68$^+$ inflammatory macrophage population. The absolute numbers of CD68$^+$ macrophages infiltrating into the peritoneum with cps1-1 vaccination significantly increased 1.5-fold (p<0.001) by Day 4 post-inoculation compared to Day 0 (FIG. 3C, upper panel). The maximum number of CD68$^+$ cells had infiltrated by Day 6 with a 2.1-fold increase (p=0.001) in absolute numbers over Day 0 controls. This population remained present at Day 8 post-infection with no significant change. When this pattern of influx was analyzed as a percent of total PECs, it was observed that the percentage of CD68$^+$ cells did not significantly change until Day 6 and Day 8, where unexpectedly CD68$^+$ cell numbers decreased (p=0.011) compared to Day 0 (FIG. 3C, lower panel). Although absolute numbers of CD68$^+$ macrophages increased with time in both RH infection and cps1-1 immunization, other cell populations were infiltrating at a more rapid rate by Day 6 post-inoculation.

CD68$^+$ Gr-1$^+$ Macrophages. Analysis was also carried out to determine the absolute number and percentage of the total PECs that were Gr-1$^+$ CD68$^+$ inflammatory macrophages infiltrating into the site of inoculation. At Day 0, or in uninfected naïve controls, less than 1% of the CD68$^+$ cells were also Gr-1$^+$ (FIG. 3D). When mice were immunized i.p. with cps1-1, a significant 168-fold increase (p<0.001) in the absolute numbers of Gr-1$^+$ CD68$^+$ cells was observed by Day 2 post-infection (FIG. 3D, upper panel). A significant 2.5-fold decrease (p<0.001) in the numbers of Gr-1$^+$ CD68$^+$ macrophages at Day 4 post-inoculation was then observed. It was surprising to also observe a second population or wave of Gr-1$^+$ CD68$^+$ macrophages infiltrating into the site of cps1-1 inoculation at Day 6, wherein a significant 2.5-fold increase (p=0.002) in absolute cell number (compared to Day 4 and Day 6) was observed, which was then followed by a significant 3.8-fold decrease (p=0.004) in the number of inflammatory macrophages by Day 8 post-vaccination (compared to Day 6 and Day 8). This analysis of the percent of total PECs identified as Gr-1$^+$ CD68$^+$ inflammatory macrophages over the course of inoculation with cps1-1 followed the pattern observed for absolute numbers (FIG. 3D, lower panel). In contrast, the percentage of CD68$^+$ macrophages decreased between Day 0 and Day 8 (FIG. 3C, lower panel). These observations indicate that of the CD68$^+$ resident macrophages that are present in the peritoneum at Day 0, >99% have been replaced by the *T. gondii*-specific inflammatory Gr-1$^+$ CD68$^+$ macrophages by Day 2 post-inoculation. Not wishing to be bound by theory, this is most likely due to infiltration of new Gr-1$^+$ CD68$^+$ inflammatory macrophages because in vitro infection of peritoneal-derived macrophages with cps1-1 under replicating or non-replicating conditions in uracil does not result in the expression of Gr-1. By Day 4 post-inoculation many of these Gr-1$^+$ CD68$^+$ inflammatory macrophages are cleared down to 27.5% of all CD68$^+$ macrophages. By Day 6 post-inoculation, 68% of the CD68$^+$ macrophages are Gr-1$^+$ CD68$^+$ followed by a decrease to 14.8% of all CD68$^+$ cells by Day 8 post-inoculation (Mordue & Sibley (2003) *J. Leukoc. Biol.* 74:1015-1025; Robben, et al. (2005) *J. Exp. Med.* 201:17611769).

In contrast to non-replicating cps1-1 vaccine, the total CD68$^+$ macrophages decreased 4-fold (p<0.001) by Day 2 post-active RH infection when compared to Day 0 (FIG. 3C, upper panel). The number of CD68$^+$ macrophages then increase significantly 7-fold (p<0.001) by Day 4 post-infection compared to Day 2. By Day 6 post-infection with RH, CD68$^+$ cells had increased 2-fold (p=0.032) over Day 4 and reached their highest absolute numbers at this time. By Day 8 post-infection absolute numbers of CD68$^+$ macrophages remained elevated but are not significantly lower (p=0.093) than Day 6 post-infection. A similar pattern of CD68$^+$ macrophages as a percent of total PECs after RH or cps1-1 inoculation was observed, indicating that CD68$^+$ macrophages were recruited at the same rate regardless of replicating (RH) or non-replicating (cps1-1) parasites. Other cells types were being recruited more rapidly to the site of parasite inoculation.

When the PECs were analyzed for the absolute numbers of *T. gondii*-specific Gr-1$^+$ CD68$^+$ inflammatory macrophages during RH infection, a delay in the recruitment of these cells to the site of RH infection was observed, i.e., cells were only observed at Day 4. By Day 6, the Gr-1$^+$ CD68$^+$ cells had significantly increased 2-fold (p=0.041) over Day 4. The absolute numbers of Gr-1$^+$ CD68$^+$ cells did not significantly change between Day 6 and Day 8. The analysis of the Gr-1$^+$ CD68$^+$ percent composition of the total events in response to RH infection revealed a similar, but delayed pattern to that observed for cps1-1 vaccination. Upon further analysis, a similar ratio of macrophage cell types infiltrating during infection with RH was not observed as compared to cps1-1 vaccination. By Day 4 and through Day 8 post-RH infection, Gr-1$^+$ CD68$^+$ macrophages made up greater than 99% of the total CD68$^+$ cells observed to infiltrate during the course of infection, indicating that although there may have been a similar pattern of Gr-1$^+$ CD68$^+$ entering and leaving the site of infection, there was a lack of balance between normal CD68$^+$ activated or non-activated resident peritoneal macrophages with the activated inflammatory *T. gondii*-specific Gr-1$^+$ CD68$^+$ macrophages. This imbalance could have been in part due to the inflammatory contribution caused by virulent RH infection associated host cell and tissue destruction.

Figure 3E:
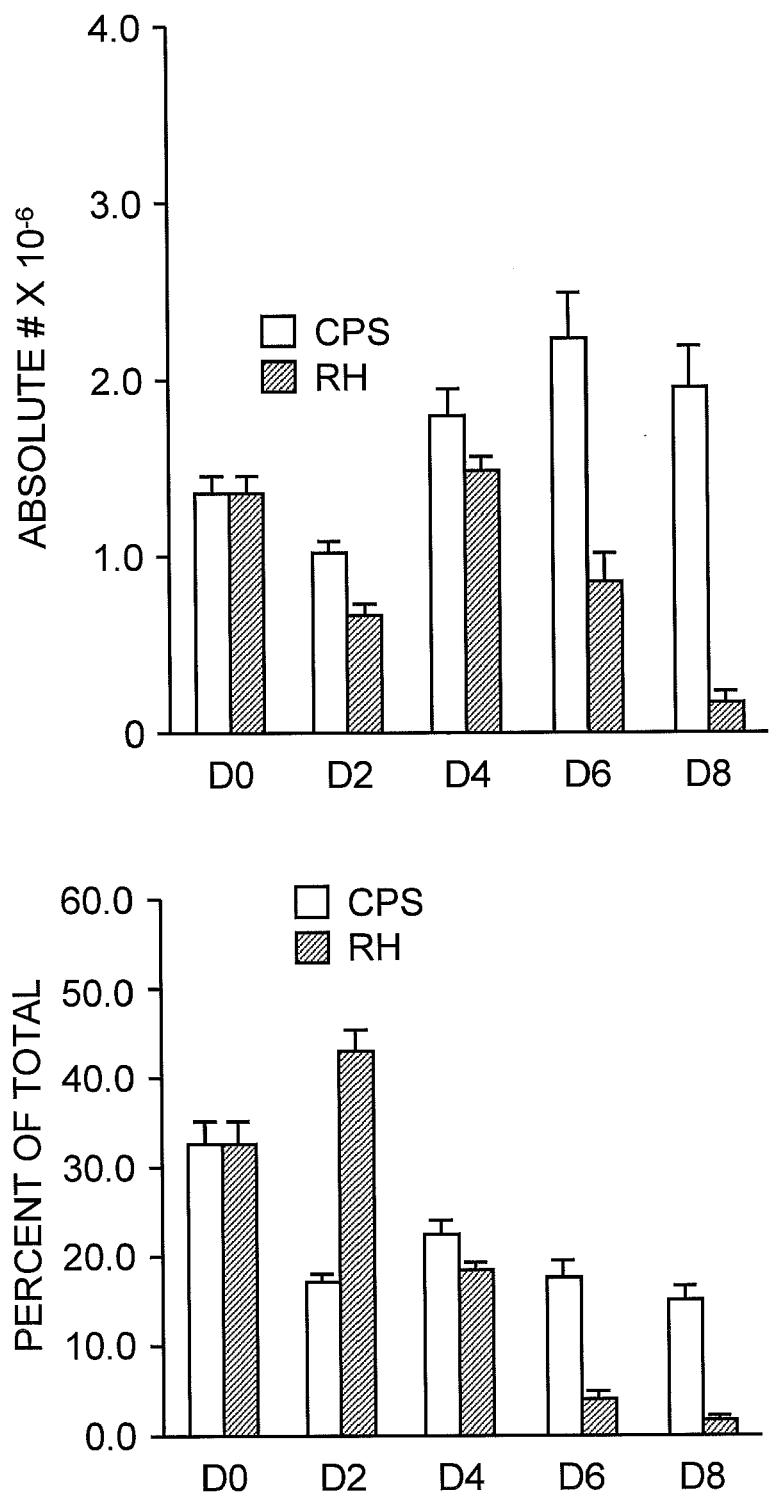

B cells. B lymphocytes play a role in mediating the outcome of infection with *T. gondii* because cps1-1 vaccinated µMT mice showed a delayed time to death phenotype, but uniformly did not survive a high lethal dose RH challenge (FIG. 2B). Whether this role was significant for anti-toxoplasma antibody production or enhancing memory CD8$^+$ T cell responses remains under investigation (Sayles, et al. (2000) *Infect. Immun.* 68:1026-1033; Langhorne, et al. (1998) *Proc. Natl. Acad. Sci. USA* 95:1730-1734; Johnson, et al. (2002) *Infect. Immun.* 70:185-191). Accordingly, cell-specific differences in the host inflammatory cell infiltrate response to cps1-1 vaccination or RH infection was analyzed by measuring the absolute numbers and percentage of total PECs that were CD19$^+$ B cells. Unexpectedly, 2 days after cps1-1 inoculation a significant decrease (p=0.022) in the absolute numbers (30% decrease) from naïve controls was observed (FIG. 3E, upper panel). This was followed by a significant increase in CD19$^+$ B cell numbers at Day 4 (1.8-fold) and Day 6 (2-fold) with p-values equal to 0.001 and 0.003, respectively. The absolute numbers of CD19$^+$ B cells then remained steady through Day 8 post-inoculation. When the percent of CD19$^+$ B cells contained in total PECs after cps1-1 vaccination was assessed, 32.5% of the total PECS were CD19$^+$ B cells at Day 0 (FIG. 3E, lower panel). The percentage then significantly decreased 1.9-fold to 17.2% of the total PECs, and did not significantly change through Day 8. Analysis of PECs after RH infection revealed that while the absolute numbers of CD19$^+$ B cells followed a similar pattern as with cps1-1 inoculation only until Day 4, RH infection induced a significant 2-fold decrease (p=0.012) in CD19$^+$ B cells by Day 6. This clearance of the CD19$^+$ B cells markedly accelerated through Day 8 post-RH infection. When the percent of $CD19^+$ B cells in the total number of events was measured, it was observed that the percentage of B cells in PECs in response to RH infection significantly increased (p=0.018) by Day 2 post-infection from 32.5% to 42.9% of the total (FIG. 3E, lower panel). However, by Day 4 post-infection, the percentage of B cells had significantly decreased 2.2-fold (p<0.001) below Day 0 naïve controls. By Day 6 and Day 8 post-RH infection, the percent of $CD19^+$ B cells was reduced 14-fold and 35-fold, respectively, compared to Day 0 (FIG. 3E, lower panel). The retention or continual recruitment of $CD19^+$ B cells during cps1-1 vaccination could be an important component in the development of $CD8^+$ T cell memory through enhanced co-stimulation, antigen presentation, or by acting in an innate function if the $CD19^+$ B cells were proportionally higher for B1 B cells over B2 B cells.

T cells. Resolution of infection by *T. gondii* requires a potent $CD8^+$ T cell response. A synergistic role of both $CD4^+$ and $CD8^+$ T cells is required to develop this cell mediated protection (Snzuki & Remington (1988) *J. Immunol.* 140: 3943-3946; Gazzinelli, et al. (1991) *J. Immunol.* 146:286-292; Subauste, et al. (1991) *J. Immunol.* 147:3955-3959). Due to the key role that both $CD4^+$ and $CD8^+$ T cells play in the outcome of *T. gondii* infection and development of protective immunity, the kinetics of cell infiltration to the site of inoculation was analyzed by measuring the absolute number and percent of the total PECs that were T cells ($CD3^+$) and how many of those T cells were $CD3^+$ $CD4^+$ or $CD3^+$ $CD8^+$ over the course of RH infection compared to cps1-1 vaccination. This analysis indicated that, when measuring CD3 alone, the absolute number of T lymphocytes infiltrating to the site of cps1-1 inoculation significantly increased 1.9-fold (P=0.022) by Day 2 post-infection (FIG. 3F, upper panel). The increase in absolute numbers of $CD3^+$ T cells continued to Day 4 and Day 6 post-infection with 4- and 11-fold increases, respectively, over Day 0. $CD3^+$ T cells were at their highest number at Day 8 post-cps1-1 inoculation. The same pattern was observed when measuring the percent of $CD3^+$ T cells in total PECs, wherein at Day 0 that there were less than 10% T lymphocytes, but by Day 4 post-infection this amount increased to 18.7% and at Day 6 and Day 8 the percent increased to 33.7% and 34.3%, respectively, of total PECs (FIG. 3F, lower panel). In contrast to cps1-1 vaccination, RH infection delayed an increase in total $CD3^+$ T cells until Day 4 post-infection, a 1.8-fold increase was observed (FIG. 3F, upper panel). The highest numbers of $CD3^+$ T cells were present by Day 6 which was then followed by a decrease in number at Day 8. The absolute numbers of T cells infiltrating into the site of infection were significantly lower (P=0.004, p<0.001, p<0.001, p<0.001) in response to RH infection than with cps1-1 vaccination for each time point beginning at Day 2 post-inoculation. When measuring the percent of $CD3^+$ T cells of total PECs, it was observed that only at Day 2 was there a significant increase (P=0.035) in the percentage of total T cells after RH infection (FIG. 3F, lower panel). Soon after this peak at Day 2 post-RH infection, the percentage of $CD3^+$ T cells decreased back to Day 0 levels. Overall the recruitment of $CD3^+$ T cells by the host in response to cps1-1 inoculation was very robust and the presence of significant RH replication and growth-associated host tissue destruction may severely restrict $CD3^+$ T cell recruitment.

As both $CD4^+$ and $CD8^+$ T cells play a role in controlling *T. gondii* infection, the kinetics and numbers of either $CD4^+$ or $CD8^+$ T cells infiltrating into the site of inoculation was analyzed. The $CD3^+$ T cell analysis was extended to include cells that would stain double-positive for either $CD3^+$ $CD4^+$ or $CD3^+$ $CD8^+$. It was observed that after cps1-1 vaccination, both $CD4^+$ and $CD8^+$ T cell numbers increased significantly (p=0.029 and 0.007, respectively) 1.7- and 2.8-fold, respectively, by Day 2 post-infection (FIG. 3G, upper panel). Both $CD4^+$ and $CD8^+$ T cell numbers increased continuously over time and reached maximal numbers by Day 8 post-infection with absolute numbers of $CD4^+$ T cells significantly greater than $CD8^+$ T cells from Day 6 through Day 8 (p<0.001). However, when the different T cell populations were analyze as percentage of total PECs, the percent of $CD3^+$ $CD8^+$ T cells was found to increase significantly (p=0.03) early by Day 2 post-inoculation (FIG. 3G, lower panel). The $CD3^+$ $CD4^+$ T cell population did not significantly increase in percentage until Day 4 as compared to Day 0 (p=0.01), indicating that $CD8^+$ T cells infiltrated earlier in response to cps1-1 vaccination than the $CD4^+$ T cells. In contrast to vaccination with cps1-1, the absolute numbers of either $CD4^+$ or $CD8^+$ T cells in response to RH infection did not significantly increase until Day 4 post-infection with $CD4^+$ T cells undergoing 1.4-fold and $CD8^+$ T cells undergoing 2.3-fold increases (FIG. 3H, upper panel). Maximal increases in absolute numbers of both $CD4^+$ and $CD8^+$ T cells occurred by Day 6 post-RH infection followed by an acute and significant reduction (p=0.001 CD4; p=0.001 CD8) by Day 8 post-infection. There was no significant differences in absolute numbers between either T cell type, unlike the response to cps1-1 vaccination (compare FIGS. 3G and 3H). Percent of total event analysis revealed that only $CD4^+$ T cells significantly increased at Day 2 post-RH infection (p=0.01), while $CD8^+$ T cells did not significantly change as a percentage of total PECs for the entire course of infection (FIG. 3H, lower panel). The initial increase in the percent of $CD4^+$ T cells in the total PEC population was reversed by Day 4 with a significant decrease (p=0.001) to below Day 0 levels. These results indicate that $CD8^+$ T cells respond more rapidly than $CD4^+$ T cells to vaccination with cps1-1. However, $CD4^+$ T cells eventually infiltrate in greater numbers (and percentages) over $CD8^+$ T cells by Day 6 and Day 8 after cps1-1 vaccination. Despite a robustly enhanced level of cellular infiltration by Day 6 in the context of RH replication and growth-associated host tissue destruction (FIG. 3A), both $CD4^+$ and $CD8^+$ T lymphocytes were significantly impaired in their ability to infiltrate into the site of RH infection (FIG. 3H).

The Attenuated Type I cps1-1 Vaccine Induces Early Systemic Production of IFN-γ, IL-12p40 and IL-12p70. Previous studies establish that infections with viable and replicating *T. gondii* parasites induce potent Th-1-biased inflammatory responses highlighted by high-level production of IFN-γ and variable levels of IL-12p70 production depending on parasite genotype (Type I, II, II) (Scharton-Kersten, et al. (1996) *Exp. Parasitol.* 84:102-114; Robben, et al. (2004) *J. Immunol.* 172:3686-3694; Scharton-Kersten, et al. (1996) *J. Immunol.* 157:4045-4054). In contrast, studies utilizing replicating parasites are confounded by extensive infection-associated host tissue destruction from parasite replication and growth and the resulting tissue destruction may enhance the overproduction of potentially lethal inflammatory cytokines (Gavrilescu & Denkers (2001) *J. Immunol.* 167:902-909). Accordingly, systemic levels of pro-inflammatory Th-1 cytokines were measured in sera at Day 0, 2, 4, 6, and 8 post-inoculation of cps1-1-vaccinated mice. In this regard, cytokine produced solely in response to this attenuated Type I parasite could be measured in the absence of growth and replication-associated host tissue destruction and compared to C57B1/6 mice that were infected with the virulent parental Type I strain RH. The production of IL-12p40, IL-12p70, and IFN-γ was measured by ELISA.

Figure 4A:
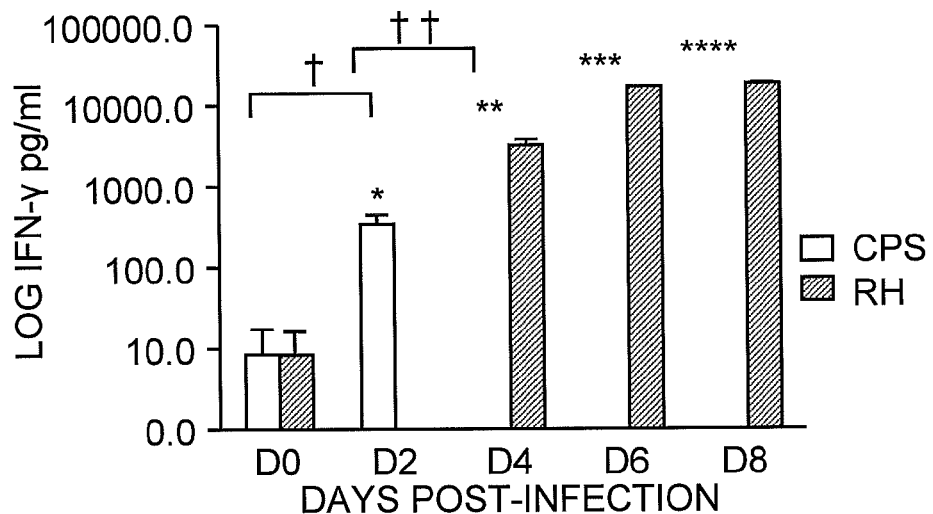
FIG. 4A, p=*0.03, 0.001, *0.0001, ****0.0001, $^\dagger$0.03, $^{\dagger\dagger}$0.0001.

Systemic IFN-γ and IL-12p40 in serum of mice infected with RH did not significantly increase until Day 4 post-infection and quickly rose to maximum levels by Day 6 and 8. Systemic IFN-γ at Day 0 decreased by Day 2 compared to naïve Day 0 controls (FIG. 4A). Type I RH infection induced exceedingly low levels of systemic IL-12p70 only detectable on Day 2 and Day 4 (FIG. 4B) consistent with previous reports that IL-12p70 production may only be induced by Type II parasite strains (Robben, et al. (2004) *J. Immunol.* 172:3686-3694). Poor IL-12p70 induction in sera of mice was proposed to be one of the reasons Type I parasite infections are universally lethal (Robben, et al. (2004) supra).

Kinetics of production of systemic IFN-γ, IL-12p40, and IL-12p70 after vaccination with the Type I cps1-1 vaccine strain derived from parental RH was completely opposite to that observed with RH infection (FIG. 4). Systemic levels of IFN-γ from mice after cps1-1 vaccination were early ($p=0.03$) at Day 2 post-inoculation (FIG. 4A). This systemic IFN-γ production was transient and was significantly decreased ($p=0.03$) by Day 4 (<10 pg/ml IFN-γ) and remained below detectable levels for the remainder of the 8-day kinetic evaluation.

Figure 4B:
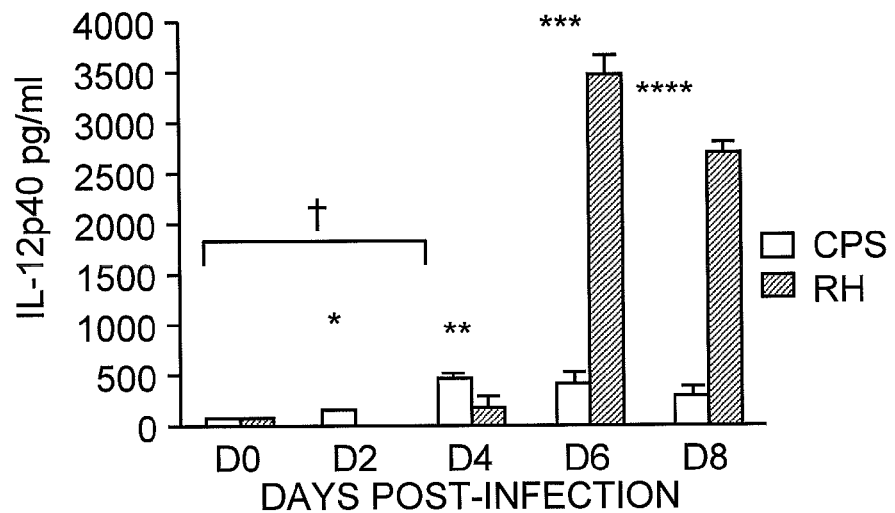
FIG. 4B, p=*0.0001, 0.04, *0.0001, ****0.0001, $^\dagger$0.001.

In contrast to RH infection, induction of systemic IL-12p40 after cps1-1 vaccination was low with a significant systemic increase ($p=0.001$) detected at Day 4 (4-fold increase over Day 0 naïve mice). Levels of IL-12p40 held steady through Day 6 and Day 8 (FIG. 4B). The level of early systemic IL-12p40 production was significantly lower in response to RH infection than cps1-1 vaccination at Day 2 and Day 4 post-infection with p-values equal to 0.0001 and 0.04, respectively.

Figure 4C:
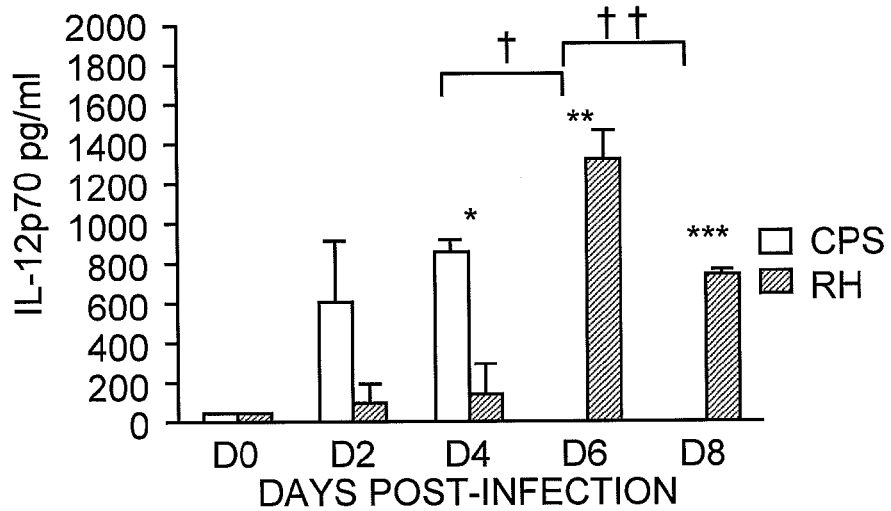
FIG. 4C, p=*0.001, 0.0001, *0.0001, $^\dagger$0.04, $^{\dagger\dagger}$0.02.

Significant systemic IL-12p70 production was induced after vaccination with the Type I attenuated cps1-1 (FIG. 4C). Cps1-1 induced systemic IL-12p70 rapidly by Day 2 post-inoculation over undetectable levels in Day 0 naïve mice. IL-12p70 levels then showed a significant increase ($p=0.036$) by Day 4 with a further increase by Day 6 post-inoculation and a significant decrease by Day 8 ($p=0.015$). When comparing the IL-12p70 production in response to Type I-matched strains, cps1-1 compared to RH, significantly greater amounts ($p=0.0001$) were observed for the time points of Day 4, Day 6, and Day 8 collected from mice infected with cps1-1. This was a remarkable finding because the cps1-1 parasite is an attenuated Type I parasite and production of IL-12p70 has been reported to be suppressed in response to Type I infections (Robben, et al. (2004) supra) (see also FIG. 4C).

Vaccination with cps1-1 induced more rapid systemic production of IFN-γ and Il-12p40 than observed with RH infection. Significant IL-12p70 was produced with cps1-1 vaccination but not in RH infection. It has been reported that an immune evasion may be occurring in RH infection leading to a loss of control of the virulent Type I parasite with systemic overproduction of inflammatory cytokines and lethal pathology (Gavrilescu & Denkers (2001) *J. Immunol.* 167:902-909; Aliberti, et al. (2003) *Nat. Immunol.* 4:485-490). Both IL-12-dependent and -independent IFN-γ production has been shown to be required for the development of long term protective immunity leading to control of the chronic infection (Scharton-Kersten, et al. (1996) *Exp. Parasitol.* 84:102-114). IL-12 dependent IFN-γ production in particular is thought to be required for the development of long lasting protection (Gazzinelli, et al. (1994) *J. Immunol.* 153:2533-2543). The results presented herein indicate the lack of production of IL12p70 in response to RH would likely add to the inability of the host to directly control the RH infection. As observed during cps1-1 vaccination, IL-12p70 is produced systemically early and maintained, thereby potentially enhancing the overall immune response and leading to the development of more effective long lasting protective immunity.

The Immune Response of IFN-γ, IL-12p40, and IL-12p70 Production is Primarily a Local Response at the Site of cps1-1 Vaccination. As demonstrated herein, a unique pattern of inflammatory cell infiltration occurs during cps1-1 vaccination compared to RH infection. It was important then to measure the kinetics and magnitude of Th-1 cytokine production locally at the site of inoculation and at a peripheral site to ascertain how the local immune response may contribute to control of infection and the development of long lasting immune protection. C57Bl/6 mice were vaccinated i.p. with cps1-1 or infected i.p. with RH, and PECs and splenocytes were harvested at Day 0, Day 2, Day 4, Day 6, and Day 8 post-infection. Harvested PECs and splenocytes were cultured 24 hours at $1\times10^6$ and $5\times10^6$ cells/ml, respectively, and supernatants recovered from individual cell cultures were used for ELISA to measure the production of IFN-γ, IL-12p40, and IL-12p70.

Figure 5A:
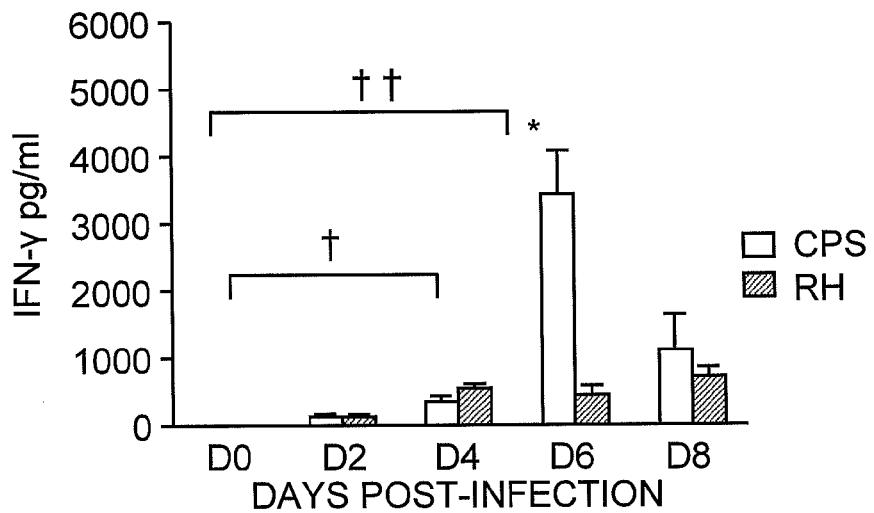
FIG. 5A, p=*0.005, $^\dagger$0.001, $^{\dagger\dagger}$0.04.

PECs from mice infected with RH produced significantly more IFN-γ ($p<0.001$) at Day 4 post-infection than at Day 0 and Day 2 post-infection and remained at a similar level through Day 6 and Day 8 post-infection (FIG. 5A). IL-12p40 (FIG. 5B) was produced by PECs most significantly ($p<0.001$) at Day 4 post-infection (8-fold increase) as compared to Day 0 and Day 2. IL-12p40 levels subsequently decreased at Day 6 and fell below detectable levels by Day 8 post-infection. Moderate but highly variable levels of IL-12p70 were produced by PECs from RH-infected mice beginning on Day 4 then waning on Day 6 and Day 8 (FIG. 5C).

In comparison to PECs, splenocytes from RH-infected mice produced IFN-γ at greater levels than PECs (FIG. 5D) (Mordue & Sibley (2003) *J. Leukoc. Biol.* 74:1015-1025; Gavrilescu & Denkers (2001) *J. Immunol.* 167:902-909). IFN-γ production by splenocytes was not significantly increased until Day 4 post-infection as compared to Day 2 post-infection with a $p=0.001$ and IFN-γ levels increased on Day 6 and again increased by Day 8. When comparing IL-12p40 production between PECs and splenocytes in RH infection (compare FIG. 5B and FIG. 5E), the production of IL-12p40 appeared equivalent or higher in PECs when taking into account total cell number. Splenocytes produced IL-12p40 in a similar pattern to IFN-γ, where a significant increase in production ($p<0.001$) in response to RH infection was observed by Day 4, a further increase by Day 6 post-infection, and subsequent decline (FIG. 5E). Minimal production of IL-12p70 by splenocytes in response to RH infection was observed only on Day 4 and Day 6 post-infection (FIG. 5F).

In the case of cps1-1 vaccination, a novel and primarily local pattern of cytokine production by PEC and splenocyte populations was seen as compared to RH infection (FIG. 5). After cps1-1 vaccination, PEC IFN-γ production was detected by Day 2 and increased to highest levels by Day 6 as compared to Day 2 post-infection ($p=0.04$). Subsequently, IFN-γ levels significantly decreased by Day 8. Unexpectedly, PECs from cps1-1 vaccinated mice produced significantly greater IFN-γ levels than PECs from RH-infected mice by Day 6 post-infection with $p=0.005$ (FIG. 5A).

Figure 5B:
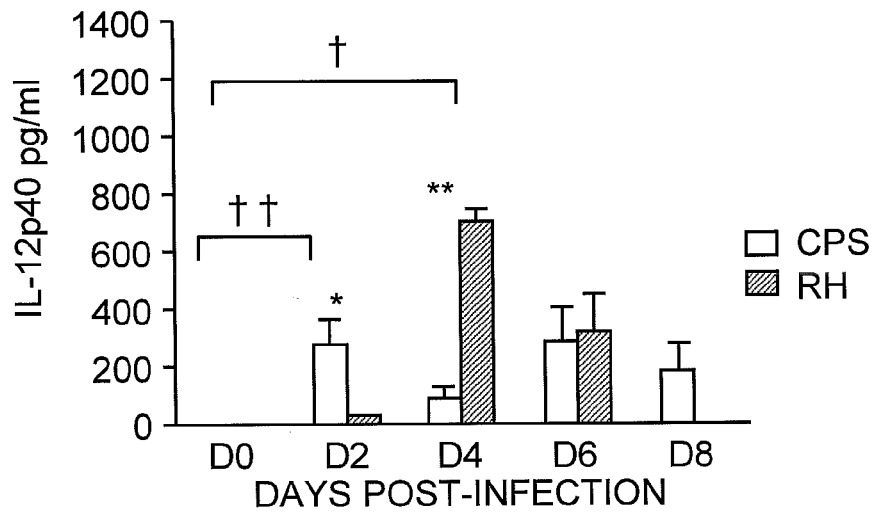
FIG. 5B, p=*0.03, **0.0001, $^\dagger$0.0001, $^{\dagger\dagger}$0.04.
Figure 5C:
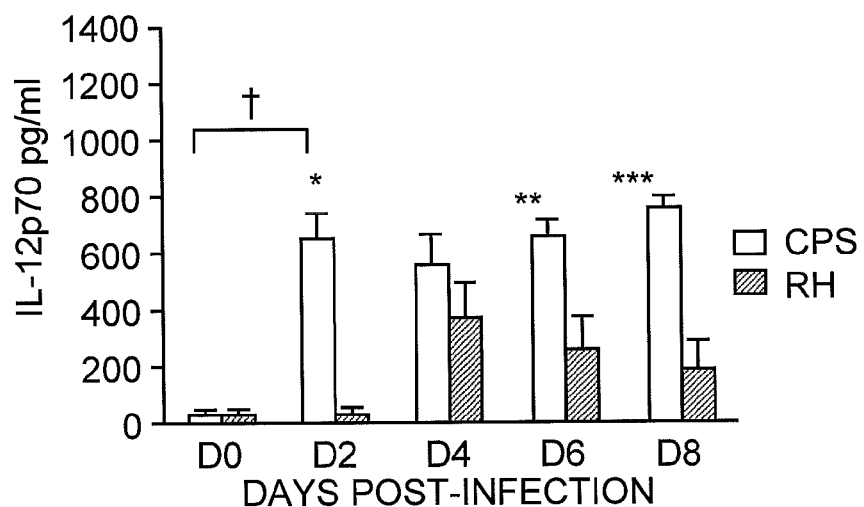
FIG. 5C, p=*0.007, 0.012, *0.001, $^\dagger$0.005.
Figure 5D:
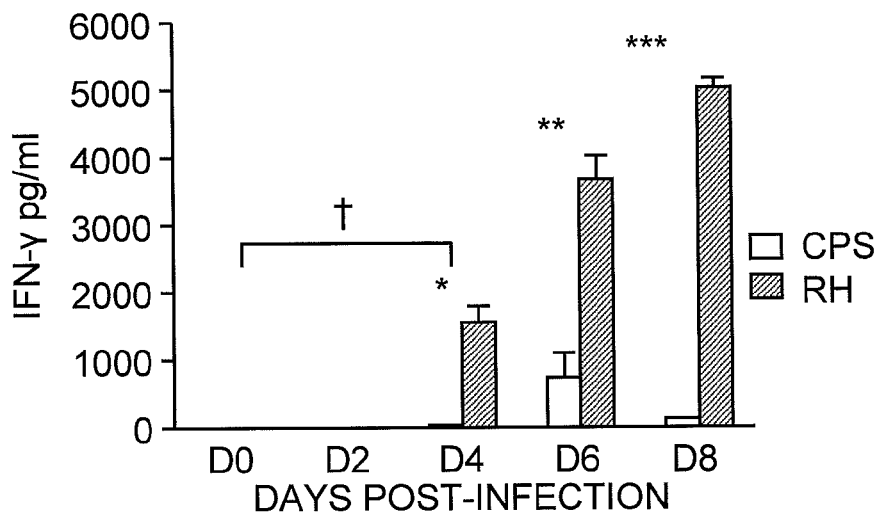
FIG. 5D, p=*0.001, 0.006, *0.0001, $^\dagger$0.001.
Figure 5E:
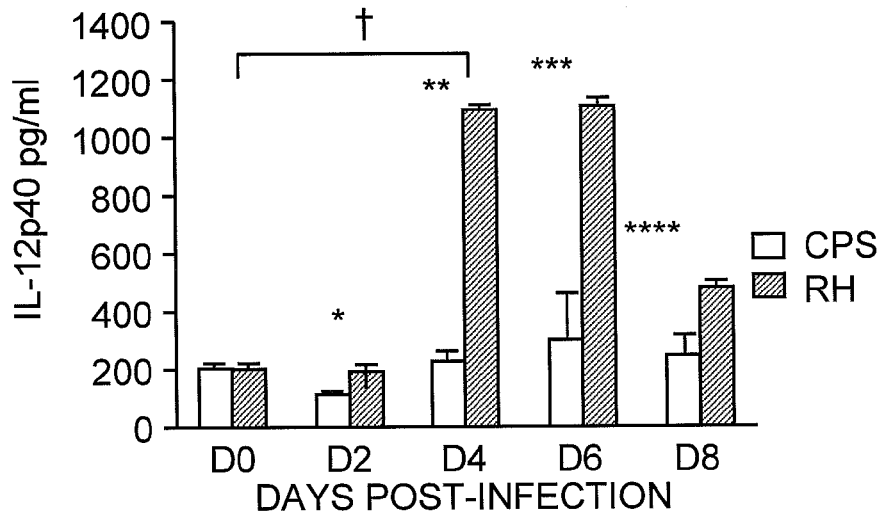
FIG. 5E, p=*0.02, 0.0001, *0.002, ****0.02, $^\dagger$0.0001.
Figure 5F:
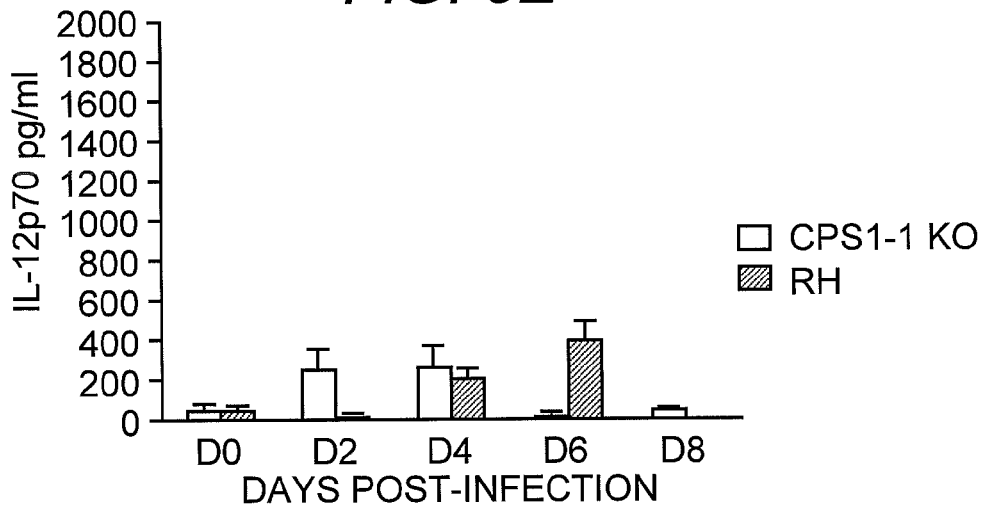
FIG. 5F, no significant differences.

As shown in FIG. 5B, cps1-1 vaccination induced a significant production of IL-12p40 by PECs by Day 2 post-infection as compared to that of Day 0 ($p=0.04$). Although PEC production of IL-12p40 from Day 2 through Day 8 did not significantly change, PEC from cps1-1-vaccinated mice more rapidly produced significant levels ($p=0.025$) than were observe in RH-infected mice at Day 2 post-infection (FIG. 5B). The opposite was true by Day 4, where PEC derived from RH-infected mice produced significantly more IL-12p40 (p<0.001) than PECs from cps1-1 vaccinated mice. In FIG. 5C it is revealed that PECs from cps1-1-vaccinated mice rapidly produce significantly greater levels of IL-12p70 by Day 2 post-infection as compared to RH with p=0.007. These lL-12p70 levels remained consistently high (Day 2 to Day 8) after cps1-1 vaccination, while Il-12p70 production from PECs after RH infection was delayed to Day 4 and was significantly lower by Day 6 and Day 8 with p=0.012 and p=0.001, respectively (FIG. 5C).

When comparing PECs cytokine production to that of splenocytes from cps1-1-vaccinated mice, higher PEC production (on a per cell basis) of IFN-γ (FIG. 5A and FIG. 5D) and IL-12p70 (FIG. 5C and FIG. 5F) was observed, while splenocyte production of IL12p40 from cps1-1-vaccinated mice was equivalent to that of PEC-production of this protein (FIG. 5B and FIG. 5E). These studies reveal that local production of Th-1 cytokines was more rapid and greater in response to cps1-1 vaccination. The data presented herein also indicates that the initial loss of control of the virulent RH infection may be due to a lack of an early potent cytokine response at the local site of infection. Significantly, it was observed that the immune response directed to a live and invasive parasite in the absence of replication-associated host cell and tissue damage is rapid and tightly controlled (FIGS. 3-5). These data indicate that transient and early (Day 2) systemic IFN-γ production and local IFN-γ production (Day 2 to Day 8), along with early and maintained (Day 2 to Day 8) IL-12p70 production both locally and systemically are sufficient to induce the development of long lasting protective immunity by the cps1-1 vaccine which is very effective at protecting against lethal challenge.

Model of a Local and Tightly Regulated Th-1 Immune Response to Vaccination With a Live, Non-Replicating Parasite in the Absence of Infection-Associated Host Tissue Destruction. Based on the results of analysis conducted herein, the following integrated kinetic model of the immune response to the attenuated non-replicating Type I parasite cps1-1 vaccine is contemplated. Inoculation i.p. with cps1-1 results in a rapid early recruitment of GR-1$^+$ CD68$^+$ granulocytes and GR-1$^+$ CD68$^+$ inflammatory macrophages into the local site of inoculation by Day 2. By Day 2 post-inoculation, some percentage of PEC-derived *T. gondii*-specific granulocytes and/or inflammatory macrophages has migrated peripherally to the spleen based on splenocyte production of IL-12p40 and IL-12p70 by Day 2 post-inoculation. It is possible that a small number of *T. gondii*-specific CD4$^+$ and/or CD8$^+$ T cells have also migrated to the spleen by Day 2. While the percentage of CD4$^+$ T cells does not rise until Day 4, by Day 2, the absolute number of CD4$^+$ T cells is slightly increased. Unexpectedly, the infiltration of CD8$^+$ T cells is more significant compared to CD4$^+$ T cells at Day 2. There is a transient systemic production of IFN-γ that is only detected at Day 2 that may be explained by the migration of *T. gondii* cells activated in the peritoneum to the spleen, or other lymphatic tissue. This indicates that by Day 2, the cps1-1 vaccine has already triggered immune surveillance to identify all locations and tissue where *T. gondii* parasites may have disseminated. However, because the vast majority of cps1-1-invaded cells remain at the original site of inoculation i.p., the Th-1-biased immune response amplifies locally in a tightly controlled manner, and at most, very minor peripheral or systemic responses develop. It appears that the cps1-1-vaccinated host has already committed to a Th-1-biased immune response by Day 2 based on cell infiltration and cytokine production profiles. In part, this early expansion via infiltration of inflammatory and adaptive Th-I cell types is inversely proportional to a migration of B cell populations out of the peritoneum by Day 2. The retention of B cells is stable though reduced. The tightly controlled Th-1 response may explain the eventual production of *T. gondii*-specific IgG1 and IgG2a antibody subclasses. It is inferred that the Th-1 response is tightly controlled based on the stable production of systemic- and PEC-derived IL-12p70 from Day 2 to Day 8, along with the low levels of IFN-γ observed at Day 2 that is likely to be derived from the infiltrating granulocytes and/or inflammatory macrophages. While IFN-γ is not detectable (<10 pg/ml) systemically after Day 2, the PEC-derived IFN-γ slightly increases by Day 4, peaks at Day 6, then declines markedly at Day 8, indicating that IFN-γ in the peritoneum after Day 2 correlates closely to the same kinetic pattern as the percentage of CD8$^+$ T cells present at the local site of vaccination. CD4$^+$ T cells may contribute to PEC-derived IFN-γ although the continued rise in CD4$^+$ T cells at Day 8 does not correlate with the significant decline in IFN-γ production between Day 6 and Day 8. The innate response subsides between Day 2 and Day 4 based on loss of systemic IFN-γ and the marked loss of granulocytes and inflammatory macrophages that infiltrate between Day 0 and Day 2. The slight increase in inflammatory macrophages between Day 4 and Day 6 indicates that some percentage of *T gondii*-specific Gr-1$^+$ CD68$^+$ cells that left the peritoneum on Day 2 to search peripheral organs has returned to the peritoneum where most of the originally vaccinated parasites remain locally positioned. These returning Gr-1$^+$ CD68$^+$ inflammatory macrophages or infiltrating T-reg cells may suppress the Th-1 response and explain the decline in IFN-γ between Day 6 and Day 8. The Day 4 to Day 6 Gr-1$^+$ CD68$^+$ increase cannot by itself explain the marked increase in IFN-γ between Day 4 and Day 6 and these inflammatory macrophages largely depart the peritoneum by Day 8. The cross-talk between CD4$^+$ and CD8$^+$ T cells may explain the peak of IFN-γ production on Day 6. The decline of IFN-γ by Day 8 indicates the local Th-l inflammatory response is rapidly resolving. In regard to T cells, the data herein cannot discriminate between two models where the marked increase in CD4$^+$ and CD8$^+$ T cells at Day 6 (stable to day) is from continued infiltration of new T cells to the peritoneum or alternatively is due to IFN-γ-dependent expansion of previously peritoneum-activated *T gondii*-specific T cells. It is contemplated that the complete CD4$^+$ and CD8$^+$ T cell response is determined by cell infiltration, antigen presentation, and signaling events that have occurred by Day 2 post-vaccination with cps1-1. The Gr-1$^+$ CD68$^+$ inflammatory macrophage population may play a role in antigen presentation to CD4$^+$ and CD8$^+$ T cells. Infected epithelial cells or other cps1-1-invaded cell types are also likely to present antigen to T cells. The rapid production of IL-12p70 by Day 2 and its production maintained through Day 8 by PECs is likely important for tight regulation of the Th-1 immune response. The source of PEC-derived IL-12p70 is under investigation. Early production of IL-12p70 by Day 2 may originate from the Gr-1$^+$ CD68$^+$ granulocytes and Gr-1$^+$ CD68$^+$ inflammatory macrophages (Bennouna, et al. (2003) *J. Immunol.* 171:6052-6058; Bliss, et al. (2000) *J. Immunol.* 165:4515-4521). However, IL-12p70 production rises significantly by Day 4 while the granulocyte population essentially disappears, and based on cell type profiles in the peritoneum the only profile that correlates precisely to production of IL12p70 is the CD19$^+$ B cell. The immune response elicited to cps1-1 vaccination is local and rapid, and the inflammatory response is tightly regulated. This immune response leads to a very effective and long lasting immunity to *T. gondii*.

EXAMPLE 2

Intranasal Vaccination with *T. Gondii* Elicits Cell-Mediated Immunity

Figure 7:
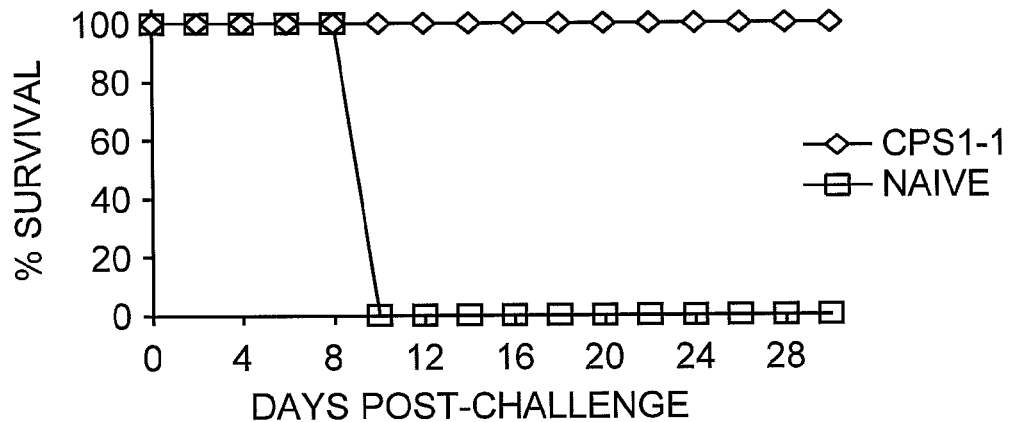
FIG. 7 shows results of intranasal vaccination studies using non-replicating cps1-1 mutant parasites. Groups of 10 C57BL/6 mice were immunized with PBS only (naïve), or with $1 \times 10^6$ cps1-1 parasites in PBS in 0.01 ml by i.n. inoculation. Thirty days after i.n. immunization, mice were challenged with a 200× lethal dose equivalent of strain RH and survival was monitored.

The successful i.p. and i.v. routes for cps1-1 immunization require injection of cps1-1 parasites. To determine whether cps1-1 immunization can be delivered via intranasal (i.n.) immunization, which is a more suitable route, e.g., in young children and adults, a series of attenuated *T. gondii* i.n. immunizations were conducted. Successful cps1-1 immunization requires that the parasite invades host cells for eliciting protection. Simply heat killing, sonicating cps1-1 parasites, or blocking invasion will completely abrogate the protective immunity induced by cps1-1. Invasion of cps1-1 parasites into host cells is absolutely required for eliciting long lasting CD8 immunity. Because the nasal passage has not been reported to be a natural route of entry of the parasite and previous studies have not addressed this route as a means of eliciting protective immunity, preliminary i.n. studies included immunization with two different doses of cps1-1, with two immunizations given two weeks apart before administering a lethal RH challenge 30 days post-immunization. As shown in FIG. 7, immunization of $1 \times 10^6$ cps1-1 parasites by the i.n. route provided complete (100%) protection from a lethal challenge of RH (200× lethal dose equivalents). Similarly, a $3 \times 10^6$ dose by the i.n. route provided complete protection. Intranasal immunization with the live, critically-attenuated cps1-1 demonstrates that this parasite can be safely delivered through the non-invasive intranasal route and elicit strong long-lasting CD8 T cell immunity. Thus, non-invasive intranasal vaccination with attenuated *T. gondii* can be an effective approach to elicit Th1 immunity in young children or newborns, as well as adults.

EXAMPLE 3

Essential Indels and Domains CPSII of *T. gondii*

This example presents data demonstrating that a CPSII cDNA minigene efficiently complements the uracil auxotrophy of CPSII-deficient mutants restoring parasite growth and virulence. Complementation assays revealed that engineered mutations within or proximal to the catalytic triad of the N-terminal glutamine amidotransferase (GATase) domain inactivated the complementation activity of *T. gondii* CPSII and demonstrated a critical dependence on the apicomplexan CPSII GATase domain in vivo. Moreover, indels present within the *T. gondii* CPSII GATase domain, as well as the C-terminal allosteric regulatory domain were found to be essential. In addition, several mutations directed at residues implicated in allosteric regulation in *Escherichia coli* CPS either abolished or markedly suppressed complementation and further defined the functional importance of the allosteric regulatory region.

Plasmid Construction. A functional CPSII minigene encoding the authentic 1687 amino acids of carbamoyl phosphate synthetase was constructed by sequential coupling of defined cDNA segments generated by reverse transcriptase/PCR. First, a 1829 bp cDNA for the N-terminal GATase domain of CPSII was amplified from polyA+ mRNA from the RH strain (5'-ACT AGT GGT GAT GAC GAC GAC AAG ATG CCT CAC AGT GGA GGG C-3', SEQ ID NO:4; and 5'-GAT ATC CAC GTG TCG CGG CCG CGC TCT C-3', SEQ ID NO:5). The 1829 bp cDNA was introduced (SpeI/EcoRV) into pET41b (SpeI/XhoI-blunted). Next an N-terminal section of the CPS domain cDNA including bp 1829 to bp 3532 was generated (5'-GAG AGC GCG GCC GCG AC-3', SEQ ID NO:6; and 5'-CAC GTG GAG GCG AGA CGT CGT CGT C-3', SEQ ID NO:7) and fused to the GATase domain (NotI/PmlI). The remainder of the CPS domain was constructed by amplifying two cDNA segments, bp 3003-4097 and bp 4097-5064 (5'-AGT ACT TGA TGA ATT CAC CG-3', SEQ ID NO:8, and 5'-TTT CTG CGA GAT CTT CTT CAC G-3', SEQ ID NO:9; and 5'-GCG TGA AGA AGA TCT CGC AG-3', SEQ ID NO:10, and 5'-ATC GAT CAC GTG ATT TTT GAG GCC AGT ATT CAT CC-3', SEQ ID NO:11, respectively), and then the two C-terminal segments were fused in PCR4TOPO (EcoRI/BglII). Finally the C-terminal section of CPS was fused with the N-terminal section in PET41b (EcoRI/PmlI) and the complete 5064 bp CPSII minigene coding sequence was determined to verify authenticity.

Both 5' and 3' untranslated regions (UTRs) were amplified from RH genomic DNA. The 5' UTR, to bp -516, was amplified (5'-GCT AGC GTG GAC CCC CAT TAT CCT TCG C-3', SEQ ID NO:12, and 5'-ACT AGT CAC TCG TCG AAT GGT TGC GTC TG-3', SEQ ID NO:13), and the 5' UTR, to bp -2057, was amplified (5'-GCT AGC GTG GAC CCC CAT TAT CCT TCG C-3', SEQ ID NO:14, and 5'-ACT AGT GAA ATC GCG ATC AAC GCG ACA G-3', SEQ ID NO:15). The 3' UTR (920 bp) was amplified (5'-AGT ACT TGC ACC ACC ACC ACC ACC ACT AAT TTC CAA TAC TTT CGC CAA AAA CGT TCC-3', SEQ ID NO:16, and 5'-GCG CAC GTG GTT GAG AGC TTG ACC CGC ATG CA-3', SEQ ID NO:17). Finally, 5' UTR segments (ScaI/SpeI) were fused into the CPSII minigene (SpeI), and subsequently the 3' UTR (ScaI/PmlI) was fused into the above plasmid(s) (ScaI/PmlI).

Site-Directed Mutagenesis. Mutations were first introduced into the either the GATase or CPS domains using Stratagene's PCR based QUIKCHANGE® II XL Site-Directed Mutagenesis Kit. Products were DpnI-digested, transformed into XL-10 GOLD Ultracomp cells, and subsequently transferred into the full CPSII complementation vector. Forward and reverse complementary primers containing the desired mutations were used to create the desired mutations. Plasmids with correct coding region and engineered CPSII minigene mutation(s) were verified by sequence analysis prior to transfection experiments.

Parasite Culture and Transfection. Tachyzoites of strain cps1-1 were maintained in human foreskin fibroblasts with or without uracil supplementation (300 mM) (Fox & Bzik (2002) *Nature* 415:926-929). Wild-type or CPSII minigene plasmids containing defined mutations were transfected (20 mg) into the cps1-1 background and selections were performed without drug addition in the absence of uracil using methods known in the art (Fox & Bzik (2002) supra). Briefly $1 \times 10^7$ freshly isolated tachyzoites of strain cps1-1 were transfected in 0.4 ml electroporation buffer. Growth and complementation in the absence of uracil supplementation was scored as described herein. Transfected cps1-1 parasites growing in the absence of uracil were cloned by limiting dilution.

Determination of Parasite Growth Rate in cps1-1 Complementation Assays. Following transfection of strain cps1-1 with wild-type or mutant CPSII minigenes, fresh monolayers of HFF cells were infected in 5 ml of infection medium with 25% of the transfected parasites. At two hours post-transfection, monolayers were washed two times with PBS to remove parasites that had not invaded. At 36 hours post-transfection, the growth rate was measured by scoring tachyzoites per vacuole by examination of randomly selected vacuoles in light microscopy. Vacuoles containing one parasite per vacuole were excluded from counting. A total of 50 vacuoles with two or more parasites were scored to determine "mean of parasites per vacuole" in each transient transfection assay. The growth rate was then converted to a relative doubling time based on a 36 hour growth period. Experiments were independently repeated at least three times. A student t-test was used to calculate the standard error of the mean.

Determination of Transient Complementation Efficiency. Following transfection of strain cps1-1 with wild-type or mutant CPSII minigenes, fresh monolayers of HFF cells were infected in 5 ml of infection medium with 25% of the transfected parasites. At 2 hours post-transfection, monolayers were washed two times with PBS to remove parasites that had not invaded, and fresh infection medium was returned to cultures. At 36 hours post-transfection, the transient transfection efficiency was measured at the same time as growth rate by scoring the number of vacuoles containing two or more parasites per light microscope "field" at a fixed objective during the scoring of 50 vacuoles as described above. Vacuoles with only one parasite per vacuole were excluded from counting. Transient complementation efficiency is reported as % of control vacuoles observed using the wild-type Pc 4 CPSII minigene. Experiments were repeated a minimum of three independent times and a student t-test was used to calculate the standard error of the mean.

Determination of Stable Complementation Efficiency. Strain cps1-1 was transfected with wild-type or mutant CPSII minigenes. Immediately following transfection, the contents of the transfection cuvette (and the first wash of the cuvette with infection medium) was transferred into 20 ml of infection medium. Serial dilutions of the transfected tachyzoites were prepared in infection medium, fresh HFF monolayers, in duplicate 25 cm$^2$ flasks, were infected with 2%, 0.5%, or 0.1% of total transfected parasites, and plaque forming units (PFU) were scored. The infected HFF flasks were left undisturbed for seven days and then monolayers were fixed and stained with COOMASSIE Blue to score the number of PFU. Stable complementation efficiency is reported as % of control PFU observed using the wild-type Pc 4 CPSII minigene. Experiments were repeated a minimum of three independent times and a student t-test was used to calculate the standard error of the mean. Control experiments using the pET41b plasmid without the CPSII minigene were conducted a minimum of four times and no PFU were observed in the absence of uracil supplementation.

Virulence Assays. Adult, 6-8 week old C57Bl/6 mice were obtained from Jackson Labs (Bar Harbor, Me.) and mice were maintained in TECNIPLAST SEALSAFE mouse cages on vent racks. All mice were cared for and handled according to NIH-approved Institutional animal care and use committee guidelines. Tachyzoites were isolated from freshly lysed HFF monolayers and were purified by filtration through sterile 3 mm NUCLEPORE membranes. Tachyzoites were washed in PBS, counted in a hemocytometer to determine parasite number, and a PBS solution prepared with $1 \times 10^4$ or $1 \times 10^7$ tachyzoites per ml. Groups of four mice were injected intraperitoneally (i.p.) with 0.2 ml ($2 \times 10^6$ tachyzoites for strain cps1-1, or $2 \times 10^3$ tachyzoites for cloned isolates obtained after transfections with Pc 4, N348A, and D873-910 plasmids. Mice were then monitored daily for degree of illness and survival. The virulence assays were performed twice.

Complementation of Uracil Auxotrophy and Virulence. The cps1-1 mutant of *T. gondii* invades host cells but due to pyrimidine starvation exhibits no detectable growth rate in the absence of uracil supplementation (Fox & Bzik (2002) supra). It was expected that providing a functional CPSII gene to the cps1-1 mutant would restore production of carbamoyl phosphate required for biosynthesis of UMP. Due to the large size and intron/exon complexity of the genomic DNA locus of CPSII (Fox & Bzik (2003) *Int. J. Parasitol.* 33:89-96), a cDNA minigene was constructed, which encoded the 1687 amino acid CPSII polypeptide under the control of authentic CPSII 5' UTR and 3' UTR regulatory regions. To examine complementation, plasmids representing a promoter-less minigene coding region construct, as well as minigenes under the control of either 0.5 kb or 2.0 kb of 5' UTR, were transfected into the cps1-1 uracil auxotrophic *T. gondii* mutant and cultured in HFF cells in the absence or presence of uracil. Tachyzoites per parasite vacuole were scored 36 hours after transfection. The promoter-less construct Pc 0, as well as the 0.5 kb 5' UTR construct, Pc 2, failed to complement the cps1-1 mutant and did not restore any detectable growth rate in the absence of uracil. In contrast, the 2 kb 5' UTR CPSII minigene, Pc 4, efficiently complemented the cps1-1 mutant and restored a normal tachyzoite growth rate in the absence of uracil.

In quantitative experiments, plasmids Pc 0, Pc 2, and Pc 4 were transfected into strain cps1-1 and total plaque forming units (PFU) determined at seven days after transfection in the absence of uracil supplementation. Plasmids Pc 0, Pc 2, and the vector pET41b produced no PFU (0%) following transfection of cps1-1. In contrast, during the course of this study 16 independent transfections of $1 \times 10^7$ cps1-1 tachyzoites were performed using plasmid Pc 4 and the mean of PFU was determined to be 1.8%±0.14 of the original $1 \times 10^7$ transfected tachyzoites.

PFU arising from transfection experiments with Pc 4 or mutant alleles of CPSII were cloned by limiting dilution and stable isolates were examined for virulence in mice. The cps1-1 strain is essentially completely avirulent (Fox & Bzik (2002) supra). In contrast, transfection of cps1-1 with plasmid Pc 4 produced stable clones that exhibited the high virulence phenotype of the parental RH strain in C57Bl/6 mice.

Functional Analysis of the Glutamine Amidotransferase Domain of CPSII. The requirement of the fused eukaryotic GATase domain to produce ammonia for CPS function in apicomplexan CPSII has not been previously examined in vivo. The mutation C345 to A345 was constructed in plasmid Pc 4 in an essential catalytic triad residue of the GATase domain equivalent to C269 that abolished GATase activity in *E. coli* (Rubino, et al. (1987) *J. Biol. Chem.* 262:4382-4386) (Table 2).

TABLE 2

| Mutation | Location in Tg | Effect on CPS or CPSII |
| --- | --- | --- |
| C269A* | C345 | — GATase activity |
| G359F* | G435 | Ammonia leaks, uncoupling GATase & CPS |
| T456A# | T533 | — MAPK activation |
| E761A* | E1316 | — ornithine activation & UMP repression |
| H781K* | H1336 | ↓ CPS activity, ornithine act., & UMP repression |
| T974A* | T1530 | ↓ ornithine & IMP activation, & UMP repression |
| S1345A# | T1530 | ↓ PRPP activation |
| T1042A* | T1649 | ↓ ornithine binding |

*Escherichia coli*\*;
Hamster#,
*T. gondii* Tg.
—, abolishes;
↓ reduces.

The *T. gondii* C345 to A345 mutation completely abolished complementation activity, indicating that CPSII is dependent on a functional GATase domain for the production of ammonia in vivo (Table 3).

TABLE 3

| GATase Mutation | growth rate (h) | Transient efficiency[1] | stable efficiency[2] |
|---|---|---|---|
| Tg Pc 4 (wt) | 7.4 ± 0.08 | 100 | 100 |
| Tg Δ172-229 | n.d. | 0 | 0 |
| Tg C345A | n.d. | 0 | 0 |
| Tg N348R | n.d. | 0 | 0 |
| Tg N348A | 8.2 ± 0.27 | 96 ± 6.6 | 91 ± 6.8 |
| Tg P385R | 11.5 ± 0.95 | 18 ± 4.0 | 1.3 ± 0.51 |
| Tg G435F | 12.4 ± 0.45 | 8.4 ± 2.3 | 0.6 ± 0.27 |
| Tg Δ455-457 | 7.5 ± 0.15 | 98 ± 9.8 | 103 ± 13 |
| Tg Δ454-470 | 8.9 ± 0.51 | 64 ± 19 | 11 ± 4.2 |

No growth detected (n.d.).
[1]Transient complementation was scored as the % of control vacuoles of Pc 4 transfection.
[2]Stable complementation was scored as % of control PFU of Pc 4 transfection.

The dependence of *T. gondii* CPSII activity on the amidotransferase domain validated the analysis of unique sites within this domain as parasite specific drug targets.

The proximal N348 residue was subsequently targeted as this residue is selectively present in most protozoan CPSII enzymes (Fox & Bzik (2003) supra). Mutation of N348 to R348 abolished complementation activity, whereas mutation of N348 to A348 modestly reduced the initial growth rate (from 7.4 to 8.4 hours) in the 36 hour growth assay, but did not significantly interfere with the efficiency of transient or stable complementation (Table 3). A stable clone isolated after transfection with the A348 mutant exhibited the high virulence phenotype of the parental RH strain in C57Bl/6 mice.

Amino acid 385, adjacent to residues including the catalytic triad, is uniquely a proline residue in *T. gondii* CPSII (Fox & Bzik (2003) supra). Changing amino acid P385 to R385 had a dramatic effect on reducing the initial parasite growth rate (from 7.4 to 11.5 hours), and reduced transient complementation efficiency to 18% and stable complementation efficiency to 1.3% of the control (Table 3). Clones obtained from transfection with the R385 mutant indicated that 3 to 7 copies of the CPSII minigene were stably integrated in complemented parasites.

The naturally occurring CPS enzyme is composed of an a, b-heterodimeric protein with an "ammonia tunnel" which channels ammonia produced by the small subunit GATase to the binding site for the first molecule of MgATP located within the N-terminal half of CPS in the carboxy phosphate domain (Miles, et al. (1993) *Biochemistry* 32:232-240; Thoden, et al. (1997) *Biochemistry* 36:6305-6316; Miles, et al. (1998) *Biochemistry* 37:16773-16779; Huang & Raushel (1999) *Biochemistry* 38:15909-15914; Thoden, et al. (1999) *Acta Crystallogr. D Biol. Crystallogr.* 55:8-24; Huang & Raushel (2000) *Biochemistry* 39:3240-3247; Huang & Raushel (2000) *J. Biol. Chem.* 275:26233-26240; Huang & Raushel (2000) *Arch. Biochem. Biophys.* 380:174-180; Miles & Raushel (2000) *Biochemistry* 39:5051-5056; Miles, et al. (2002) *J. Biol. Chem.* 277:4368-4373). The carboxy phosphate domain first phosphorylates (MgATP) bicarbonate to carboxy phosphate, which activates GATase activity ~1000-fold (Miles & Raushel (2000) supra). Carboxy phosphate then combines rapidly with ammonia delivered in a highly coordinated fashion from the GATase domain to form carbamate (Thoden, et al. (1999) *Acta Crystallogr. D* 8-24). Perforation of the ammonia tunnel in *E. coli* CPS via mutation of G359 to F359 results in ammonia leakage from the tunnel and loss of CPS activity (Table 2). The Gly residue corresponding to *E. coli* G359 is universally conserved in all GATases that are coupled with CPS activity (Fox & Bzik (2003) supra). Mutation of *T. gondii* G435 to F435, corresponding to the *E. coli* G359 to F359 mutation, caused a marked reduction in the initial parasite growth rate (from 7.4 to 12.4 hours), and reduced transient complementation efficiency to 8.4% and stable complementation efficiency to 0.6% of the control. These results indicate that disruption of the *T. gondii* CPSII ammonia tunnel markedly decreased CPSII complementation activity in vivo (Table 3), again revealing the strict dependence of the parasite CPS on ammonia produced by the fused GATase activity of CPSII.

The domain in *T. gondii* CPSII (amino acids 454-470) that links GATase with CPS domains was also examined. While deletion of amino acids 455 to 457 had no detectable effect on complementation activity, deletion of amino acids 454 to 470 caused a significant reduction in the initial parasite growth rate from 7.4 to 8.9 hours, as well as a reduction in stable complementation efficiency to 11% of the control (Table 3).

Deletion of Indels. Apicomplexan CPSII enzymes contain locations where novel insertions of amino acids (indels) occur at several locations within the GATase and CPS domains. While ribozyme targeting of a *P. falciparum* CPSII indel at the RNA level was previously shown to inhibit parasite proliferation (Flores, et al. (1997) *J. Biol. Chem.* 272:16940-16945), previous studies have not directly addressed the functional importance of indels in parasite proteins. The unusually frequent occurrence of novel insertions of low or high complexity within protozoan parasite proteins, particularly in *Plasmodium* sp. and *T. gondii* (Cherkasov, et al. (2006) *Proteins* 62:371-380; DePristo, et al. (2006) *Gene* 378:19-30), would provide parasite selective drug targets in instances where the indel provides a necessary function. Functional complementation of CPSII in *T. gondii* enabled a genetic test of essential indels. Accordingly, the *T. gondii* CPSII indel located in the GTPase domain was targeted. This indel, which other protozoans, fungi, mammals, and prokaryotes do not share, is located in other apicomplexan CPSII. Deletion of the GATase indel (E171-A229) completely abolished CPSII function as demonstrated by the inability of this mutant to complement the uracil auxotrophy of cps1-1 (Table 3). These results further establish this novel parasite-specific indel as a parasite-selective drug target within the essential GATase domain.

CPS is controlled via allosteric mechanisms acting through specific allosteric effectors and their binding interactions with the C-terminal domain of CPS.B (Braxton, et al. (1999) *Biochemistry* 38:1394-1401; Thoden, et al. (1999) *J. Biol. Chem.* 274:22502-22507; Fresquet, et al. (2000) *J. Mol. Biol.* 299:979-991; Pierrat, et al. (2002) *Arch. Biochem. Biophys.* 400:26-33). Due to the complex assembly of five substrates via four chemical reactions at three active sites separated by ~100 Å (Thoden, et al. (1997) supra; Thoden, et al. (1999) supra), the CPS enzyme activities are highly synchronized with one another and activity is tightly regulated by allosteric end-product repression as well as allosteric activation. The C-terminal ~150 amino acids of the large CPS subunit contain the regulatory domain controlling allosteric regulation of CPS activity where binding pockets exist that mediate direct physical interaction with allosteric effector molecules (Mora, et al. (1999) *FEBS Lett.* 446:133-136; Thoden, et al. (1999) supra; Fresquet, et al. (2000) supra). Interaction of allosteric effectors with the C-terminal regulatory domain directly trigger conformational changes in CPS affecting activity and/or synchronization of active sites (Thoden, et al. (1999) supra). *T. gondii* and *B. bovis* CPSII share an indel location within the C-terminal regulatory domain. To examine whether this novel indel was essential to CPSII function, a deletion of the *T. gondii* C-terminal indel (G1592 to R1628) was constructed. This deletion completely abolished CPSII complementation activity (Table 4).

TABLE 4

| CPS Mutation | Growth rate (h) | Transient efficiency[1] | Stable efficiency[2] |
| --- | --- | --- | --- |
| Tg Pc 4 (wt) | 7.4 ± 0.08 | 100 | 100 |
| Tg T533A | 7.4 ± 0.18 | 105 ± 7.2 | 98 ± 6.9 |
| Tg S581A | 7.3 ± 0.14 | 109 ± 11 | 104 ± 8.5 |
| Tg Δ873-910 | 8.2 ± 0.27 | 113 ± 12 | 65 ± 11 |
| Tg E1316A | n.d. | 0 | 0 |
| Tg E1318A | n.d. | 0 | 0 |
| Tg H1336K | n.d. | 0 | 0 |
| Tg T1430A | 7.7 ± 0.21 | 86 ± 5.7 | 82 ± 8.4 |
| Tg T1530A | 8.6 ± 0.25 | 51 ± 13 | 10 ± 3.2 |
| Tg T1530 fs | n.d. | 0 | 0 |
| Tg Δ1592-1628 | n.d. | 0 | 0 |
| Tg T1649A | 8.5 ± 0.21 | 65 ± 5.2 | 37 ± 7.0 |

No growth detected (n.d.).
[1]Transient complementation was scored as the % of control vacuoles of Pc 4 transfection.
[2]Stable complementation was scored as % of control PFU of Pc 4 transfection.

The carboxy terminal region of the CPSII.A domain (domain A3) contains the oligomerization domain known to coordinate the formation of tetramers of *E. coli* CPS (Thoden, et al. (1997) supra; Kim & Raushel (2001) *Biochemistry* 40:11030-11036). On the N-terminal side of the putative CPSII oligomerization domain, a novel indel of ~34 amino acids is present in *T. gondii* CPSII (Fox & Bzik (2003) supra). Deletion of this indel (C873-G910) caused a minor, but detectable, disruption in complementation activity based on a reduced initial growth rate (from 7.4 to 8.2 hours), similar transient complementation efficiency (113%), and slightly reduced stable complementation efficiency to 65% of the control (Table 4). Interestingly, the more subtle effect of this indel deletion in the *T. gondii* CPSII oligomerization domain is potentially similar to the relatively minor effect on *E. coli* CPS activity previously observed in mutants blocked in oligomerization contact regions that prevent tetramer but not dimer formation (Kim & Raushel (2001) supra). A stable clone obtained from transfection with the D873-910 mutant exhibited the high virulence phenotype of the parental RH strain in C57Bl/6 mice.

CPSII Regulatory Domains. Suppression of mammalian CPSII activity is highly dependent on the presence or absence of regulated phosphorylation at a distinct MAP kinase site at (T456) in the carboxy phosphate CPSII.A domain (Graves, et al. (2000) *Nature* 403:328-332). *T. gondii* and other lower eukaryotic forms of CPSII are distinct from mammalian CPSII in lacking this critical MAPK site (Fox & Bzik (2003) supra). *T. gondii* CPSII shares the Threonine residue corresponding to the mammalian T456 position and this residue was mutated to exclude the possibility that a novel parasite kinase may control CPSII activation. Mutation of T533 to A533 in *T. gondii* CPSII had no significant effect on complementation activity (Table 4). It was also determined whether the nearby putative MAPK core SP site present in *T. gondii*, but absent in mammalian CPSII, was necessary for activity. Mutation of S581 to A581 also had no detectable effect on complementation activity (Table 4).

*E. coli* CPS activity is repressed by UMP, strongly activated by ornithine and weakly activated by IMP, whereas eukaryotic CPSII is typically activated by PRPP and is repressed by UTP (or UDP in kinetiplastids) (Jones (1980) *Ann. Rev. Biochem.* 49:253-279; Nara, et al. (1998) *Biochim. Biophys. Acta* 1387:462-468). Strikingly, *T. gondii* CPSII is insensitive to allosteric activation by PRPP, and relatively high levels of UTP were required for suppression (Asai, et al. (1983) *Mol. Biochem. Parasitol.* 7:89-100). To gain further insight into the importance of allosteric regulatory regions and the type of regulation occurring in *T. gondii* CPSII, mutations were created in several amino acid residues that were conserved between the *T. gondii* and *E. coli* C-terminal regulatory domains, and were also known to mediate allosteric control in *E. coli* CPS (Table 2). While IMP induces only modest allosteric effects on *E. coli* CPS activity, ornithine potently activates the glutamine dependent ATPase and ATP synthesis reactions and thereby markedly upregulates activity by increasing the affinity of CPS for its nucleotide substrates, while overriding the strong effect of UMP to suppress the catalytic activity of CPS (Braxton, et al. (1999) supra). The conserved ornithine binding sites identified in *T. gondii* CPSII analogous to those previously identified in *E. coli* were targeted (Table 2). The K loop coordinates the binding of a potassium ion and includes the conserved residue H781 that also coordinates the transmission of the allosteric regulatory signals from the C-terminal regulatory domain (Thoden, et al. (1999) supra; Pierrat, et al. (2002) supra). Mutation of H781 to K781 in *E. coli* CPS reduced the magnitude of the allosteric effects of both ornithine and UMP, decreased the allosteric response to IMP, and also diminished the catalytic activity of CPS by one to two orders of magnitude in the absence of allosteric effectors (Pierrat, et al. (2002) supra). In *T. gondii*, it was found that a CPSII minigene with the analogous mutation (H1336 to K1336) failed to detectably complement the uracil auxotrophy of the cps1-1 mutant (Table 4).

A second mutation (E761 to A761), also within the K loop of *E. coli* CPS, was previously found to be crucial to the transmission of the allosteric activation signal by ornithine, but did not affect catalytic turnover in the absence of effectors. This mutation also eliminated feedback repression by UMP and decreased activation by IMP (Pierrat, et al. (2002) supra). In *T. gondii* CPSII, it was found that the analogous mutation of E1316 to A1316 resulted in a complete loss of complementation activity by the mutant CPSII minigene (Table 4). Interestingly, a second mutation (E1318A to A1318) at a nonconserved residue two amino acids downstream of E1316 also resulted in a complete loss of complementation activity by the mutant CPSII minigene (Table 4).

To further define the extent of the impact of mutations within the allosteric regulatory region, a residue was targeted in the conserved region between *T. gondii* and the *E. coli* CPS.B3 allosteric regulatory region (T974) that strongly influenced the allosteric response to ornithine in *E. coli* CPS (Table 2). The mutation T974 to A974 disrupted the IMP/UMP binding pocket in *E. coli* CPS and not only abolished UMP inhibition and IMP activation, but also decreased activation by ornithine (Fresquet, et al. (2000) supra). Interestingly, this site also plays a role in allosteric control in mammalian CPSII as well, since mutation of the corresponding hamster residue S1355 to A1355 nearly abolished activation by PRPP and lowered overall CPSII activity ~5-fold (Simmons, et al. (2004) *Biochem. J.* 378:991-998). While *T. gondii* CPSII is nonresponsive to PRPP in vitro, mutation of the analogous residue in *T. gondii* CPSII (T1530 to A1530) significantly reduced CPSII complementation activity based on a reduced initial parasite growth rate (from 7.4 to 8.6 hours), and reduced transient complementation efficiency to 51% and stable complementation efficiency to 10% of the control, suggesting several copies of this mutant allele are necessary to fully support parasite growth (Table 4). A second conserved residue (T1042) in the *E. coli* regulatory domain plays a direct role in ornithine binding (Pierrat, et al. (2002) supra). Mutation of T1042 to A1042 in *E. coli* CPS reduces the magnitude of the allosteric response to ornithine. The analogous mutation T1649 to A1649 in *T. gondii* had the more modest effect of slightly lowering the initial growth rate (from 7.4 to 8.5 hours), and reduced transient complementation efficiency to 65% and stable complementation efficiency to 37% of the control. The overall importance of the relatively nonconserved *T. gondii* CPSII C-terminal regulatory region as a putative drug target could readily be seen through a frameshift mutation that was incorporated into T1530 that effectively deleted much of the CPS.B3 regulatory region and abolished complementation (Table 4).

These results indicate that residues that are known to mediate allosteric interaction in *E. coli* CPS and mammalian CPSII are likely to play a role in allosteric regulation in *T. gondii* CPSII. The major negative impact on the ability to complement by mutating residues that selectively affect up-regulation by ornithine in *E. coli* CPS, regardless of whether the allosteric effects of UMP or IMP are maintained, indicates allosteric regulation by ornithine or a related effector in *Toxoplasma gondii* and indicates points at which to intervene biochemically. It is notable that *T. gondii* is metabolically distinct from animals and many eukaryotes in being naturally auxotrophic for both ornithine and purines (Chaudhary (2007) *Toxoplasma gondii: The Model Apicomplexan Parasite: Perspectives and Methods*. London: Elsevier; Fox (2007) *Toxoplasma*: Molecular and Cellular Biology. Horizon Bioscience, Norwich). These natural auxotrophic requirements for parasite growth may be linked to novel strategies for allosteric regulation of CPSII, control of pyrimidine biosynthesis and balancing of purine and pyrimidine pools in protozoan parasites (Asai, et al. (1983) supra; Nara, et al. (1998) supra; Fox & Bzik (2003) supra). Studies have shown that indels occur more frequently within genes from *T. gondii* and *Plasmodium* sp. and may represent parasite-selective drug targets (Cherkasov, et al. (2006) supra; DePristo, et al. (2006) supra). Here, it is shown that deletion of the GATase indel as well as the C-terminal regulatory indel completely abolished complementation activity of CPSII minigenes. Thus, these results indicate that a functional and essential role for a number of C-terminal amino acids known to transmit the allosteric regulatory signals in mammalian CPSII or *E. coli* CPS. *T. gondii* CPSII is dependent on GATase for production of ammonia in vivo, and an ammonia tunnel potentially analogous to the ammonia tunnel described in *E. coli* CPS appears to be present.

EXAMPLE 4

Efficient Gene Replacements in *T. gondii* Strains Deficient in Nonhomologous End-Joining This example describes the identification of Ku genes and genetic disruption of Ku80 that functions in nonhomologous end-joining of double-strand DNA breaks. With the use of ΔKu80 knockout strains nearly 100% of transformants exhibit a double cross-over homologous recombination event resulting in gene replacement whether targeted at the Ku80 locus, the uracil phosphoribosyltransferase locus, or the carbamoyl phosphate synthetase II locus. Target DNA requirements of homology length, DNA concentration and DNA conformation necessary for efficient gene replacements were determined using a gene healing strategy that specifically measured homologous recombination mediated chromosomal repair of a disrupted HXGPRT locus. Unexpectedly, target DNA flanks of only ~450 bp were found to be sufficient for efficient gene replacements in *T. gondii*. Ku80 knockouts stably retained a normal growth rate in vitro and high virulence in murine infection, but exhibited an increased sensitivity to double-strand DNA breaks that were artificially induced by treatment with phleomycin or ionizing radiation.

Strains and Culture Conditions. The parental strains of *Toxoplasma gondii* used in this study were RH (Sabin (1941) *J. Am. Med. Assoc.* 116:801-7) and RHΔHXGPRT (Donald, et al. (1996) *J. Biol. Chem.* 271:14010-9). Hypoxanthine-xanthine-guanine phosphoribosyltransferase (HXGPRT) is referred to herein also as HX. A list of strains used in this study is shown in Table 5.

TABLE 5

| Strain | Parent | Genotype |
| --- | --- | --- |
| RH 30 | RH(ERP)[a] | wild-type |
| RHΔHX | RH[b] | ΔHXGPRT |
| RHΔKu80::HX | RHΔHX[c] | ΔKu80::HXGPRT |
| RHDHXΔKu80::DHFRTKTS | RHΔKu80::HX[c] | ΔHXGPRTΔKu80::DHFRTKTS |
| RHΔKu80ΔHX | RHΔKu80::HX[c] | ΔKu80ΔHXGPRT |
| RHΔKu80 | RHΔKu80ΔHX[c] | ΔKu80 |
| RHΔKu80ΔUPT(S)::HX | RHΔKu80ΔHX[c] | ΔKu80ΔUPRT::HXGPRT |
| RHΔKu80ΔUPT(B)::HX | RHΔKu80ΔHX[c] | ΔKu80ΔUPRT::HXGPRT |
| RHΔKu80ΔUPTΔHX | RHΔKu80ΔUPT(B)::HX[c] | ΔKu80ΔUPRTΔHXGPRT |
| RHΔKu80ΔCPSII::cpsII/HX | RHΔKu80ΔHX[c] | ΔKu80ΔCPSII::cpsII/HX |

[a]Pfefferkorn & Pfefferkorn (1976) Exp. Parasitol. 39: 365-76; Sabin (1941) supra.
[b]Donald & Roos (1994) Mol. Biochem. Parasitol. 63: 243-53.
[c]This study.

The RHΔHX strain was derived from strain RH by the targeted deletion of a 1.5 kb SalI fragment from the HXGPRT locus that deletes C-terminal amino acids necessary for enzyme activity (Donald, et al. (1996) supra). Parasites were maintained by serial passage in diploid human foreskin fibroblasts (HFF) at 36° C. (Fox & Bzik (2002) supra). HFF cells were cultured in Minimal Essential Medium Eagles (EMEM) with Earls Balanced Salt Solution (EBSS) and L-Glutamine (Lonza, Basel, Switzerland) and supplemented with 10% (v/v) newborn calf serum (Lonza) and antimycotic/antibiotic (GIBCO, INVITROGEN, Carlsbad, Calif.).

Primers. All primers (Integrated DNA Technologies, Coralville, Iowa) used in this study are listed in Table 6.

TABLE 6

| Primer name | Sequence (5'->3') | SEQ ID NO: |
|---|---|---|
| 5'CodA | CGCTAGATCTAAAATGTCGAATAACGCTTTACAAACAATT | 18 |
| 3'CodA | CGCTATGCATTCAACGTTTGTAGTCGATGGCTTC | 19 |
| 80F1 | GTGAAGACGACGGCTGAGCG | 20 |
| 80R15 | GTGAATTCCTCACCGGTTGAGACC | 21 |
| 80F15 | GGTCTCAACCGGTGAGGAATTCAC | 22 |
| 80R1 | GCCTCGAGCTATGACGTCGATTGCTAGCAGTGC | 23 |
| 80R16 | GAAGTACATTCAGGATCCTGGGTCA | 24 |
| 80F2 | CCTGAGGATATCCCAGCTGTACG | 25 |
| 80R25 | GAAGCGCGACAAGCTTCGCTG | 26 |
| 80F25 | CAGCGAAGCTTGTCGCGCTTC | 27 |
| 80R2 | GCTCTAGACAGTTGTTCATGCAGCTTCACAAGGT | 28 |
| 80R26 | GGAGCTCGAGCATATCTTCTGCCA | 29 |
| UPNF1 | CCGTTTAAACTTTGATTGTGCGTCCACAGGTACA | 30 |
| UPNR1 | GCGCTAGCGGTACCGAGAGCCAGTAGTGACAGAACGGT | 31 |
| UPRTFA2 | GCGCTAGCTCTAGAAGATCTTTTCATGTATCGGGGACT | 32 |
| UPRTR1 | GCCACGTGAAGGAGTTACCACCCATGACGAGC | 33 |
| pminiHXF | GTTTAAACGATAAGCTTGATCAGCACGAAACCTTG | 34 |
| pminiHFR | GTTTAAACCCGCTCTAGAACTAGTGGATCCC | 35 |
| F0 | GTCGACACCGGTTTCACCCTCA | 36 |
| R0 | GTCGACGCAAAAATGGAAGTACCGG | 37 |
| F50 | GCAGTACTTGTCAATCTTTCGCGACAAGCAC | 38 |
| R50 | GCGATATCCGTATTCTGGAAAGATTTCCGGTG | 39 |
| F100 | GCAGTACTATGTCCGCCTGAAGTCCTACC | 40 |
| R100 | GGCACGTGATCGGTATTCTCCTAGACGGC | 41 |
| F200 | GCAGTACTATGTGCATTCGCGACATTTGGAAG | 42 |
| R200 | GGCACGTGTCAAATGAATAGGCGGGAGTGG | 43 |
| F460 | GCAGTACTTACTTCGGCGAGGAGTTGCAC | 44 |
| R460 | GGCACGTGGGAAGACGGTAACCACAGTG | 45 |
| F620 | GCAGTACTTGAACGGCTATTGCCGCCT | 46 |
| R620 | GGCACGTGTCGCCTCTTGCTCTGCC | 47 |
| F900 | AAACCAGTACATCGTTAACTTCTGTCGT | 48 |
| R900 | GATGATTTTCTGACTTGGGAGCAACTG | 49 |
| B1F | GGAACTGCATCCGTTCCATG | 50 |
| B1R | TCTTTAAAGCGTTCGTGGTC | 51 |
| 80RTF | GGCACAAACAACTTGGAGGG | 52 |
| 80RTR | TTCAGAGCGGCATCAACCTG | 53 |
| EX801F | ACGTCTGTACGCGTACCGATACG | 54 |
| EX801R | GCGACAAGCTTCGCTGGATAGC | 55 |
| EX80F2 | TTCCAGCTTTGCGACGAAGTCG | 56 |

TABLE 6-continued

| Primer name | Sequence (5'->3') | SEQ ID NO: |
|---|---|---|
| EX80R2 | CTTCCAGCGACGTTGCCTGAG | 57 |
| EX80F3 | GAGAGGGCTGGTCGGAAAGTC | 58 |
| FX80R3 | ATCTGCCGATCGTACAATCAGTGA | 59 |
| D801F | CTGGGCAAAGCTTCAAGCGAGTG | 60 |
| D801R | GACAAGTCCGTCAATGGCGTCAC | 61 |
| 80FCX3 | CGCGAGACCCTTAGATCCGCA | 62 |
| 80RCX3 | TGCGCAGTGCTACACTAACTGG | 63 |
| HXDF1 | CGTCTGGATCGTTGGTTGCTGCTACG | 64 |
| HXDR2 | ACCACTTCTCGTACTATGGCCGGTCGA | 65 |
| HX1200 | CCACGATTTACGTCCTGTAGCTGC | 66 |
| CDXF1 | GTGAATACGGCGTGGAGTCGCTGCA | 67 |
| CDXR2 | CAGCAAGCGGAACAGGCGTGAGGT | 68 |
| TKXF1 | GGGCATGCCTTATGCCGTGACCGA | 69 |
| TKXR2 | CGCAGCCAGCATAGCCAGGTCCA | 70 |
| DUPRF1 | TGACGTCGGGTGCCTACGTTC | 71 |
| DUPRR1 | CGACAGCTGCACTCGAAGACAC | 72 |
| UPNF1 | CCGTTTAAACTTTGATTGTGCGTCCACAGGTACA | 73 |
| UPNXR1 | GCGCAGTTGACAAATTGTCTGAGG | 74 |
| 3'DHFRCXF | GTTGGCCTACGTGACTTGCTGATG | 75 |
| 3'CXPMUPR1 | ACAAACGCACCACATGCGTTCTG | 76 |
| 5'UPNCXF | GCGGAGGCCTTGAGGCTGA | 77 |
| 5'DHFRCXR | ACTGCGAACAGCAGCAAGATCG | 78 |
| CLUPRF1 | GGTGGGAGCAGCAAAGACAGCT | 79 |
| CPSDF1 | GGTCTTCAACAGCGCGCAGTC | 80 |
| CPSDR1 | CACTGTAAGCGTGTGCGGTACG | 81 |
| CPSEXF1 | GCTGGATTACGTCGTCACCAAGG | 82 |
| CPSEXR1 | CCAGATTCGATTCGGTGACGGAC | 83 |
| CPSCXF1 | CCGGTGAAATTCGTCAAGGAGCC | 84 |
| CPSCXR1 | AACACCAGCATTGCAGGTCTCAG | 85 |
| CPSCXR2 | AGTGCTCCTACGGGCGTTCATGA | 86 |

Plasmid Construction. The plasmids used in this study are listed in Table 7. All plasmids developed in this study were based on pCR4-TOPO (INVITROGEN), except for plasmids pC4HX1-1 and pC4, which were based on a pET41 vector.

TABLE 7

| Plasmid | Description of Insert |
|---|---|
| pDHFR-CD-TS[a] | Trifunctional DHFR-CD-TS |
| pDHFR-TK-TS[b] | Trifunctional DHFR-TK-TS |
| pminCAT/HX[c] | HXGPRT marker and CAT marker |
| pminiHX[d] | HXGPRT marker |
| pmHX4-3[e] | HXGPRT marker |
| pmin31-X2-4(−)[e] | HXGPRT marker and CD marker |
| pAN442[e] | Ku80 5.2 kb 5' target |
| pAN44X[e] | Ku80 5.2 kb 5' target, HXGPRT |
| pPN111[e] | Ku80 4.8 kb 3' target |
| pΔKu80HX[e] | Ku80 5' and 3' targets, HXGPRT (forward) |
| pΔKu80HXFCD[e] | HX (forward), Ku80 targets, CD (forward) |

TABLE 7-continued

| Plasmid | Description of Insert |
|---|---|
| pΔKu80B[e] | Ku80 targets, Ku80 cleanup vector, CD (forward) |
| pΔKu80TKFCD[e] | DHFR-TK-TS (forward), Ku80 targets, CD (forward) |
| pΔUPT-HXS[e] | HX (forward), UPT targets, 3' SmaI |
| pΔUPT-HXB[e] | HX (forward), UPT targets, 3' BglII |
| pΔUPNC[e] | UPT targets, UPT locus cleanup vector |
| pC4[e] | Functional CPSII cDNA |
| pC4HX1-1[e] | CPSII targets, downstream CPSII cDNA/HX |
| pHXH-0[e] | HX 1.5 kb SalI fragment, 3 bp 5', 3 bp 3' |
| pHXH-50[e] | HX 1.5 kb SalI fragment, 52 bp 5', 52 bp 3' |
| pHXH-120[e] | HX 1.5 kb SalI fragment, 116 bp 5', 117 bp 3' |
| pHXH-230[e] | HX 1.5 kb SalI fragment, 239 bp 5', 212 bp 3' |
| pHXH-450[e] | HX 1.5 kb SalI fragment, 446 bp 5', 461 bp 3' |
| pHXH-620[e] | HX 1.5 kb SalI fragment, 610 bp 5', 628 bp 3' |
| pHXH-910[e] | HX 1.5 kb SalI fragment, 922 bp 5', 896 bp 3' |

[a]Fox, et al. (1999) Mol. Biochem. Parasitol. 98: 93-103.
[b]Fox, et al. (2001) Mol. Biochem. Parasitol. 116: 85-8.
[c]Roos (1996) Curr. Top. Microbiol. Immunol. 219: 247-59; Roos, et al. (1994) Methods Cell. Biol. 45: 27-63.
[d]Donald, et al. (1996) supra; Donald & Roos (1998) Mol. Biochem. Parasitol. 91: 295-305.
[e]This study.

pmin31-X2-4(−). Plasmid pminCAT/HX (Roos (1996) supra; Roos, et al. (1994) supra) was found in restriction digests to contain two copies of the HXGPRT marker on 2 kb DNA fragments oriented in opposite directionality. Plasmid pminCAT/HX was reconstructed to contain only one copy of the HXGPRT marker in the (−) orientation by XhoI digestion of the vector and religation. Primers 5'CodA (made with a modified MET and second amino acid) and 3'CodA were used to PCR amplify the CD coding region from plasmid pDHFR-CD-TS (Fox, et al. (1999) supra). The PCR product was digested with BglII and NsiI and then ligated into BglII and PstI digested pminCAT/HX(−) to place the CD marker under control of the DHFR-TS gene 5' and 3' UTR's.

pAN442. A ~5.2 kb 5' Ku80 target that starts ~2.3 kb 5' of the Met codon was made by joining a 3 kb and a 2.2 kb PCR fragment. The 3 kb fragment was amplified using primers 80F1 and 80R15, and the 2.2 kb fragment was amplified using primers 80F15 and 80R1 by PCR from RH DNA template and fragment were TOPO cloned. The TOPO clones were AgeI and NotI digested and the 2.2 kb fragment was ligated into the 3 kb clone to create the 5.2 Kb 5' Ku80 target flank. Sequence analysis was conducted using primer 80R16.

pAN44X. Plasmid pAN442 was linearized by XhoI digestion and the 2 kb XhoI HXGPRT cassette obtained from pminCAT/HX was then ligated into the XhoI site at the 3' end of the 5.2 Kb 5' Ku80 fragment.

pPN111. The 4.8 kb 3' Ku80 target was made by joining a 2.8 kb (5') and a 2 kb PCR fragment. The 2.8 kb fragment was PCR amplified using primers 80F2 and 80R25, and the 2 kb fragment was PCR amplified using primers 80F25 and 80R2 from RH DNA template and PCR products were TOPO cloned. The TOPO clones were digested with HindIII and SpeI and the 2 kb fragment was isolated and ligated into the 2.8 kb clone to generate the 4.8 kb 3' Ku80 target flank. Sequence analysis was conducted using primer 80R26.

pΔKu80HXF. A 7.2 kb fragment was obtained by PmeI and NotI digestion of pAN44X and ligated into EcoRV and NotI digested pPN111 to place the HXGPRT marker in the forward orientation between the 5' and 3' target flanks.

pΔKu80HXFCD. A downstream cytosine deaminase (CD) selector was added to the 3' end of pDKu80HXF deletion targeting cassette by isolation of a 2.7 kb fragment containing the CD gene under control of DHFR 5' and 3' UTR after EcoRV and SpeI digestion of pmin31-x2-4(−), followed by ligation of this fragment to PmeI and SpeI digested pDKu80HXF.

pΔKu80B. The direct Ku80 replacement cleanup vector pDKu80B was made by simply digesting the vector pDKu80HXF with BamHI to remove the interior HXGPRT marker along with part of the targeting flanks to reducing the Ku80 5' targeting flank length to 3.3 kb and the 3' targeting flank length to 2.4 kb.

pΔKu80TKFCD. The Ku80 replacement vector to integrate the DHFR-TK-TS marker was made by digestion of pΔKu80HXFCD with NheI to remove the HXGPRT marker, followed by ligation to a 4.3 kb fragment containing the DHFR-TK-TS marker that was obtained by NheI and XbaI digestion of pDHFR-TK-TS (Fox, et al. (2001) supra). Clones were evaluated to identify the forward orientation of DHFR-TK-TS surrounded by 1.4 Kb 5' and 0.9 Kb 3' Ku 80 targeting flanks and a downstream 3' CD marker.

pΔUPNC. The UPRT 5' UTR (~1.1 kb 5' of the UPRT Met codon) was amplified by PCR using primer pair UPNF1 and UPNR1 from RHΔHX genomic DNA as template to obtain a 1.3 kb 5' target DNA fragment. After PCR, the product was TOPO cloned and digested with NheI and NotI. A 0.67 kb DNA fragment containing UPRT exon 7 and 3' UTR was similarly PCR amplified using primer pair UPRTFA2 and UPRTR1, TOPO cloned, digested with NheI and NotI, and ligated to the 5' 1.3 kb target clone.

pΔUPT-HXB. The HXGPRT marker was inserted in the forward orientation between the UPRT 5' and 3' target flanks by KpnI/SpeI digestion of pminiHX and ligation of the 1.95 kb KpnI and SpeI fragment into vector pΔUPNC that was linearized by KpnI and NheI digestion.

pΔUPT-HXS. A vector nearly identical to pΔUPT-HXB but with a trimmed 0.54 kb 3' target was constructed by digestion of pΔUPT-HXS with KpnI and SmaI, followed by ligation of a 1.8 kb fragment containing HXGPRT that was obtained by digestion of pminiHX with KpnI and MscI.

pmHX4-3. The 1.95 kb fragment containing the HXGPRT marker under DHFR 5' and 3' control was PCR amplified from pminiHX using primers pminiHXF and pminiHXR. The 1.95 kb fragment was TOPO cloned and the forward orientation designated as plasmid pmHX4-3.

pC4HX1-1. Plasmid pmHX4-3 was digested with PmeI and the 1.95 kb HXGPRT fragment was ligated in the forward orientation into the EcoRV digested pC4A plasmid that contains the CPSII cDNA.

pHXH-Series. DNA fragments containing a 1.5 kb SalI fragment that was deleted in strain RHΔHX were PCR amplified from RH DNA templates using different primer pairs (F0 and R0, F50 and R50, F100 and R100, F200 and R200, F460 and R460, F620 and R620, and F900 and R900, respectively) to extend the 5' and 3' flanks surrounding the SalI sites to varying lengths. PCR products were TOPO cloned and authenticity was verified by DNA sequencing. Plasmid pHXH-50, pHXH-120, pHXH-230, pHXH-450, pHXH-620, and pHXH-910 contained the 1.5 Sal fragment surrounded by ~50 bp flanks, 120 bp flanks, 230 bp flanks, 450 bp flanks, 620 bp flanks, and 910 bp flanks, respectively (see Table 7 for exact target DNA flank lengths). Plasmid pHXH-0 was equivalent to the original SalI fragment and had no flanks attached beyond the SalI site. All pHXH-series plasmids were oriented in the forward orientation relative to the unique 5' PmeI site in pCR4-TOPO.

Genomic DNA Isolation. For larger scale isolation of genomic DNA (≧25 cm$^2$) of HFF cell surface area), tachyzoites were isolated from freshly lysed HFF monolayers, filtered through 3 mm NUCLEPORE membranes (WHATMAN), and washed in PBS. For more rapid isolation of genomic DNA and analysis of putative parasite clones, parasites were grown in a single well of a 24-well plate until lysis of all HFF cells. The entire content of each well was pelleted, washed in PBS and genomic DNA purified. All genomic DNA purifications used the DNA Blood Mini Kit (QIAGEN, Valencia, Calif.).

PCR and Real-Time PCR. DNA amplification was performed using (1:1) mixture of Taq DNA polymerase and Expand Long Template PCR (Roche, Indianpolis, Ind.) in an EPPENDORF thermocycler (MasterCycler Gradient). PCR products were TOPO-TA cloned in pCR4-TOPO prior to DNA sequencing. BIGDYE Terminator cycle sequencing kits and an Applied Biosystems 7700 sequence detector were used for nucleotide sequencing. Real-time PCR was used to determine parasite genome equivalents in cloned knockouts and to estimate gene copy number at the Ku80 locus. Various concentrations of parasite DNA (1, 10, 100, 1000, and 10,000 pg) was amplified (in triplicate) with $T.$ $gondii$ B1 gene primer pairs B1F and B1R at 10 pMol of each primer per reaction (Kirisits, et al. (2000) $Int.$ $J.$ $Parasitol.$ 30:149-55). Amplification was performed by real-time fluorogenic PCR using SMARTMIX HM (CEPHEID, Sunnyvale, Calif.) on a CEPHEID Smart Cycler. Each reaction contained one lyophilized SMARTMIX bead, and 1:20,000 SYBR Green I (Cambrex Bio Science, Rockland, Me.). Parasite genome equivalents were determined in extrapolation from a standard curve using RH$\Delta$HX DNA. In parallel real-time PCR assays from the identical parasite DNA dilutions a second primer pair Ku80RTF and Ku80RTR was used in identical assays to determine parasite genome equivalents from a standard curve using RH$\Delta$HX DNA.

Transformation of $Toxoplasma$ $gondii$. For the purposes of the present invention, the terms transfection and transformation are used interchangeably to indicate the introduction of foreign DNA molecules in $T.$ $gondii$. The basic methods for transformation are known in the art (Donald & Roos (1993) $Proc.$ $Natl.$ $Acad.$ $Sci.$ $USA$ 90:11703-7; Kim, et al. (1993) $Science$ 262:911-4). The transfection protocol employed herein was a slight modification of that originally reported by Donald & Roos ((1994) supra). The tachyzoite concentration was adjusted to $4 \times 10^7$ tachyzoites ml$^{-1}$ in electroporation buffer (EB). Standard electroporation (model BTX600 electroporator) techniques were performed in 0.4 ml EB containing $1.33 \times 10^7$ freshly isolated tachyzoites and 15 mg of DNA, unless otherwise indicated.

Ku80 Knockout Strain Construction. Strain RH$\Delta$Ku80::HX was constructed from RH$\Delta$HX by integration of the HXGPRT marker using plasmid p$\Delta$Ku80HXFCD. Prior to transfection, plasmid p$\Delta$Ku80HXFCD was linearized by digestion with BlpI. Following transfection, parasites were grown for one day in the absence of selection then were selected in mycophenolic acid (25 mg ml$^{-1}$) and xanthine (50 mg ml$^{-1}$). Parasites were cloned after 10 days of selection by limiting dilution in 96-well trays (multiplicity of infection of 0.3 tachyzoites per well) in MPA selection. Six days later, wells were scored using a phase-contrast light microscope to identify wells containing a single plaque forming unit (PFU). Wells containing a single plaque were mixed to disperse tachyzoites and when the HFF cells lysed, tachyzoites were transferred and maintained in fresh HFF cells in 24-well trays until clones were evaluated for genotype. Negative selection experiments used 5-fluorocytosine (5FC) (50 mM) during parasite cloning steps in the presence of MPA selection. Verification of disruption of the Ku80 locus with the HXGPRT marker was performed by PCR with five sets of primers; Ku delta used D801F and D801R, Ku positive control used EX801F and EX801R, Ku real-time used 80RTF and 80RTR, HXGPRT used HXDF1 and HXDR2, and CD used CDXF1 and CDXR2. To estimate reversion frequency PFU assays were performed by infecting HFF cells with $2 \times 10^6$ or $4 \times 10^6$ tachyzoites of strain RH$\Delta$Ku80::HX in the presence of 6-thioxanthine (6TX) (200 mg ml$^{-1}$). Strain RH$\Delta$Ku80DHX was constructed from strain RH$\Delta$Ku80::HX (Table 5) by targeted deletion of the HXGPRT marker using BlpI linearized plasmid p$\Delta$Ku80B. Following transfection, parasites were continuously selected in 6TX (200 mg ml$^{-1}$) until PFU appeared in infected HFF monolayers. After PFU emerged, tachyzoites were cloned as described herein prior to genotype analysis. Verification of disruption of further disruption of the Ku80 locus and removal of the HXGPRT marker was performed by PCR with four sets of primers; Ku delta used EX801F and EX801R, Ku positive control used EX80F2 and EX80R2, HXGPRT used HXDF1 and HXDR2, and 3' crossover used 80F25 and 80RCX3.

Gene Replacement Frequency PFU Assays and Statistical Analysis. PFU assays, where equal volumes of parasites were independently placed into two different selection conditions for determining absolute numbers of PFU that develop under each growth condition, were used to determine the gene replacement frequency (GRF). Unless otherwise stated, PFU assays were performed by infection of fresh HFF monolayers in 25 cm$^2$ flasks and were left undisturbed for 7 days prior to fixing and COOMASSIE Blue staining of the HFF monolayers (Roos, et al. (1994) supra). To reduce pipetting error-induced variation in preparation of tachyzoite dilutions and during infection of monolayers in PFU assays, all dilutions and infections of flasks were performed by transferring parasites using the same dedicated volume calibrated 100 ml micropipettor. PFU assays were set up to capture a range of ~50 to 200 PFU per 25 cm$^2$ flask. Four replicate PFU flasks were prepared for each titration point and each selection condition. Each selection condition reports the frequency of a specific parasite phenotype in the tachyzoite population. GRF was calculated based on taking a ratio of the mean PFU that develop under each selection condition using the equation (s) provided. A student t-test analysis was used to calculate the standard error of the mean (SEM).

Replacements at the Ku80 Locus. Strain RH$\Delta$HX$\Delta$Ku80::DHFR-TK-TS was constructed from strain RH$\Delta$Ku80::HX by integration of the DHFR-TK-TS marker using plasmid p$\Delta$Ku80TKFCD. Prior to transfection plasmid p$\Delta$Ku80TKFCD was linearized by digestion with BlpI. Following transfection parasites were selected in pyrimethamine (PYR) (1 mM) and were cloned in continued selection to obtain individual PYR-resistant clones for genotype analysis. Verification of replacement of the HXGPRT marker in the Ku80 locus with the DHFR-TK-TS marker was performed by PCR with six sets of primers; HXGPRT delta used HXDF1 and HXDR2, Ku delta used EX80F2 and EX80R2, Ku positive control used EX80F3 and EX80R3, TK used TKXF1 and TKXR2, CD used CDXF1 and CDXR2, and 3' cross-over used 80FCX3 and 80RCX3. PFU assays were performed at 15 days after transfection and continuous selection in PYR to determine GRF based on the fraction of parasites with dual resistance to PYR (1 mM) and 6TX (200 mg ml$^{-1}$) compared to the fraction of parasites with resistance to PYR.

Replacements at the UPRT Locus. Strain RH$\Delta$Ku80$\Delta$UPT(S)::HX and strain RH$\Delta$Ku80$\Delta$UPT(B)::HX were constructed from RH$\Delta$Ku80$\Delta$HX by integration of the HXGPRT marker using plasmids p$\Delta$UPT-HXS and p$\Delta$UPT-HXB, respectively (Table 7). Prior to transfection, plasmid p$\Delta$UPT-HXS and p$\Delta$UPT-HXB were linearized by digestion with PmeI. Following transfection, parasites were selected in MPA and cloned to obtain individual MPA-resistant clones for genotype analysis. Verification of disruption of the UPRT locus was performed by PCR with four sets of primers; UPRT delta used DUPRF1 and DUPRR1, UPRT positive control used UPNF1 and UPNXR1, 5' cross-over used 5'UPNCXF and 5'DHFRCXR, and 3' cross-over used 3'DHFRCXF and 3'CXPMUPR1. PFU assays were performed at various times after transfection to determine the GRF based on the fraction of parasites that had dual resistance to MPA and 5-fluorodeoxyuridine (5FDUR) (5 mM) compared to the fraction of parasites that were resistant to MPA. Strain RHΔKu80ΔUPTΔHX was constructed from strain RHΔKu80ΔUPT::HX by targeted deletion of the HXGPRT marker using PmeI linearized plasmid pΔUPNC. Following transfection, parasites were continuously selected in 6TX (200 mg ml$^{-1}$) until PFU appeared. After PFU emerged, tachyzoites were cloned for genotype analysis. Verification of removal of the HXGPRT minigene at the UPRT locus was performed by PCR using primers 3'DHFRCXF and 3'CXPMUPR1, and CLUPF1 and 3'CXPMUPR1. 6TX resistant clones were also phenotypically verified to be resistant to 5FDUR in PFU assays.

Replacements at the CPSII Locus. Strain RHΔKu80ΔCPSII::cpsII/HX was constructed from RHΔKu80ΔHX by integration of the HXGPRT marker using plasmid pC4HX1-1. Prior to transfection, plasmid pC4HX1-1 was linearized by digestion with SmaI. Following transfection, parasites were selected in MPA and cloned for genotype analysis. Verification of deletion of the endogenous CPSII locus and replacement with a functional cpsII cDNA was performed by PCR with four set of primers; delta CPSII intron used CPSDF1 and CPSDR1, CPSII exon used CPSEXF1 and CPSEXR1, 5' cross-over used CPSCXF1 and CPSCXR1, and 3' cross-over used 3'DHFRCXF and CPSCXR2.

Chromosomal Healing of HXGPRT. Strain RHΔKu80 was constructed from RHΔKu80ΔHX by integration of a 1.5 kb SalI fragment present on pHXH plasmids with varying lengths of added flanking target DNA. Prior to transfection, pHXH-series plasmids were linearized by digestion with PmeI. Following transfection, parasites were selected in MPA and cloned for genotype analysis. Verification of chromosomal healing of HXGPRT was performed by PCR with primers HXDF1 and HXDR2 and 5' cross-over primers HXF1200 and HXDR2. The frequency of chromosomal healing of the HXGPRT locus as a function of homology targeting length was determined in PFU assays. Following transfection of strain RHΔHX or strain RHΔKu80ΔHX, the entire contents and first infection medium wash of the transfection cuvette were transferred into a single 150 cm$^2$ flask of HFF cells in 30 ml infection medium. MPA selection was initiated at 24 hours post-transfection. PFU were scored eight days after transfection. To determine the homologous recombination (HR) rate based on a double cross-over at the HXGPRT locus, each pHXH series plasmid was transfected in five independent healing experiments and the mean PFU determined. The HR rate was then calculated based on the assumption that the mean PFU that developed using the pHXH-910 plasmid was 100% of the HR rate. To determine the mean HR frequency, the surviving fraction of parasites was determined in each transfection experiment by serial dilution of tachyzoites after transfection and determining PFU in triplicate 25 cm$^2$ flasks of HFF cells at various dilutions of the parasite population in the absence of MPA. Typically, approximately $0.6 \times 10^6$ to $1.5 \times 10^6$ parasites survived electroporation of $1.33 \times 10^7$ tachyzoites. To determine the HR rate as a function of DNA concentration, the pHXH-620 plasmid was linearized with PmeI and various concentrations of DNA were transfected to determine primary PFU in 150 cm$^2$ HFF flasks as described herein. The DNA concentration-dependence was determined in two independent experiments. To determine the HR rate of circular DNA, 15 mg undigested pHXH-620 plasmid was transfected into strain RHΔHX or RHΔKu80ΔHX in three independent transfection experiments for each strain.

Parasite Growth Rate. Tachyzoite growth rate was determined by scoring 50 randomly selected vacuoles according to conventional methods (Fox & Bzik (2002) supra). Following infection of HFF cells at a moi of 0.1 for 2 hours, monolayers were washed twice in PBS and infection medium returned. Tachyzoites per vacuole were scored at 36 hours post-infection using light microscopy.

Sensitivity to Chemical Mutagens and Phleomycin. The sensitivity of *T. gondii* strains to chemical mutagens or phleomycin was determined in PFU assays. Sensitivity to N-nitroso-N-ethylurea (ENU) (Sigma, St. Louis, Mo.) was determined by treatment of replicating intracellular parasites essentially as described in the art (Pfefferkorn & Pfefferkorn (1979) *J. Parasitol.* 65:364-70; fefferkorn & Pfefferkorn (1976) supra). Briefly, HFF cells infected ~24 hours prior to chemical treatment at a multiplicity of infection of 0.3 were treated for 4 hours with various concentrations of ENU in serum-free EMEM medium. After treatment, parasites were syringe-released, washed in PBS, and various dilutions were prepared to infect duplicate flasks of HFF monolayers in PFU assays to determine the surviving fraction of treated parasites relative to untreated controls. Etoposide (Sigma) sensitivity was determined by continuous treatment of infected monlayers in PFU assays as previously described (Shaw, et al. (2001) *Microbes Infect.* 3:351-62). Sensitivity to the antibiotic phleomycin (Sigma) was determined on extracellular parasites (Messina, et al. (1995) *Gene* 165:213-7), except PFU assays were used rather than uracil incorporation to measure survival. Briefly, tachyzoites from freshly lysed HFF monolayers were filtered through a NUCLEPORE membrane, washed in PBS, and resuspended in serum-free EMEM at a concentration of 10$^7$ tachyzoites ml$^{-1}$. Tachyzoites were treated for 4 hours at 36° C. in a humid CO$_2$ chamber with various concentrations of phleomycin, or were untreated. Following treatment, parasites were washed in PBS and various dilutions were prepared to infect duplicate HFF monolayers in PFU assays to determine the surviving fraction of treated parasites relative to untreated controls. Survival experiments with ENU, etoposide, and phleomycin were performed twice.

Sensitivity to γ-Irradiation. Sensitivity to γ-irradiation was determined by treatment of tachyzoites with various doses of ionizing radiation that were generated in a 2,000 Curie JL Shepard Cesium (Cs137 gamma) Irradiator. Tachyzoites were isolated from freshly lysed HFF monolayers, filtered through NUCLEPORE membranes, and washed in PBS to prepare a solution of 10$^7$ tachyzoites ml$^{-1}$. Following irradiation of tachyzoites, various dilutions of parasites were prepared to infect triplicate HFF monolayers in PFU assays to determine the surviving fraction of treated parasites relative to untreated controls. Survival experiments involving g-irradiation were performed twice.

Virulence Assays. Adult, 6-8 week old C57Bl/6 mice were obtained from Jackson Labs and mice were maintained in TECNIPLAST SEALSAFE mouse cages on vent racks. All mice were cared for and handled according to approved Institutional animal care and use committee guidelines. Tachyzoites were isolated from freshly lysed HFF monolayers and were purified by filtration through sterile 3 mm NUCLEPORE membranes (WHATMAN). Tachyzoites were washed in PBS, counted in a hemocytometer to determine parasite number, and a PBS solution prepared with 1000 tachyzoites per ml. Groups of four mice were injected intraperitoneally (i.p.) with 0.2 ml (200 tachyzoites) and mice were then monitored daily for degree of illness and survival. Immediately following i.p. injections, aliquots of 0.2 ml of the tachyzoite solution used for infecting mice were plated on HFF monolayers and PFU were scored seven days later to determine the PFU to physical tachyzoite ratio in each parasite preparation injected into mice. PFU to tachyzoite ratios ranged between ~0.32 to 0.55 for each preparation of tachyzoites. The virulence assays were performed twice.

Generation of *T. gondii* Gene Deletion Strains RHΔKu80::HX and RHΔKu80ΔHX. To look for potential components of the NHEJ pathway in *T. gondii*, the ToxoDB genome database was scanned for potential Ku70 and Ku80 genes. BLASTP of the Ku70 (mus51) and Ku80 (mus52) proteins of *Neurospora crassa* identified *T. gondii* homologs 50.m03211 and 583.m05492 (expect values of 1.4e-13 and 1.9e-5, respectively). The Ku70 (50.m03211) and Ku80 (583.m05492) homologs were predicted to encode proteins of 859 and 939 amino acids, respectively, and are expressed in all three lineages of *T. gondii*. Further analysis of the putative Ku80 locus revealed expressed sequence tags (TgDT.545521.tmp, WO5879) that suggested the 998 amino acid protein predicted by TgTigrScan_2322 was a more likely prediction. The predicted Ku70 and Ku80 homologs in *T. gondii* were markedly enlarged proteins in comparison to Ku proteins described from other species. Genes encoding enlarged proteins appear to be a common feature of parasites from the phylum Apicomplexa (Flores, et al. (1994) *Mol. Biochem. Parasitol.* 68:315-8; Fox & Bzik (2003) supra; Fox, et al. (1993) *Mol. Biochem. Parasitol.* 61:37-48). ClustalW alignments between Ku70 or Ku80 proteins from *T. brucei, L. major, S. cerevisiae, N. crassa, A. oryzae, Arabidopsis thaliana*, and *Homo sapiens* indicated that only 0.9% and 0.4%, respectively, of the amino acid residue positions of the predicted *T. gondii* Ku70 or Ku80 proteins were identically conserved between all of these organisms. See, e.g., FIG. 6.

Figure 8A:
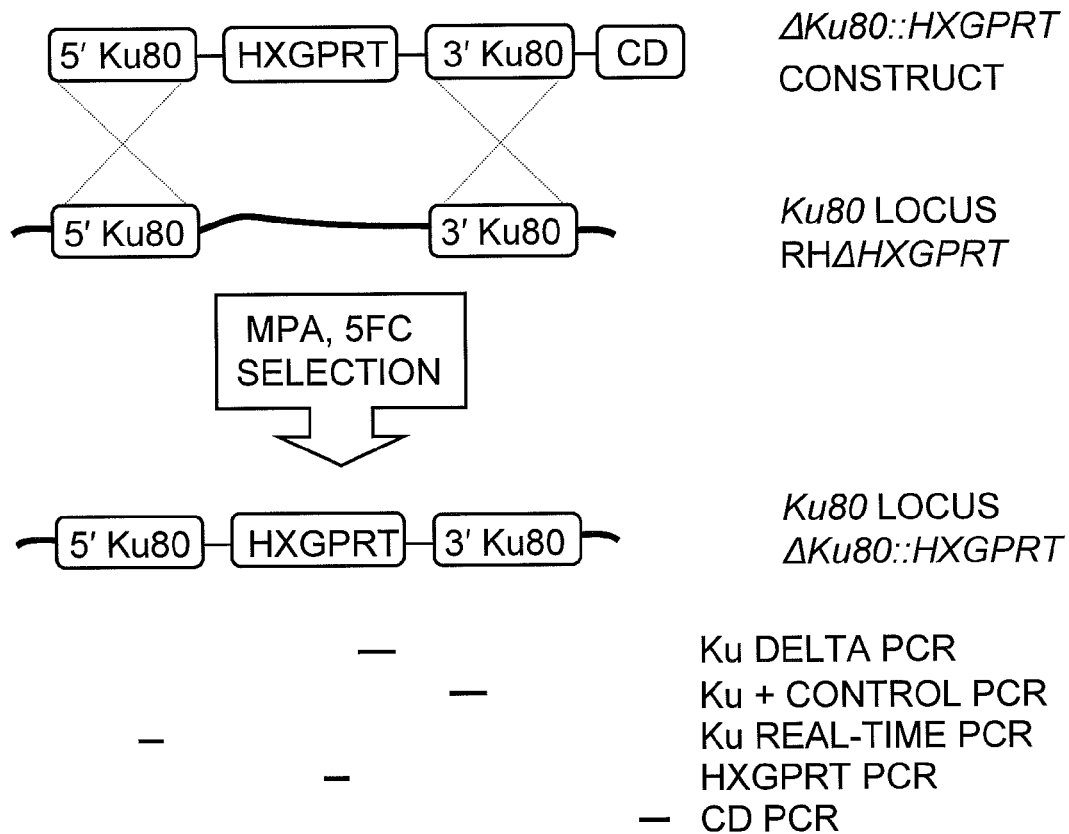
FIG. 8A shows the strategy for disrupting the Ku80 gene using integration of the HXGPRT marker into strain RHDHX and positive (+) selection in MPA and xanthine, or negative selection against the downstream cytosine deaminase marker in MPA/xanthine/5-fluorocytosine. Primer pairs to verify genotype are depicted. The parental strain RHΔHX is positive for the Ku delta (538 bp) and Ku positive control primers (639 bp), and negative for HXGPRT (270 bp) and CD (226 bp). A targeted Ku80 knockout is positive for the Ku positive control primers and HXGPRT, and is negative for Ku delta and CD.

The Ku80 knockout strategy used targeting plasmid pΔKu80HXFCD that contained ~5 Kb of 5' and 3' target DNA flanks surrounding a functional HXGPRT minigene and a downstream cytosine deaminase (CD) gene for negative selection in 5-fluorocytosine (5FC) (Fox, et al. (1999) supra). Circular or linearized pΔKu80HXFCD was transfected into strain RHΔHX and parasites were selected in mycophenolic acid (MPA)+xanthine (X) (FIG. 8A). MPA-resistant parasite clones were isolated and analyzed by PCR using a deletion primer pair and control expressed primer pair to test for the targeted deletion. Circular plasmid produced no Ku80 knockouts (0/36), while linearized plasmid produced 11/36 clones that showed a correct Ku80 positive control product and revealed the absence of a PCR product from the deleted Ku80 region, identifying clones disrupted in Ku80. Real-time PCR analysis of Ku80 gene copy number indicated that ~82% of the Ku80-disrupted clones contained a single copy of the Ku80 3' target DNA. PCR from HXGPRT primer pairs was positive and PCR from CD primer pairs was negative. These results indicate that the HXGPRT marker was inserted into a correctly disrupted Ku80 locus in clones 1 to 5, indicating the genotype of the RHΔKu80::HXGPRT strains as ΔKu80::HXGPRT (Table 5).

A downstream CD marker on plasmid pΔKu80HXFCD was tested in a negative selection strategy using 5FC in an attempt to enrich for desired Ku80 knockouts. Transfected parasites were initially selected in MPA+X for 10 days, and subsequently cloned in MPA+X+5FC to counter select against the downstream CD gene. In this experiment, it was observed that 6/6 analyzed clones were Ku80 knockouts.

Figure 8B:
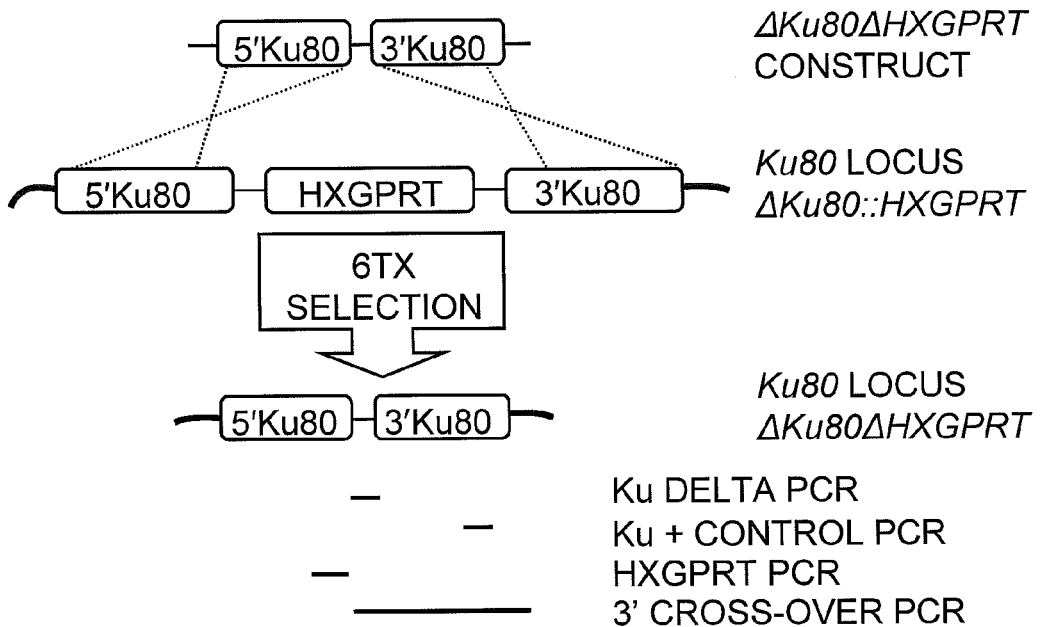
FIG. 8B shows the cleanup of the Ku80 locus. The HXGPRT marker was removed from the Ku80 locus using the strategy depicted with negative selection in 6-thioxanthine (6TX) after transfection of strain RHΔKu80::HX with plasmid pΔKu80B. Primer pairs to verify genotype are depicted. The parental strain RHΔKu80::HX is positive for the Ku delta (538 bp) and Ku positive (+) control primers (373 bp), and a targeted Ku80 knockout is positive for the Ku positive control primers and is negative for the 538 bp Ku delta primer pair product.

Clones of strain RHΔKu80::HX were examined for growth in 6-thioxanthine (6TX) (Pfefferkorn, et al. (2001) *Exp. Parasitol.* 99:235-43), and each clone uniformly exhibited no evidence of spontaneous reversion to a 6TX resistant phenotype indicating a low spontaneous reversion frequency ($<<10^{-6}$). Consequently, recovery of the HXGPRT marker from the Ku80 locus appeared feasible via a targeted deletion strategy. Clones of strain RHΔKu80::HX were transfected with plasmid construct pΔKu80B and parasites were negatively selected in 6TX to isolate 6TX resistant clones. Nine 6TX resistant clones obtained from each transfection were analyzed by PCR. Each clone produced a correct positive control PCR product, but failed to produce a PCR product corresponding to the deleted region in the targeting plasmid that is present in strain RHΔKu80::HX. PCR also revealed the absence of the HXGPRT marker and PCR primers produced a correct product size (~2.9 kb) in a 3' crossover PCR, and DNA sequencing of the 3' crossover PCR products revealed correct targeted integration had occurred at the Ku80 locus, cleanly deleting the HXGPRT marker (FIG. 8B). The genotype ΔKu80ΔHXGPRT of these 6TX-resistant parasite clones was identified with a 100% frequency. The *T. gondii* strain RHΔKu80::HX is $MPAR^R$ and $6TX^S$, whereas strain RHΔKu80ΔHX is $MPA^S$ and $6TX^R$ (Table 5).

Growth, Virulence, and Sensitivity of *T. gondii* Strains RHΔKu80::HX and RHΔKu80ΔHX to DNA Damaging Agents. Disruption of Ku genes or nonhomologous end-joining (NHEJ) in many fungal organisms has no significant effect on a large number of phenotypes that have been examined (growth, morphology, development, conidiation, sporulation, virulence, pathogenicity, mating, fertility, telomere length, etc.) (Chang (2008) *Lett. Appl. Microbiol.* 46:587-92; da Silva Ferreira, et al. (2006) *Eukaryot. Cell* 5:207-11; Goins, et al. (2006) *Fungal Genet. Biol.* 43:531-44; Haarmann, et al. (2008) *Fungal Genet. Biol.* 45:35-44; Kooistra, et al. (2004) *Yeast* 21:781-92; Krappmann, et al. (2006) *Eukaryot. Cell.* 5:212-5; Lan, et al. (2008) *Curr. Genet.* 53:59-66; Maassen, et al. (2008) *FEMS Yeast Res.* 8:735-43; Meyer, et al. (2007) *J. Biotechnol.* 128:770-5; Nayak, et al. (2006) *Genetics* 172:1557-66; Nielsen, et al. (2008) *Fungal Genet. Biol.* 45:165-70; Ninomiya, et al. (2004) *Proc. Natl. Acad. Sci. USA* 101:12248-53; Poggeler & Kuck (2006) *Gene* 378:1-10; Takahashi, et al. (2006) *Mol. Genet. Genomics* 275:460-70; Takahashi, et al. (2006) *Biosci. Biotechnol. Biochem.* 70:135-43; Ueno, et al. (2007) *Eukaryot. Cell* 6:1239-47; Villalba, et al. (2008) *Fungal Genet. Biol.* 45:68-75). However, in certain fungal organisms disruption of Ku70 or Ku80 induces an increased sensitivity to DNA damaging agents, particularly to agents that induce double-strand DNA breaks (Goins, et al. (2006) supra; Haarmann, et al. (2008) supra; Kooistra, et al. (2004) supra; Meyer, et al. (2007) supra). The sensitivity to various DNA damaging agents was examined in Ku-deficient *T. gondii*. Tachyzoite growth rate in HFF cells in vitro, as well as sensitivity to ENU and etoposide were unchanged between strains RHΔKu80::HX and RHΔKu80ΔHX compared to RHΔHX or RH. The high virulence of type I strains was also retained in the Ku80 knockout mutants. On the other hand, strains RHΔKu80::HX and RHΔKu80ΔHX were markedly more sensitive to DNA damaging agents phleomycin and γ-irradiation that induce double-strand DNA breaks. Relative to strain RHΔHX, the sensitivity to phleomycin was increased ~10-fold, while sensitivity to γ-irradiation was increased, remarkably, by more than two orders of magnitude in the Ku80 knockout genetic background. Interestingly, the sensitivity of *T. gondii* parental strain RHΔHX to γ-irradiation (LD90 ~30 Gy) was significantly greater than observed in yeasts such as *K. lactis* (LD90~400 Gy) (Kooistra, et al. (2004) supra).

Figure 9:
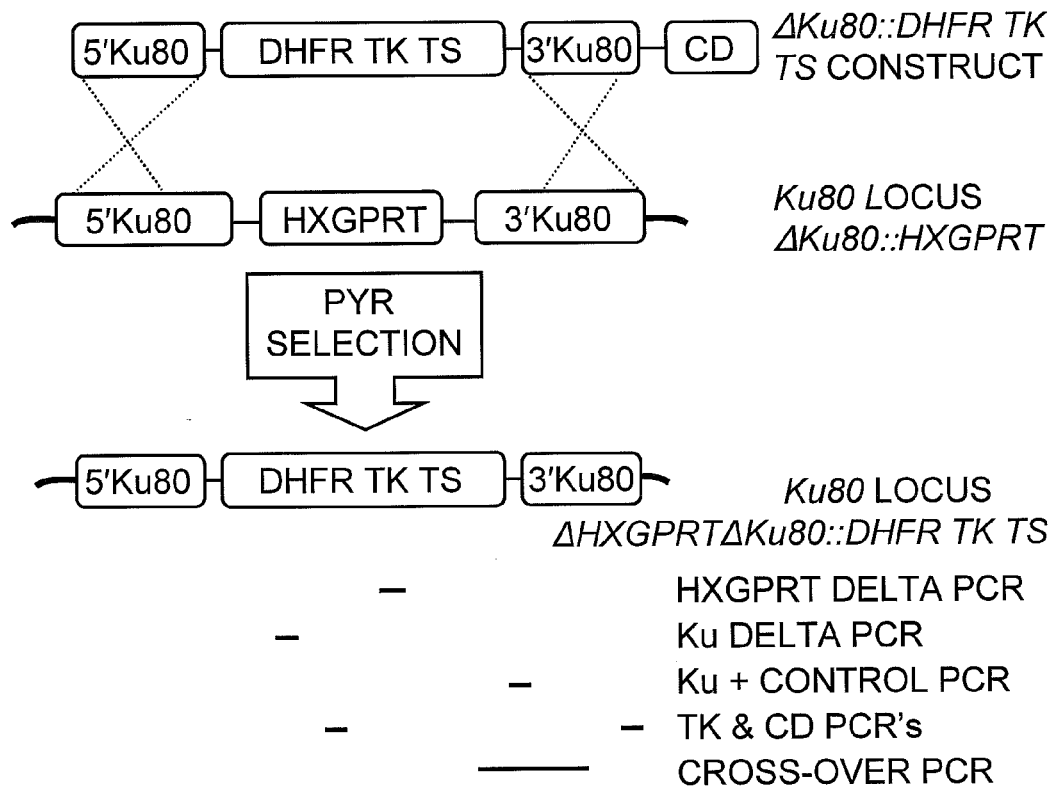
FIG. 9 shows a strategy for gene replacements at the Ku80 locus. Show is the replacement of the HXGPRT marker in strain RHΔKu80::HX with the DHFR-TK-TS marker. PCR primer pairs were used to verify genotype of pyrimethamine resistant clones isolated after transfection and selection.

Gene Replacement Frequency at the Ku80 Locus in Strain RHΔKu80::HX. A simple plaque assay strategy was devised to specifically measure the percentage of gene replacement events via double cross-over at the Ku80 locus versus random insertion of a plasmid episome via nonhomologous recombination or integration via homologous recombination after a single cross-over. This strategy involved the targeted insertion of the trifunctional DHFR-TK-TS gene (Fox, et al. (2001) supra; Fox & Bzik (2002) supra) with corresponding loss of the HXGPRT gene at the Ku80 locus in strain RHΔKu80::HX (FIG. 9). Plaque assays using equal numbers of input parasites plated in medium containing pyrimethamine (PYR) (which measured the total number of gene replacements plus episome insertions via nonhomologous recombination), or plated in medium containing PYR/6TX (which specifically measured gene replacement at the Ku80 locus) determined the specific frequency of gene replacement events at the Ku80 locus. Using target DNA flanks of only 1.3 and 0.9 Kb carried on targeting plasmid pΔKu80TKFCD, the efficiency of gene replacement at the Ku80 locus was determined to be 97% (97±2.3) when assayed 15 days after continuous selection in PYR. Parasites resistant to PYR/6TX were cloned and clones were then examined in PCR verification assays. The predicted genotype ΔHXGPRTΔKu80::ΔHFRTKTS was uniformly observed in PCR assays when using primer pairs to assay for the expanded Ku80 deletion, a Ku80 positive control, the presence of TK, the absence of both HXGPRT and CD, and the presence of correct size cross-overs. In contrast, strain RHΔKu80::HX transfected with PmeI-linearized vector control pCR4-TOPO produced a 0% GRF.

Gene Replacement Frequency at the Uracil Phosphoribosyltransferase Locus in Strain RHDKu80DHX Compared to Parental Strain RHDHX. The gene replacement strategy using the trifunctional DHFR-TK-TS genetic marker did not permit direct comparison of the gene replacement percentage efficiency between the Ku80 mutant and parental backgrounds. To more precisely measure the increase in gene targeting efficiency in Ku80 knockouts, an assay based on targeting the uracil phosphoribosyltransferase (UPRT) locus was employed. Loss of UPRT function leads to resistance to 5-fluorodeoxyuridine (5FDUR) (Donald & Roos (1998) supra; Donald & Roos (1995) *Proc. Natl. Acad. Sci. USA* 92:5749-53; Pfefferkorn (1978) *Exp. Parasitol.* 44:26-35). A fixed 5' target DNA flank of 1.3 Kb and either a 0.54 Kb (S) or a 0.67 Kb (B) target DNA flank was used in the UPRT assay. The UPRT target DNA flanks surrounded a functional HXGPRT gene and defined a lethal deletion of UPRT. In a bulk population of transfected parasites selected in MPA/X, the frequency of gene replacement was determined at different time-points after transfection by plating equal numbers of parasites in MPA/X or MPA/X/5FDUR. The frequency of gene replacement at the UPRT locus in strain RHΔKu80ΔHX was nearly 100% when assayed at 20 days post-transfection (Table 8). By contrast, the efficiency in the parental strain RHDHX was less than 0.4%. At the UPRT locus, the relative efficiency of gene replacement was enhanced by ~300 to 1200-fold in strain RHDKu80DHX compared to the efficiency measured in parental strain RHDHX.

TABLE 8

| Strain | Plasmid | Day assayed | Gene replacement (%) at the UPRT locus | |
|---|---|---|---|---|
| | | | Experiment 1 | Experiment 2 |
| RHΔHX | pUPNHXS | 10 | 0.15 | 0.04 |
| RHΔHX | pUPNHXS | 14 | 0.19 | 0.07 |
| RHΔHX | pUPNHXS | 20 | 0.18 | 0.08 |
| RHΔHX | pUPNHXB | 10 | 0.26 | 0.20 |
| RHΔHX | pUPNHXB | 14 | 0.31 | 0.29 |
| RHΔHX | pUPNHXB | 20 | 0.33 | 0.26 |
| RHΔKu80ΔHX | pUPNHXS | 10 | 72.6 | 36.4 |
| RHΔKu80ΔHX | pUPNHXS | 14 | 91.2 | 82.9 |
| RHΔKu80ΔHX | pUPNHXS | 20 | 102.3 | 97.1 |
| RHΔKu80ΔHX | pUPNHXB | 10 | 82.8 | 90.0 |
| RHΔKu80ΔHX | pUPNHXB | 14 | 97.1 | 96.3 |
| RHΔKu80ΔHX | pUPNHXB | 20 | 99.2 | 100.4 |

MPA-resistant parasites emerging from the RHΔKu80ΔHX transfections were cloned from the MPA-selected population(s) and the presence of clones with the non-reverting genotype ΔKu80ΔUPRT::HXGPRT were uniformly confirmed in PCR assays. A cleanup vector pΔUPNC containing 5' and 3' UPRT target DNA flanks but no HXGPRT marker was used to remove the integrated HXGPRT marker from the UPRT locus in a clone of strain RHΔKu80ΔUPT (B)::HX. Following transfection with plasmid pΔUPNC, negative selection in 6TX, and subcloning in 6TX, cloned strains RHΔKu80ΔUPTΔHX were isolated and verified to have the genotype ΔKu80ΔUPRTΔHXGPRT in PCR assays using HXGPRT primer pairs to show the absence of the HXGPRT minigene.

Functional Gene Replacement at the Carbamoyl Phosphate Synthetase II Locus. Previous work on disruption of the essential carbamoyl phosphate synthetase II (CPSII) locus in strain RH revealed a very low (~0.2%) frequency of homologous recombination using ~3 kb target DNA flanks (Fox & Bzik (2002) supra). Targeting efficiency at the CPSII locus was examined in strain RHΔKu80ΔHX using a slightly different strategy. Target flanks of 1.5 kb 5' and a ~0.8 kb 3' target on plasmid pC4HX1-1 were used to delete the endogenous CPSII gene and replace it with a functional CPSII cDNA and a downstream HXGPRT. Following transfection and selection in MPA/X, 12 MPA-resistant clones were evaluated in PCR assays to determine whether the endogenous CPSII locus was intact. In 12 of 12 MPA-resistant clones, each clone failed to produce a PCR product from an intron primer pair, and using a primer pair seated in neighboring exons produced a PCR product corresponding to cDNA rather than originating from the endogenous CPSII locus, indicating successful gene replacement at the CPSII locus in strain RHΔKu80ΔHX. Sequencing of correct size 5' and 3' crossover PCR products revealed correct integration of the targeting plasmid at the CPSII locus, verifying the genotype as ΔKu80ΔcpsII::cpsII/HX (Table 5).

Figure 10A:
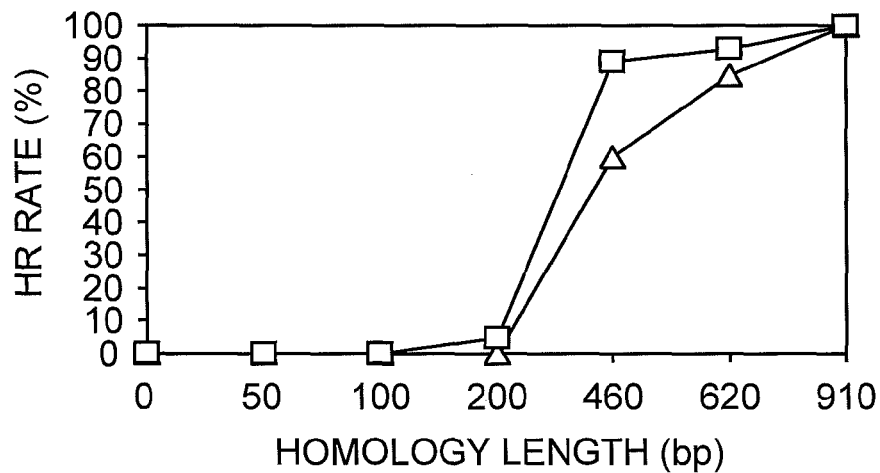
FIG. 10A shows homologous recombination rate (HR) as a function of target DNA flank length in strain RHΔHX (triangles) or strain RHΔKu80ΔHX (squares).
Figure 10B:
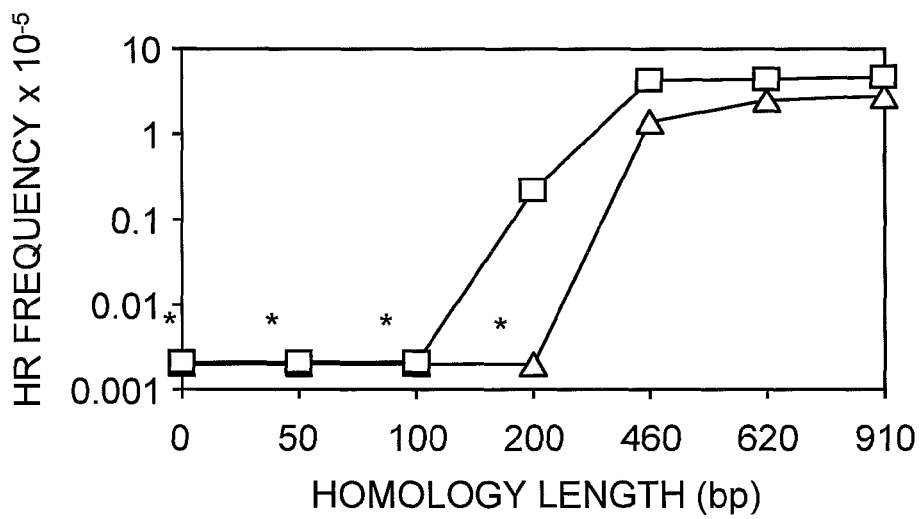
FIG. 10B shows HR rate determined as a percentage of the parasite population surviving transfection (assayed without MPA).

Homologous Recombination Rate in *T. gondii* is Dependent on Target DNA Flank Homology Length, DNA Concentration, and DNA Conformation. The gene targeting experiments described herein at the Ku80, the UPRT, and the CPSII loci demonstrated a marked increase in apparent gene replacement frequency, but these experiments did not specifically address the relative efficiency of homologous recombination in the Ku80 knockouts compared to the parental strain. To specifically measure the frequency of homologous recombination in *T. gondii*, a direct plaque forming unit reporter assay was developed based on previously reported fundamental studies of HXGPRT (Donald, et al. (1996) supra;

Donald & Roos (1998) supra; Pfefferkorn & Borotz (1994) *Exp. Parasitol.* 79:374-82; Pfefferkorn, et al. (2001) supra). The strategy herein heals a disrupted HXGPRT genetic locus by a double cross-over homologous recombination mediated via target DNA flanks of varying length attached to a 1.5 Kb SalI fragment that is deleted in strain RHΔHX, and specifically measures the efficiency of gene replacement within a disrupted HXGPRT background by restoring parasite growth rate in MPA selection. Because each of the targeting plasmids contains a truncated and non-functional HXGPRT gene, no PFU can arise from nonhomologous integration events. The targeting efficiency of DNA flank lengths of 0, 50, 120, 230, 450, 620, and 910 bp carried on pHXH plasmids was examined in parental strain RHΔHX as well as strain RHΔKu80ΔHX. No gene replacement events were detected in strain RHΔHX using 230 bp target DNA flanks. In contrast, strain RHΔKu80ΔHX exhibited a detectable frequency of gene replacement, but the overall efficiency was reduced approximately ~22-fold compared to target DNA flanks of 450 bp or more (FIG. 10A). No gene replacement events were detected when using target DNA flanks of 100 bp or less in any strain. On a per (surviving transfection) parasite basis, the efficiency of gene replacement was ~2-fold higher in strain RHΔKu80ΔHX than in strain RHΔHX (FIG. 10B). These results define target DNA flank requirements for homologous recombination in *T. gondii*, and also show the major mechanism of increased gene replacement frequency in the Ku-deficient genetic background is due primarily to disruption of NHEJ rather than to any marked increase in the rate of homologous recombination.

Figure 10C:
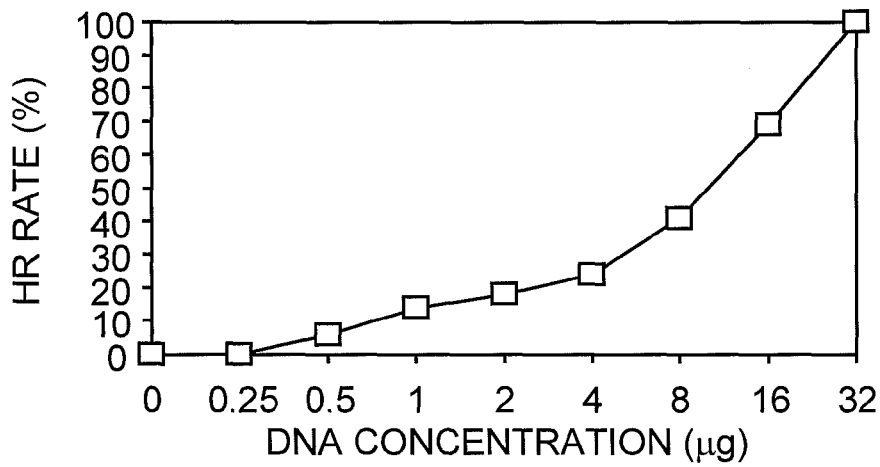
FIG. 10C shows DNA concentration dependence of HR rate in *T. gondii*.

The efficiency of gene replacement as a function of DNA concentration was measured in the same HXGPRT gene healing plaque assay. Transfection of strain RHΔKu80ΔHX with 32, 16, 8, 4, 2, 1, 0.5, 0.25, or 0 mg of the 1.5 Kb SalI fragment clone containing the ~620 bp target DNA flanks demonstrated that the efficiency of gene replacement was dependent on DNA concentration (FIG. 10C). DNA conformation (linear versus circular molecules) was similarly examined. No gene replacement events were detected at the HXGPRT locus using circular targeting DNA in strain RHDHX. In contrast, a detectable frequency was observed in strain RHΔKu80ΔHX, although the efficiency was reduced approximately ~20 to 25-fold compared to linear DNA.

EXAMPLE 5

NHEJ-Deficient *T. Gondii* as a Genetic Background for Gene Replacements and Exogenous Gene Expression As disclosed herein, the RHΔKu80 strain was used as a genetic background for the replacement of the open reading frames for UPRT and CPSII. To further illustrate the use of the NHEJ-Deficient *T. gondii* as a genetic background for gene replacements or exogenous protein expression, additional gene replacements were conducted in the RHΔKu80 genetic background. The following strains were generated.

RHΔKu80ΔOMPDC::HX (Genotype ΔKu80ΔOMPDC::HXGPRT), wherein the OMPDC gene (locus i.d. 55.m04842) encoding orotidine 5'-monophosphate decarboxylase was knocked out. This strain exhibited a severe pyrimidine auxotroph and was extremely attenuated in mice. RHΔKu80ΔOMPDC (Genotype ΔKu80ΔOMPDC) also exhibited a severe pyrimidine auxotroph and was extremely attenuated in mice. Thus, these strains find application as vaccine strains themselves or in combination with any other gene knock outs.

RHΔKu80ΔOMPDCΔUP::HX (Genotype ΔKu80ΔOMPDCΔUP::HXGPRT), wherein the OMPDC gene and UP gene were knocked out. This strain exhibited a severe pyrimidine auxotroph and was extremely attenuated in mice. Thus, this strain finds application as a vaccine strain alone or in combination with any other gene knock out.

RHΔKu80ΔOPRT::HX (Genotype 6Ku80ΔOPRT::HXGPRT), wherein the OPRT gene (locus i.d. 55.m04838) encoding orotate phosphoribosyltransferase was knocked out. This strain exhibited a severe pyrimidine auxotroph. RHΔKu80ΔOPRT (Genotype ΔKu80ΔOPRT) also exhibited a severe pyrimidine auxotroph.

RHΔKu80ΔUP::HX (Genotype ΔKu80ΔUP::HXGPRT), wherein the UP gene (locus i.d. 583.m00630) encoding uridine phosphorylase was knocked out. This strain, as well as RHΔKu80ΔUP (Genotype ΔKU80ΔUP), find application in studies on *C. parvum, T. gondii* and other pyrimidine pathways.

RHΔKu80ΔOPRTΔOMPDC::HX (Genotype ΔKu80ΔOPRTΔOMPDC::HXGPRT) and RHΔKu80ΔOPRTΔUP::HX (Genotype ΔKu80ΔOPRTΔUP::HXGPRT) strains, which respectively have the OMPDC and OPRT genes, or OPRT and UP simultaneously knocked out exhibit a severe pyrimidine auxotroph.

RHΔKu80ΔIMPDH::HX (Genotype ΔKu80ΔIMPDH::HXGPRT), wherein the IMPDH gene (locus i.d. 44.m00049) encoding inosine 5'-monophosphate dehydrogenase was knocked out. This strain exhibited a significant reduction in parasite growth rate.

RHΔKu80ΔPNP::HX (Genotype ΔKu80ΔPNP::HXGPRT) and RHΔKu80ΔPNP (Genotype ΔKu80ΔPNP), wherein the PNP gene (locus i.d. 542.m00227) encoding purine nucleoside phosphorylase was knocked out. While these strains did not exhibit an apparent phenotype, this enzyme is a drug target in human disease such as cancer. As such, this strain could find application in drug and vaccine development.

RHΔKu80ΔPNPΔIMPDH::HX (Genotype ΔKu80ΔPNPΔIMPDH::HXGPRT), wherein the PNP and IMPDH are simultaneously knocked out. This strain exhibited a significant reduction in parasite growth rate.

RHΔKu80ΔPNPΔUP::HX (Genotype ΔKu80ΔPNPΔUP::HXGPRT), wherein the PNP and UP genes were simultaneously knocked out. While this strain did not exhibit an apparent phenotype, PNP is a drug target in human disease such as cancer. As such, this strain could find application in drug and vaccine development.

RHΔKu80ΔNT2::HX (Genotype ΔKu80ΔNT2::HXGPRT) and RHΔKu80ΔNT2 (Genotype ΔKu80ΔNT2), wherein the gene NT2 encoding a nucleobase/nucleoside transporter (VIII 3.242-3.234 Mb) was knocked out. These strains did not exhibit a clear phenotype.

RHΔKu80ΔOPRTΔNT2::HX (Genotype ΔKu80ΔOPRTΔNT2::HXGPRT), wherein the genes encoding NT2 and OPRT were knocked out. This strain exhibited a severe pyrimidine auxotroph and would be useful as a vaccine, alone or in combination with other gene knockouts, as well as in drug development.

RHΔKu80ΔNT3::HX (Genotype ΔKu80ΔNT3::HXGPRT) and RHΔKu80ΔNT3 (Genotype ΔKu80ΔNT3), wherein the gene NT3 encoding another nucleobase/nucleoside transporter (locus i.d. 44.m02769) was knocked out. These strains also exhibited no clear phenotype.

RHΔKu80ΔOPRTΔNT3::HX (Genotype ΔKu80ΔOPRTΔNT2::HXGPRT), wherein the genes encoding NT3 and OPRT were knocked out. This strain exhibited a severe pyrimidine auxotroph and would be useful as a vaccine, alone or in combination with other gene knockouts, as well as in drug development.

RHΔKu80ΔDHO::HX (Genotype ΔKu80ΔDHO::HX) and RHΔKu80ΔDHO (Genotype ΔKu80ΔDHO), wherein the gene encoding dihydroorotase (locus i.d. 83.m00001) was knocked out. These strains exhibited an extremely severe pyrimidine auxotroph.

RHΔKu80ΔOPRTΔDHO::HX (Genotype ΔKu80ΔOPRTΔDHO::HXGPRT) and RHΔKu80ΔOPRTΔDHO (Genotype ΔKU80ΔOPRTΔDHO), wherein the genes encoding DHO and OPRT were knocked out. These strains exhibited a severe pyrimidine auxotroph and would be useful in vaccines, alone or in combination with other gene knockouts, as well as in drug development.

RHΔKu80ΔATC::HX (Genotype ΔKu80ΔATC::HX) and RHΔKu80ΔATC (Genotype ΔKu80ΔATC), wherein the gene encoding aspartate carbamoyltransferase (ACT, a.k.a. aspartate transcarbamoylase, locus i.d. 80.m00005) was knocked out. These strains exhibited an extremely severe pyrimidine auxotroph.

RHΔKu80ΔCPSII(ct)::HX (Genotype ΔKu80ΔCPSII(ct)::HX), wherein the C-terminal 150 amino acid residues of carbamoyl phosphate synthetase II were deleted. Like the cps1-1 knockout strain, this strain was an extremely severe pyrimidine auxotroph. In addition this strain completely stable and nonreverting.

It is contemplated that the above referenced stains, e.g., RHΔKu80ΔATC::HX, RHΔKu80ΔCPSII(ct)::HX, RHΔKu80ΔOMPDC::HX, RHΔKu80ΔOMPDC, RHΔKu80ΔOPRT::HX, RHΔKu80ΔOPRT, RHΔKu80ΔOMPDCΔUP::HX, RHΔKu80ΔUP::HX, RHΔKu80ΔUP, RHΔKu80ΔOPRTΔOMPDC::HX and RHΔKu80ΔOPRTΔUP::HX, alone or in combination with other knockouts are useful for drug discovery in apicomplexa and humans. For example, a malaria, cryptosporidium or human gene activity corresponding to any knockout in the pyrimidine pathways can be used to complement the *toxoplasma* knockout mutant and subsequently applied as a drug screening tool to identify new inhibitors of cell growth.

It is further contemplated that since PNP, IMPDH and nucleobase/nucleoside transporter proteins are important in purine pathways (as well as transport of pyrimidines), strains RHΔKu80ΔIMPDH::HX, RHΔKu80ΔPNP::HX, RHΔKu80ΔPNPΔIMPDH::HX, RHΔKu80ΔNT2::HX and RHΔKu80ΔNT3::HX can be complemented with human homologs of said proteins for use in drug discovery assays for inhibitors of the human enzyme.

EXAMPLE 6

*T. gondii* as a Delivery Vector for Exogenous Antigens

By way of illustration, gene specific primers are generated to amplify the coding sequence for *P. berghei* merozoite surface protein-1 (MSP-1), the sequence of which is known in the art under GENBANK Accession No. XP_678505. The amplified product fused to the SAG1 promoter (Striepen, et al. (1998) supra) and cloned into a construct which harbors the DHFR-TK-TS marker sequences. The resulting construct is introduced into an attenuated mutant *T. gondii* with a KU80 knockout using established methods and an attenuated mutant which expresses MSP-1 is identified based on expression of MSP-1. A suitable murine *Plasmodium* model is used to demonstrate protective immune responses of the *T. gondii*-based vaccine to *P. berghei* infection. Immune response to *Plasmodium* parasites is associated with reduction in patient infection intensity. With this invention, the potency of immune response against MSP-1 and other malarial antigens is expected.

Previous work has demonstrated the feasibility of using live vectors for immunization against malaria. Immunization of mice with *Salmonella* expressing CSP and MSP-1 protected against *P. berghei*, and induced immune responses against *P. falciparum* MSP-1 (Sadoff (1988) *Science* 240: 336-8; Toebe (1997) *Am. J. Trop. Med. Hyg.* 56:192-9; Wu (2000) *Biotechnol.* 83:125-35). The anti-MSP-1 immune response did not require secretion of antigen from the bacterium or surface display. These data indicate that use of *T. gondii* as a platform to deliver *P. berghei* antigens in vivo is highly likely to protect mice and other mammals against malaria. For use in humans, vaccines that work in the *P. berghei* mouse model can be reconstructed with homologous *P. falciparum* antigens. Safety and immunogenicity testing in mice and efficacy testing against infection in nonhuman primates can then lead to human trials.

Other antigens and animal models are well-known in the art and can be employed in accordance with the present invention. For example, the *B. anthracis* protective antigen can be expressed by the *T. gondii*-based vector platform with protection against anthrax infection determined using either the well-established mouse or guinea pig model (Peterson et al. (2006) *Infect. Immun.* 74:1016-24).

In addition, to facilitate efficacy, gene knockouts in one or more of the GRA genes and/or ROP genes are contemplated. Single gene knockout strains include:: RHΔKu80ΔGRA2::HX (Genotype ΔKu80ΔGRA2::HXGPRT), wherein the gene encoding GRA2 (Locus i.d. 42.m00015) is disrupted; RHΔKu80ΔGRA3::HX (Genotype ΔKu80ΔGRA3::HXGPRT), wherein the gene encoding GRA3 (Locus i.d. 42.m00013) is disrupted; RHΔKu80ΔGRA4::HX (Genotype ΔKu80ΔGRA4::HXGPRT), wherein the gene encoding GRA4 (Locus i.d. 583.m11414) is disrupted; RHΔKu80ΔGRA5::HX (Genotype ΔKu80ΔGRA5::HXGPRT), wherein the gene encoding GRA5 (Locus i.d. 76.m00004) is disrupted; RHΔKu80ΔGRA6::HX (Genotype ΔKu80ΔGRA6::HXGPRT), wherein the gene encoding GRA6 (Locus i.d. 63.m00002) is disrupted; RHΔKu80ΔGRA7::HX (Genotype ΔKu80ΔGRA7::HXGPRT), wherein the gene encoding GRA7 (Locus i.d. 20.m00005) is disrupted; RHΔKu80ΔGRA8::HX (Genotype ΔKu80ΔGRA8::HXGPRT), wherein the gene encoding GRA8 (Locus i.d. 52.m00002) is disrupted; RHΔKu80ΔGRA9::HX (Genotype ΔKu80ΔGRA9::HXGPRT), wherein the gene encoding GRA9 (Locus i.d. 50.m00019) is disrupted; RHΔKu80ΔROP16::HX (Genotype ΔKu80ΔROP16::HXGPRT), wherein the gene encoding ROP16 (Locus i.d. 55.m08219) is disrupted; and RHΔKu80ΔROP18::HX (Genotype ΔKu80ΔROP18::HXGPRT), wherein the gene encoding ROP18 (Locus i.d. 20.m03896) is disrupted. In addition to the single gene knockouts indicated, disruption of two or more GRA and/or ROP genes is also embraced by this invention.

What is claimed is:

1. An isolated mutant *Toxoplasma gondii* that exhibits enhanced homologous recombination resulting from knock-out mutation of the locus encoding KU80 protein of SEQ ID NO:2.

2. The mutant of claim 1, wherein the mutation comprises replacing the coding region or promoter of the locus with a nucleic acid molecule encoding a selectable marker.

3. The mutant of claim 2, wherein the selectable marker is hypoxanthine-xanthine-guanine phosphoribosyltransferase, thymidine kinase, hygromycin resistance, cytosine deaminase, dihydrofolate reductase, bleomycin, chloramphenicol acetyl transferase, or a combination thereof.

4. The mutant of claim 1, wherein said mutant is attenuated.

5. The mutant of claim 4, wherein the mutant is attenuated by pyrimidine auxotrophy.

6. The mutant of claim 5, wherein pyrimidine auxotrophy comprises mutation of one or more proteins involved in pyrimidine synthesis or pyrimidine salvage.

7. The mutant of claim 6, wherein the proteins are selected from carbamoyl phosphate synthetase II, aspartate transcarbamylase, dihydroorotase, dihydroorotase dehydrogenase, orotate phosphoribosyltransferase, orotidine 5'-monophosphate decarboxylase, uridine phosphorylase, uracil phosphoribosyltransferase, a nucleobase/nucleoside transporter of pyrimidine bases or nucleosides, or combinations thereof.

8. The mutant of claim 1, wherein the mutant further comprises in its genome one or more nucleic acid molecules encoding exogenous proteins.

9. The mutant of claim 8, wherein the nucleic acid molecule replaces the coding region or promoter of the locus encoding KU80 protein of SEQ ID NO:2.

10. The mutant of claim 8, wherein the exogenous protein is a therapeutic antibody, protein, enzyme or peptide.

11. The mutant of claim 8, wherein the exogenous protein is a non-*Toxoplasma gondii* antigen.

12. The mutant of claim 11, wherein the antigen is a bacterial, viral, fungal, parasitic or tumor antigen.

13. The mutant of claim 8, wherein the exogenous protein produces a non-*Toxoplasma gondii* antigen.

14. The mutant of claim 13, wherein the antigen is a lipid or polysaccharide.

15. The mutant of claim 8, wherein the exogenous protein is a human therapeutic target protein or enzyme.

* * * * *

SEQUENCE LISTING

<160> NUMBER OF SEQ ID NOS: 86

<210> SEQ ID NO 1
<211> LENGTH: 20001
<212> TYPE: DNA
<213> ORGANISM: Toxoplasma gondii

<400> SEQUENCE: 1

| | | | | | |
|---|---|---|---|---|---|
| ggactcccca | tccacgctgc | tatgaacaaa | acgtagcttt | tcaaaaagct | ttaagaaact | 60 |
| ccggttcttc | gtgttcggtc | tctctgaaaa | acggggagcta | aacatgagga | aacaaggtcg | 120 |
| cgtctcgccg | tcacgctcca | cagacttact | tggactcttc | tggagagagt | ttgttttccc | 180 |
| gagtcgaggt | cgttgtggaa | atgaggcaga | aggcctatgc | atgcattgac | ccagatagag | 240 |
| cattcgatag | ctcgaaatcg | cttttcagac | gaacgtgtga | aggccatgag | gccgagacgg | 300 |
| aagtgtgcgt | ttactcgggg | gacgagagag | gctctacgtc | atctgcgttt | tttcgtgccg | 360 |
| tttgtttct | ctctggaagc | actgcagggg | ataatgtggg | gtcgctgtct | gcgctcaggt | 420 |
| accctagctg | cattctctgg | ctcgactgca | gggacgaagc | agtccatcga | cgcagactag | 480 |
| aaaaacgagt | cgagcaaatg | cttcaagtgg | gtggatctcg | cgttctcatt | ccacctatct | 540 |
| ttacgcgcta | tttcggtctc | ataggcttct | tttcttgatc | gcttccagct | cttcgcctga | 600 |
| gtgtccgctt | ttgcaagttc | ggcttctctc | cttgtggcca | cggggtcgct | cccgtggggt | 660 |
| ggcgttcctc | ccgtgctacg | gccaccacaa | gcttggctcg | actgcttctt | ccttctcctg | 720 |
| tttgctttca | agatctaaac | ccgcagtagt | cctcatttcc | acacaagaca | cttgcacgca | 780 |
| tctgtgtgta | ggcagaccgc | ccagaaaagg | tgtatcttgt | agacgcaggc | gtcctgtttg | 840 |
| cttccttcct | gtcgccgttc | tgccccgcct | tcgcgccccg | tagtgctcac | agcttcggca | 900 |
| ctgtgtgacc | tccttgacac | gcgtcatgcg | ctggcagctt | tctctgaaga | actcttgagt | 960 |
| tcctcgtcaa | ccgccgcctc | tctcgtctgt | gtcctgtgca | cacatgccac | gcaaacaggc | 1020 |
| tgggctcctc | caggagtgcg | agtggctgct | cgacaccta | ggcctctacg | agggccgcgg | 1080 |
| agaaggagct | cgtgtttcag | actctacggc | tcccgaagaa | ggcgcgaagg | agacaggaag | 1140 |
| agaaccggag | aaaaaacggg | tgaagacgac | ggctgagcgc | ggtgtctcct | ccgacggaaa | 1200 |
| cgcgacggct | gcgaccgttc | caggcgacgc | caagggagac | accacgcttg | tggagacaag | 1260 |
| cggagacagt | gcgtgcgagg | acagggcctc | tcgaaaagca | gagcctgccg | ctggaggcga | 1320 |
| gacgagattg | cctggagtgc | ttcagagtat | aggtgagacg | aaaggagaga | gtgagagtga | 1380 |
| atggattgag | gagtgaatag | atgcacactc | ggatgctgtg | tctgacgagt | ccagggaggt | 1440 |
| gggcgacgga | ctctcagaaa | caccaggggt | tttctctgtc | tctcgctgga | gtccaggccg | 1500 |
| cggcactgca | gtctctcggt | gtgtttgaaa | cgaaacgagg | gagaaaagga | agcacgaaac | 1560 |
| gaagtgggga | aagcgttgac | ggagaatgca | tgaacagact | aaggagttgg | tggggacccc | 1620 |
| cgagttgggc | agctgaggag | aaagagatgc | acgcacagtc | gcgtcatggt | gtttcctcgc | 1680 |
| agacgtctgt | ccttctctcc | aggctacaaa | gaattcatcc | ccttcctgct | tcaccaagda | 1740 |
| caaaaacaac | gtcaacagac | accgaccgct | tccacttccg | cttctactgg | gtcttcgtct | 1800 |
| tgctcttctt | catcgacgct | ctcggatagt | tcttcctgtc | gctttggatg | tcccgcgggc | 1860 |
| actctgtgtc | cgccaacact | ggcctctgcg | gcagcttgcc | tggtgacgcg | gtcgtgccag | 1920 |
| tacgcgaaga | agcagcgccg | ctggattgtc | aacaaatttc | ttcttcgcca | gcagcacttg | 1980 |
| cctctctatc | tcctcgacac | cagccacggt | gagttcctac | cccagcgggg | cggcaagtgt | 2040 |

```
tgcgactcgc gtctcgacgt cctctgcagt ttctgcccgt gctcgcactt acacctttca   2100
acggcagcag tcgaaaaact cgtcatcgcg aatgctgatg gtgtgaatcg ttttgtgctc   2160
ttccccttgt tgtggaattg cactgccgag atacacagtg atactccaca agcgtcaaac   2220
aaggttgtac aagaccctcg tttctctgtg cgtatcgacc ttgcttctct cattgctttc   2280
ctccggcaat caaggcagcg gtcgcactgt ggcgatctgc ggcagaacat ttctttctcc   2340
gaaagaaacg aagttctttt ttcgaacttt agaagtcatg atcaatggtg gaaaaggaga   2400
caggcaacag gaggcgcata ctgtgcctgg cgatcgttgc gaatctcttt tccttaccgt   2460
gtcttgcatg caaagaacag tggggcggtg gcactttgtg gccgacatgt ggacgaaaca   2520
cctacattta ttcgcgtcgt ttgttgcccc aaagagatct gtgatgacgt cacggatttg   2580
cttgtttatc tcagctgaga acgaacaagc gtggcacgac gaaacgcacg agcctgcgat   2640
tcgaattgtc cacggtaggc gcgcctttct caaacacag gttcctcttt cgcgtttcgt    2700
ttttcatggc cttcaccttc gtttccgccc tcaattttc gccactccct tggccacgcc    2760
taactatctt tctgtctatc tatatctata tgcatatata atccagtttc atgggatttc   2820
gtgttattct gttggcaaca atgtcttga gtttaccctt ttgtttcttg cttccaagaa    2880
ataggaacac tggtagaata tttaatccag cacgtgtatc tttcagtttg gtctcggaag   2940
gccgtattgt ttcctgtttc tctttcttgt ggcgtcctgt gtctctgtcg ctctcgattt   3000
ttccgcatcc cgtggcgcat cgttttctc gcagtgctct ctgtgactcc cggctcgcca    3060
tgtttgtttt ttttatcaca tatgcccatt tccttttctt gaaaattcga gaagtccagc   3120
ttcgacacgg ggcacagcgg tcggggacgc tcatgcgtgg gtcgttcaa gaagcccaaa    3180
agagcgacga gctttagaga gtcatgcctc ccctctcctg cagcgtctag ccgtggaagt   3240
aacatgcctc ttgttcgaat gaagtagccg cttttttaaac ttccttcgta cggcagaacc   3300
agaaggaaaa cgttgagatt gagaactgaa cgcaaaattc ttcggatgtt agtgcgcctt   3360
ccccttttgct gtatgcggag tatccgatct tctacgagaa agtagaagaa atcaatgaat   3420
ctgagagtgg cgaaggctta ggcagacgca gcgaaccttc agttttttca gtgctcttct   3480
ctgcttcttc ctcagagttc ctcaacaaca agcctttcac ggaggaccat cctcatgctg   3540
cagctgcaca cctgtctggt gagtctttcg ccgccttcac tccaaatctc agagagatcc   3600
cgatgtccca ggaagaactg ctcccagctt tttcggcgtt tcttctcagt ttttttccact  3660
ttcggtaaat gccagaggct gttgctcgta tagtttatga atgcgtagaa ttctacaggt   3720
gaagtgatca gtgtcgatgg gaggtggagg tacacgtcca tctaggctcc cgccggtatt   3780
ccgaagagtg caagcgcggt tcttgtgact ctggtgctct tccccttttt tttgattgcc   3840
tcggttcgca gcctgtgcat gcatgcaaaa cgcatcctct tttcgttctt gacattgcac   3900
ccgtttccga tacactaggg ctagacgcg ctcaagcgtc tcgctgttgt cttcgttccg     3960
atgtgagaga aaagaagtca tgttaaattc aaatttacta aggaaaagca gggtattagt   4020
agtgcttttc gagcatcaca gcatgtctaa tagtgtgcat gctttgccac gttttcagaa   4080
gcagaaaaag ctaaacgcga gagactcaag gctctgtctg ggcaagcttc aggtgtcgcg   4140
tccacaatag gaaaagaccc gtgggtcgac ggcggtctca accggtgagg aattcacttt   4200
ctttcgtctt cataaagatg cgaattcaat tgtgacttcg accacgaatc acctatatat   4260
tcatgcgttt atatattcag ctccattcac tcgtctggtt attttctgcat attttcagtg   4320
tttgtttggt gaggtcactt ccgtgtgtgc attccgccac ttcgtctgca cgtacgctac   4380
```

```
atctggacgc atgtaactgt gcgcctatct acttcccata taaatatata tatatatata    4440
tatatatata ttcataggta tggatactga gtttgacgga gatatacaac atgacccagg    4500
atcctgaatg tacttccatg gtgagatgca gacacccagc tttgtcactg cgagtctgcc    4560
gctgtgttct cttgccggaa aaacgcctgt cgtcgacctt cgtttctcta ttctcctttc    4620
acggtcgcat gcagaccgcg aacgtgcacc ctgtgcaatc gaacatgcat tggcgagaca    4680
gactggctgg accacgtgaa gtcgaaagct caccgggctc gcacgaagaa ggaaaatgca    4740
gggaagaagg acttggacaa caccgaggag caggagacaa aggcgataga agtttccatt    4800
tcagccaacg aaaaatcaga gtgctaaggg gttttaggga cgcgtaccaa cgagagaaat    4860
acagggaaga agaacttta aaacactcgc aagagacaat ggagagagat gcgtccttgt     4920
caaagtccga agaaacagaa tgctaatata ctgtgcgaca agggcaaagc aagttctccc    4980
ttccgtccta aacagtggcg gcgctgagac ctgctgtttt gcgttaccga gtcacttaac    5040
tgttgcgccg gttttttaa taggtttctg tgagaaatct ttacaatgcg ttattagcga     5100
atagggctac ttagagggct aggtacctat acggctagta ctggatcttt gcgcccgacc    5160
aacagacctg ggacctcgtg caggaggtaa aactacattc ccatggtacc tatgcatgta    5220
ttgagaattg atatctcaaa tcgataaaag aagatctgat agtacagaaa gaacaattct    5280
cggtgaagtt gaaagtcccc aatcgaaaac tgattacaca cagacattgt ggtacagacc    5340
aacagtatat ggtgtagctg cgagttttac gttcttcagg cagaatcgta gatcggccac    5400
tgaaaacgct ttgactttag actcagttgc ttttgactga aattggcatc tcaccattta    5460
aaacgaccag ttttccttcg ccgtaattcc atagttgccc cgacagagtg cttgccgtat    5520
tgtaaaaaaa tagtcagatg gcgacatcag aggaggatct gcttctggtt cacgaacgag    5580
tagataggtc taagcggaaa aatcagcgga agaacgatct tttgaatcag aaagatagaa    5640
cctcttatgt gaaagtaggg gcgtcaagta ttagcatatg agctgtgaag acggtagacc    5700
gcatgtcatg tacgaggttg ttcagtgttc gttgcgaaaa gctgttacaa aaagtgtctg    5760
atggagcttc gagtcgtctg ttctggtgtg gaatcttaag ttgtctctcg actttcgttc    5820
cacaagctac tcctcatggt agctacagac aacggcagga cagcgtacaa gagaaactga    5880
ccgtgaaagt gccgtctttt tttcggggaa tcgcttttgc aaacaggacc ggcgctgagt    5940
atccgaatgc cagtgataag gttatgaatt tcctgctagt ggacaatccc acgactgtgc    6000
attcacgact tcgagcagaa gttcacattc tcactgtagc tgacggtgga aaagaccgta    6060
cacatctgca cgcacacgct gacggatcgt ttttgttcc agttgcatcg tgcagtctct     6120
gtgcagcttt gtctgttcaa ctgcgcgttt ccttgccaaa cttgtgcaaa cgtcgccgtg    6180
cgcgccttcc gtgtatgctt tgaagctttg gtcattaaca gtgttggcac cttcgaattg    6240
cggaactgaa agtcctcgga attcgtgaga acggtgaact acggcagcag cgaaattctg    6300
gaacactcaa agcggcgaa gagcaagaga cacaaaagtg tggcaaacgc tgggcttct     6360
gcggccagaa taacgccagg gacacaaatg gtgctggtgt ggtagaatag cactgctagc    6420
aatcgacgtc atagggctac ccaactcacc agccattcag tgctacatct ggagacacgc    6480
attgttgacg agtgatgtca ccaacctgcc aatgaaattt aaattaatac aaaagaccac    6540
gttcttcatg atagctgtac accacgagtt ggacgactga tttagatctt gaaggaaact    6600
tgccgagcca cactatcgag cgggacaaag acagtcgatg tcgaagaact tgagtgacgt    6660
atcatgatat tcactttaga gtcgttcgct tcctaatttt gatcaggcca gccatatgct    6720
attcgatact cgaatctccg agaacacttg tacactaata agaaaggacg tcattacgaa    6780
```

```
cacaccacca gttctggata aagagatttc tcgacgtcac ggcagcttcc ttgttctatg    6840
aatataaaat gtagaaaacg gcaatcgaca cacacccgat accttttggg tttctttgca    6900
gagaaaacga gaccaatgcc gtcgtgccac cgtacgtacg aaaagaattt ccttgtctgt    6960
ccttgctatt tcctaaaact ccccaggaag actctatgtc aacaaccagc taatcgatca    7020
gcagttgcta gacttgtgcg acaaacaatg attctgttga attggtttct ccttacgatc    7080
agttcatatg ctgtacggac gtaagtacaa atagagttcc tctaaatcgc ctgggaaact    7140
cttgaatata ccaacagagg tccacgaacg actcaaacgt ctccctagta aagcacggaa    7200
agttaccatg gagctggttg aaagtatcct ttcaactacg acctgcgaat aggaaaccct    7260
tttaaaaatt tgggaaggat tcacttgggg acctcaacca cttgaagact caaaataaaa    7320
gagaatagtt cttttagcag aggcgaacga atagggatgg ggaactttcg acgtgccgtt    7380
taaatatagt tctctgccca acctctgctg tgtgaccaac tgttttttt cgacgatctt     7440 accactcctt gaagaaactg gaaatgcttt catatttgca attctttgag gagcacagat    7500
ggacgaaact ggaagtcgaa agggaacccc tgagaaagga cgtccggccc tctattacac    7560
gcggcgagtc caacgagtgg aaacgaagct tctccatttg gcttacgtta actcgaattc    7620
cccccgtcaa atggaaaaca tggaccttca gacctaggaa acagagccgt aaagaaggaa    7680
cttaaaacag tatgtacgga acttatcctg agacgagact gcttgcatgc aactgcttcg    7740
actgcacagg tcaactagcg tttctctgac ggctaaaaga gctttctgtc taaactggaa    7800
acagttgtcc ttttccaccg cttaagacgt cttttttcatc atatttccgt ttcagttgca   7860
cttcactcag tcaaagatta aatcgctact tgtgtgtctt cactgcccgt ccccggttcg    7920
cctcagcaca cacacatgac gtacatcgcc gacaacaaac gggtacacct ttctcatatt    7980
cccggattct ctgtcgaaaa aatggatagc tccattgttt ctgatgggaa ctattccgac    8040
attacgggac aggaaaaccg gcggacgcct cgcagtgcgt gtttctgttc ctgttcctac    8100
tagagaaact gtagtatacc tggggtattg aaagtgacgc cagtcatgaa aaccaaacag    8160
ccactctatt aatgaattcg ggacctatag ttcctggggt cataagtcct cgcttggatc    8220
tccacgtgag cgagatccga ctcttcatgt ggcgtttctc tgaaactttt tctgaaggcc    8280
aaactaaatc gtcgttatgg agtcgggtcg agatggcccg acggttcgat cctgagttcc    8340
gttacatttt tgaaatcctg aacgagacca caaattgagc aacttgacag gcgctctaga    8400
cagggctaaa gctctttttt tatgaatgca tgtgctgctc ggagttcagt tttcccccaa    8460
agattcgcca acttctgtcc tgtgcatttt cttctcccca aaccaacgga cttttctaact   8520 tgtgtcgccg ttttttctct tcttgatctt gagcctctgc acctcttgta actcaaccca    8580
cagtgagtat cgcccacgtc tatgatgtct ctgttcgagt tgcggtatac gcagttctgg    8640
gtcgcggatt acttgcacac cgactgtttc tacttgcaag gcggaagttc ccaaaatact    8700
gcatggtcta gccgacttct ctttcttatt ctcctcgcaa aatggcgctt cctgggcaaa    8760
gcttcaagcg agtgattgtc ctgctcttgg actgcggcgc tacaatgcag cagacgcttc    8820
gcggcgactt ttcagatgcg ctggtagcgc agactgaggc gctctcttcc tcattcgcgt    8880
cttctggagg tgcctcttcg ccgtctcctc tttccaaaaa ggccgattca acgccgtccc    8940
aagtgcctct ttccccagac tctgttccat caatatcggc agcagacaga agtgcggatc    9000
tctcgagttt ccacgccatg aagcgcgcag ctcgagcgta cgtacagcgc ctcgctgcga    9060
cgtccgcgaa agtcgacgtc ggcgtcgtgt gctttggcag ctgcagaacg gacaatccac    9120
```

```
tcgcgcctgt cgagggcgac atccagccgg gagacacggg agacgcagag aagggtaca    9180
aacatgtcga ggtttctctg cgtcccgaaa gcgcctcctg gaagctcgtg caggagttag   9240
agaaagtcaa gaattcggcg aatcggagtg acgccattga cggacttgtc gtcgccgtcg   9300
acatggttga gaaaacgtat ggcccaaagc tgtcgcaggt gagaacagca cacggactct   9360
gtttcctgac aagcagaact tgcacagtgt gaacaacaga caacaacagg cgccgcgggg   9420
ttaaagctgg ccgggataga agatcggacc gatacttcgt ggatgactgt gaatgttaat   9480
tcgcgtgaca agaggactcg taactgagtc atttatctat cacgaagatg cgtggttgat   9540
cttatttgct tgcttaccac ttacagcggc ctgcattttg agggtctttg cttaccagat   9600
ttaagttccg ttgtgccttt ttccacggcc aatgataagc gatccagaac tggggaactc   9660
aaggggagca aagagttgac aacagagacc ggacatgaac tgcatgaaaa atgcttctct   9720
tttctttcca gcttcccctc caaactcgct gtcccacttc tgtcttgtct ggatcctcgt   9780
tggagtcagg ggcgcgtcgg acgagtggag agacacctga cttcggcttg ccagcttctt   9840
tttctcttgg ctgtctcatg tgcttgttcg cctcttctgc cagacacaga cactcctcaa   9900
ctgcaccctg ttgtttccat tgctttgttt tctctaccgt ccaggaccct ctgttgtggt   9960
cgtcgatctc tccacttggc gctatccgtt tgctgttttg tatcgttttc aatgacttaa   10020
gttttgatt tgcacacact gtaaaagaaa cgaatccaa taatcagaca ctttctccgt     10080
tctatgttgt taaaagctat gctgaacgtt tttacgaaaa aactgttttc aaatcattaa   10140
aaaaccgtgt tccatttcta acaattcttg tcttttctct cttctactgc gacctccaga   10200
ataatgtctc cttcctcgtt ttctccgact gccagtcaag cccagcaacc cctgaggata   10260
tcccagctgt acgggaccgt cttgaggtgc tcggtattcg agtccacttc atcattgttg   10320
gtaaggcaac tcagagcgac ttcgtttctg agctgaaaga acagactgcc gcggacgact   10380
ctccagaaca aagacacgga gcacgcatac acctcaagtt cacacagacg gcttccactc   10440
ctagttgcag atgcctcaaa atacagtggt ggatctcttc agaacacgtt tcatagcatg   10500
tatatatata tatatatatg cacactaaga tatttatgaa gatatgcata tgtgggtatc   10560
tgcatgcatg caccacttt atatatatat atatatatat ggatatacct attatacagg    10620
cccagcaaag ctggggaaat gatctttagg taatagttga gacactttaa gcggcgtttc   10680
gtcgggcaa ttgagtcagc cagcttgtct gctcctgtct tctttcctct cctctcccctt   10740
cttcgttgtc tcttttctgt ctctatcctc gctgctgcgt ttgtcgtgca ttttccttgg   10800
tcgtctgcgg ggtgcatgtg acacaaagcg cattacggat tgcctgtctc ctctccattc   10860
gttgtgcagc cttgtgtctc ctttcgttcc ctctgcctct gttcctcccg ctgtttgcct   10920
gcctcatctc ccctctctaa tctctgtttc tgcctcgtgc gcagatggct ctgttccaac   10980
gcatccgggg atctggcgtc caggtgatcc gagcgcgcgt ttgaatcagc attttgtctc   11040
gcctcttcgt cctgcgttgg cgtccctctc tcttgtggcc tcgacgctga ttcctctccg   11100
gagtttcttg gcttccccgt ttatgaccgc gttctatcct ccaccgaagc ggttgtcgac   11160
gaagtgtcgg gtgaatctcg aagtctcgaa ggccttcctg atccccgtgt atgtcttcgt   11220
aaggactagg aaagagccag taccgactct tcgcaagcgc gtcttcgtgg gggtctctcg   11280
gcctgcaaca cgaagaagaa cggactctgt tccccgagag gacacgccag cgacgctttt   11340
cggagctgag aaaacgcgaa acgaccaagg ggaacacgat gaggactgga gggatctgaa   11400
agtcgaaaga ttttacttca gagcgaacga cccggaaagg acgccggtga agttaggcga   11460
accggacaca cgacagcggg atggaaccag catcttcggg aggcctgacg gatcctccga   11520
```

```
ggacgagcgg gcgcccggag ccggcggcga cgctggggtg cacatacaac gtctgtacgc   11580
gtaccgatac ggcaaacagc tggtcgccgt ctccggcgtt gagcagcagg cgttcaagca   11640
gcaaacgacg gcaggcctgg tcgtcttggg cgtgacgagg cgcgatagta ttcagaggtg   11700
gtgagtgttc gtgagacgcg aagcaagaaa agagttgaga atcgatctcg aaaaacgcca   11760
ctctctggag gcgacttctg cgtcctgcga ggccttcaat agcctgaaaa gcagagaatg   11820
agagagaaca cgttgtcgag aaaacgcaga ggaatcgaac ccaggaaata gtgcttcccg   11880
tttctccctg taggttctct ctcttgcgct ttccaccttc ctagacacgg atggcttgca   11940
gataaaacgc caacgtctcc gtgaagacta acacgtacat attcgattca gtttccccct   12000
gaggcgcaca gcattgcttc gtctgctgtt ttctgaaaat cccgttcttc aggtggaatc   12060
taggccctcc agaatacgtc acctgcgcgc tcaacaaccg accgtctctc gtcgccttgc   12120
gctctttagt ccttgcgctg cagcgtcttg actctgttct cctctgctcc ttcgtgtggc   12180 ggggggggcta tccagcgaag cttgtcgcgc ttcttcctca cgttggaggg ggtaacaggg   12240
agaaaagaaa ggcatggcag gcgaccgcct cgttgaagga gagtgacgac gtcaagagag   12300
aagaagaaac aaaccaaaag gaggccggag acgaagacaa gacctacggg cttcatctta   12360
tctacttacc tgtggcagaa gatatgctcg agctccggct gccctcgctc ccgtccgtga   12420
cgccgcgtca actgcgagct gtagagacac tcgttgagag tcttacgctt ccaggaagcc   12480
cccaggtgtc agtgaagtca ggcgagaagg gaggaagagc ttcggagaag gacgaaggcg   12540
atagagaggc cgaaaaaaag ccaattgatg gagagtggga ggaagtggag gcgcagcgca   12600
aagctctcca ggctcccgct tcttctcctg ccgggtggca aacaaatgca ccgctggaga   12660
tcgcggtgga tccttcaact cgagttcact ctccgtcgcc tccgtgttcg tctgccgcct   12720
ttccatcttt cttgccagat tcgatttcca gctttgcgac gaagtcggag agcttgtctc   12780
ttcacaaaat ccacaacccg acgctccagc ggtactacca gcttttggtg tacagacact   12840
acaatccggc gtcgcctccg gtggctcttg gagaggaggg gagcgagacg caggcacaaa   12900
caacttggag ggaggcggag gagagtcacc aacatcgcct gcaccacatg tgggctcgcg   12960
ggtctccagt cgagaggctg ttcacggtgc gaactccagg gtgtctggat tctgagcagc   13020
cggacgcctc cgtcgaacag accaaagagg ccggccagcg ggagacgcag gttgatgccg   13080
ctctgaaggc ggcttttcct caggcaacgt cgctggaagc ccagacggca ggacgacgac   13140
agagggaagt tcagcagaaa ctgttgttcg gagaagtcgt gaggaaacag aaggagctgg   13200
ttgttcgaga tgtgaaagtg tcgggcgagt ggaccgagcc ccatttcgat acacctgggg   13260
aagagccgcg aatgacagcg gaggcgcggc gggaggagac agagaaactc gagcgggcga   13320
ttgaagagga agaacggcag aagaaactcg aggctctgaa ggctctgcat gtacacagcg   13380
tgaacccggt tcgagacttc cagagactac tcgaagtaaa ggaaacggat ttgactgaga   13440
aagcgattca ggaaatgact gagatgatct tcaagtttct gcgggcagcg gggccgccgc   13500
agggagcgct ggagaggcca acgggagctg ggcgaggagg agagacgtcg ggactgcaga   13560
actttcggcg acaacaacac cttggcaagg cactcgtctg cgtagaagct ctgagggagg   13620
gatgccgaag agaactggag ggcgagaaat tcaatgagtt tcttgcggaa gtgaaggcgg   13680
aacagtgtcg ggcggatgct gcggccgacg acagcttccg gaccttttgg aacttgctaa   13740
aatccagaaa aatcggcctc atcacgcacg ccgaggaccc acgcgtcgac ctcgagccgg   13800
cccagtctct gagaatctac gaagacgaat cagtgcaaga gctttcgacc caaactgcga   13860
```

```
tgacggccgc gagacccctta gatccgcatg acgttgatga cttactcgat ctcgtcgagt   13920
agaaaacgaa cgattgcttc agagaaaaat gccgtcaggc ggtctttgac aaaacgggag   13980
tggttgctct tggctaacat ctgcgggcag ttttcgattt tccgtctcca tgtacgtata   14040
tttgcatata aatatgcaga tgtacatgag tcgatatatc tcgctagcta taaatatatc   14100
tccatgtatt tatacatgta tgtgtatgaa acatacatct atgttatcta tatctatgta   14160
cataagtgta tgaggtgttg cgcagatgcg agagggctgg tcggaaagtc ctaaatcttt   14220
tcaaggcgtg cggaactcgt tttgtttgcg ttttctgttt caacaatgtt gagcagtcaa   14280
atattcttac gaggacaggc cggtatggtg attgcaccgc gtgaaatagc ggtgaactaa   14340
aaaaatgggg agatttgctg cccccacgaa gccacgcaca gaaaatgaag ggaagggcaa   14400
aggcttacat gagcacgcgt acacatctgc ctacttcact tctcactttg acgttgatta   14460
gatctcatca cacatgcctt ctagggagtt cgcgataaat gcacgcaacg gttttcacga   14520
tgttatatcg ggtagtgtag tgtgtcacac ctaatactag gttgaattcg gagttacatt   14580
caatgactac ggcccagcac gcagaagcac ggatacgcgg cattgctgca tggatattgt   14640
gtttgttcac tgattgtacg atcggcagat acaggcactt ggggagggggg ccatagatgt   14700 atacgcacgg caaatgccta cacaacatat tgtacacatg agtggtggca aaatttcaag   14760
ggaaccttgc cactggccga atatgaatct tcttgtcgcg gatttagcgg atttgagctg   14820
taccactggg aacataatat cgattgttta actctaagct gacctgcgtt ttcgtttgac   14880
cacgggcggt tcctagcagt agctacgtgt tgcatgggac tgctctgctc agttgatgat   14940
agccaggctg tggagtggtg cagacgcttt ctaatctgcg gcaactgcag agttaaatac   15000
cttgtgaagc tgcatgaaca actgagggggg gaaattgct tttatctgac gggtgatacg   15060
ccactgttaa cgttgagctc tcccccaaga accagttagt gtagcactgc gcagttcacg   15120
cggaccggcc tttcattgct tgtgtgcacc atctttccga aacgagggta agaaacaaat   15180
gtggcaactg ccttttgcct gccttcggta cgaactcgag agtatccatg tttacattca   15240
cagcacactt tactaccggg gtggtaccac ccgtctgcag accctcctct gtccaccgac   15300
ccactggagg gaaaaccaga gcagcggcaa cgcgcctccc tcttctagcc gacatgcagt   15360
ctcccatcac ggtgagacac gggatatttt cagcgactca actgctactg cttgtgacaa   15420
aacgtcagtg cgcagcgggg attcgtcctt gttgtcgtgt ctgcttcgca acgattttg   15480 cagaagcgga agagagcact ctgttgcccg aataccgatg caaagctggc tcatcggcgt   15540
acgtgctttt cctgtgaggg catagagtct gctgggagtg aatgcaaacg tgtttactgg   15600
gagccggcag caccgttttc atgagtgtct tgtaaacatt tctgtctggt tcggtttcct   15660
gagacatgca cacctctcag tcccgagcgt tgacggtttt cctctgtgga cggtgccgct   15720
ccgacgtgca tgcgttcatg tgcctgtgag tcgggtgtac acacaccagt cgatttggtc   15780
aatcgccacc caggcgacac accatttctt ttttccttcg ctgagacatc atgacctcgt   15840
cttcgagtaa cggcattcct tcttttcgag ccactagctg gcatcatcct gcgtcacttt   15900
cgggtgtgcg ctcgccagca acgagcggct ccgtgtctcg tcctgcggtc ggcgcttcgt   15960
ttgtcccagg accgccgctg gtgcccggcc attcctgttc tttgttcacc tacgggtcac   16020
agacgtcagt ttcacggttc cagcccgtgt tccaccaaga tggagtgact gagtcatccg   16080
ccgaccactg ttcctccact ctgtccccgg cgggtgccgc cactatagct gtggcacaga   16140
gcgcgggttc cccagttgtc gctgttgctc tgtccatcc gtatctctac ggaaatgtgt   16200
cggcagaggc tggaacgcct gctgacggcg ggcagggaca gggacaatca ccctccgtct   16260
```

```
tcccggtcgt tatcggccta gaaaacggac aggtctggct ttatgagtgg caacaggctg   16320
cgcaggagcc gtccaaccag ggacccttcg aagggttctc gcacgcggct ccaaagtgtg   16380
tggctcaaca tctgctgtgt cgccaaatgg cgcgcccgtt aaccataagt gtcgcgaggt   16440
ttcggcaggc caccgccgac caagattcca tcgacgagga agcaaaacag gacaacttcg   16500
aagtgtatgt cctgtacagc aacgggatgg ttgtcgtttg aagaaaggc cgccggaacc   16560 ggattgaact ggggtgagtt tttccgtggc atctctggaa ctttggtttt ggaggcagtt   16620
ttttcttctt tcgttttctg gaagaatttc atgcgctctg cttcaccacc cttcctgtgc   16680
aactcaatga gatagccgtt tccgtatctt ctaaattaag taccgagaca cgcatgggtg   16740
tcaacgaggg cgggcatgtt tgtcatccac ccgtctatgt ggcttgaaga aagcccgcgg   16800
cactctcctc aacacgagca ttgagtttcg tcggttcgct gacttgggca attctgcttt   16860
tcacaccttt tgtacacttc tgtttcgtaa tgcatgattg ctagagttta atgctcttc    16920 gttcagcccc gattgcctgg atccagaaac cggtggaaca gggacgctta cacaggaatt   16980
actgtgctcc gggtatccta tatggcctct gtatcttcag accggtggaa ggggcattc    17040 acatgagcgt cgactcggag ggtcgatatg tcgcggtgtc gtcgagcacc aggaagcttg   17100
tagttttcca gcgcaaggaa tctgagtttg gcgacgacac catgactttc accaagtgct   17160
ttgacgaaga agttttccgc aaacagctca actctgcatg cgcgacagga gtcccgcttc   17220
agacagcctg gtaggttgtt gtgcgtgtgt ctcttcggta ccaagaaatc ggggaaactg   17280
aaatacagaa gttgagatga gcaaggatct gtcagatact taaagtcttt aatataatcg   17340
tgccctcaga gtccttgaca aattgtctgt ccgagtccac ggcgtgtctt aagtcgttgc   17400
cgtctctgga ggatccgctg actgccattc gagccacgag ttgctgagga atcaacattc   17460
gggtgaccag tgctcgaatc ccagacctgg ttttcagatt attaacgggt gacatcaaca   17520
ctcacaaacc cccttctcct ttcactgctt ctccttcagg catcccgatg gcacctgtct   17580
gtttctgccc ggagcatctt cggtgcgtgt gttgaaaact gcgactatga ctcttgagca   17640
tctcgagttc gcgtctgctg gcttcgaccc gttgattgtt tttgacaaag ttgcggttgt   17700
cggcctcaac ttccccagcc ctgcaagttc gcaaggagag cgatgctctg tagttcttct   17760
tgcgtctgtg aaaacctcgc tccgcgcgtg gctccttgag gacaagcagc tcctcttctg   17820
cgtcgaagca ggtgcgctac tcgtgccgct gaggcagcac atcgcagtgg ctcggcttat   17880
cttcggcatg cgcacagacg gtgtgcttat ttgtcagaaa cacacgatgt cgaagggctt   17940
taacctagat gcaattgaga cgtctcagaa gaagcggaac tgtcgcgccc gtcggtctcg   18000
gggatgtttg cgttaaatgc gcttgctgtg cttgaggcaa ggcaggtcgc cgtgctgtgc   18060
ttctcttgtc gcgttgcatc gccctctaaa acatatgcat gtcgacatca aactgcgttt   18120
ttcttgtgtt cttgattcgg cgactcagac aaggcttctg cttcgagtgc agacagactc   18180
ttgcagctcg ccgcgtggcc ttcgtggcac ttccagaaaa aagacgaggg ccagaaagcg   18240
ttctcgccat tcatcgaggt cggcctcgct cgagatgacg gagctgtaag catcgtcgga   18300
atccgatccg agacacttgc gaagctaagc gagaagcgcg ggagaaacgc gttcgatgga   18360
gactccgggc ttgagcagat ggaactacag caggaacaca gggacaagca agacgatggc   18420
gacgttgtca tggctgacgc ggagggtcaa caagaagagc aactcgaagg tatgtcctcc   18480
ccagagatga aagagcgctg ttcgacttat ctctcgcctt cccaggatga tcgcgtgcat   18540
tcgcaagtgg aggagaactg caccagctct cacctgaagg caaaagagct gcctgcgtct   18600
```

```
tcaagagaca gaaaggccca gaagggcgaa agattggaga ctgaagagaa gaggactcct    18660
cagggcaacg aagagaagac cagagctgag tttttcggag acagaggcgt gactcccggc    18720
acgcccgaga aaaggcgcca cagcgtcgat ggagagaccg aggcaagcag ccaaagtgcg    18780
agagcggggt cttctctcag gcgccacgaa ggggagaaga agaaagagaa gagacgaaaa    18840
gagaggaaga acgcggccgt ctcaactccg gttcgacgtt ttatcgagat gcaggcggaa    18900
gaagggtctg aggaaggcag cgaccaggac ggagaactgt tcggcgacgg accaggaagc    18960
ggcttggagg acgaagcggg gtcagatcac aggggagaga gagagcgagg aaaacggaag    19020
agagagggat cttcgcgacg tcgagacgag aagaagaaac gacagcgacc agcagcaggt    19080
acgcaaaacc tctcagtttt ttcctcgtgt ggcgggcgcc gaacgcgtta atttggcctt    19140
cggaacacac gcttggcatt tttcagcgat atctctagtt cagggttact gtcgtgaatt    19200
accgaattcc agtactttga gctgtctcaa aagcaggcct tggggcact atgactaacc     19260
tacttgcact caagatagtc gtcagggaac gcagaataga atcgtggat ccagtgaaca     19320
aagacattca aggtcaacgg agcatcatcg gacatttaag agattcactg acacggacgt    19380
ccccgtctct gccacatcca cgcatagtat cctagtctgc gtagacaatg acgcagtcaa    19440
ccctcagtcg atgcgaggca gatgctcgtg aatgagtcgg tgaaggatcg tttcaacttt    19500
gcgaactcta tcagccagcc atccgaaacg cgttgtagcc tctgccggtc gcagtctctt    19560
gtcagaacga gccgttgttt ggtatgcagt gtcatgggag attgcctcgc gaccgcgcat    19620
gcgggcacag cttctgtaat gcagattcta ggatcagcag gcacctacaa gttcggtacc    19680
tgtttgctga gatgaagtgc ccacgttctg ttcggggtcc gattctttca gactcgcagg    19740
aggagggagg agacgacggg tacgcgtctt ctgggtctca gactgactac gccttgtctg    19800
ggtcttcggg cgcagaagac gtttcttctg acgagggga agacaacacc tcggaggagg    19860
aaagcgagaa ccttctcgaa gacgaagaag aaacaagcac ccacgcgttt gtctcaggcg    19920
tctcgttcct ctcgagggac acagacggcg gcgctgctga gggcgacgac aaggaggctc    19980
tcctggagaa catgaggaag c                                              20001
```

<210> SEQ ID NO 2
<211> LENGTH: 998
<212> TYPE: PRT
<213> ORGANISM: Toxoplasma gondii
<400> SEQUENCE: 2

```
Met Ala Leu Pro Gly Gln Ser Phe Lys Arg Val Ile Val Leu Leu Leu
1               5                   10                  15

Asp Cys Gly Ala Thr Met Gln Gln Thr Leu Arg Gly Asp Phe Ser Asp
            20                  25                  30

Ala Leu Val Ala Gln Thr Glu Ala Leu Ser Ser Ser Phe Ala Ser Ser
        35                  40                  45

Gly Gly Ala Ser Ser Pro Ser Pro Leu Ser Lys Lys Ala Asp Ser Thr
    50                  55                  60

Pro Ser Gln Val Pro Leu Ser Pro Asp Ser Val Pro Ser Ile Ser Ala
65                  70                  75                  80

Ala Asp Arg Ser Ala Asp Leu Ser Ser Phe His Ala Met Lys Arg Ala
                85                  90                  95

Ala Arg Ala Tyr Val Gln Arg Leu Ala Ala Thr Ser Ala Lys Val Asp
            100                 105                 110

Val Gly Val Val Cys Phe Gly Ser Cys Arg Thr Asp Asn Pro Leu Ala
        115                 120                 125
```

```
Pro Val Glu Gly Asp Ile Gln Pro Gly Asp Thr Gly Asp Ala Glu Glu
    130                 135                 140

Gly Tyr Lys His Val Glu Val Ser Leu Arg Pro Glu Ser Ala Ser Trp
145                 150                 155                 160

Lys Leu Val Gln Glu Leu Glu Lys Val Lys Asn Ser Ala Asn Arg Ser
                165                 170                 175

Asp Ala Ile Asp Gly Leu Val Val Ala Val Asp Met Val Glu Lys Thr
            180                 185                 190

Tyr Gly Pro Lys Leu Ser Gln Asn Asn Val Ser Phe Leu Val Phe Ser
        195                 200                 205

Asp Cys Gln Ser Ser Pro Ala Thr Pro Glu Asp Ile Pro Ala Val Arg
    210                 215                 220

Asp Arg Leu Glu Val Leu Gly Ile Arg Val His Phe Ile Ile Val Asp
225                 230                 235                 240

Gly Ser Val Pro Thr His Pro Gly Ile Trp Arg Pro Gly Asp Ala Phe
                245                 250                 255

Gly Ala Glu Lys Thr Arg Asn Asp Gln Gly Glu His Asp Glu Asp Trp
            260                 265                 270

Arg Asp Leu Lys Val Glu Arg Phe Tyr Phe Arg Ala Asn Asp Pro Glu
        275                 280                 285

Arg Thr Pro Val Lys Leu Gly Glu Pro Asp Thr Arg Gln Arg Asp Gly
    290                 295                 300

Thr Ser Ile Phe Gly Arg Pro Asp Gly Ser Ser Glu Asp Glu Arg Ala
305                 310                 315                 320

Pro Gly Ala Gly Gly Asp Ala Gly Val His Ile Gln Arg Leu Tyr Ala
                325                 330                 335

Tyr Arg Tyr Gly Lys Gln Leu Val Ala Val Ser Gly Val Glu Gln Gln
            340                 345                 350

Ala Phe Lys Gln Gln Thr Thr Ala Gly Leu Val Val Leu Gly Val Thr
        355                 360                 365

Arg Arg Asp Ser Ile Gln Arg Trp Trp Asn Leu Gly Pro Pro Glu Tyr
    370                 375                 380

Val Thr Cys Ala Leu Asn Asn Arg Pro Ser Leu Val Ala Leu Arg Ser
385                 390                 395                 400

Leu Val Leu Ala Leu Gln Arg Leu Asp Ser Val Leu Leu Cys Ser Phe
                405                 410                 415

Val Trp Arg Gly Gly Tyr Pro Ala Lys Leu Val Ala Leu Leu Pro His
            420                 425                 430

Val Gly Gly Gly Asn Arg Glu Lys Arg Lys Ala Trp Gln Ala Thr Ala
        435                 440                 445

Ser Leu Lys Glu Ser Asp Asp Val Lys Arg Glu Glu Thr Asn Gln
    450                 455                 460

Lys Glu Ala Gly Asp Glu Asp Lys Thr Tyr Gly Leu His Leu Ile Tyr
465                 470                 475                 480

Leu Pro Val Ala Glu Asp Met Leu Glu Leu Arg Leu Pro Ser Leu Pro
                485                 490                 495

Ser Val Thr Pro Arg Gln Leu Arg Ala Val Glu Thr Leu Val Glu Ser
            500                 505                 510

Leu Thr Leu Pro Gly Ser Pro Gln Val Ser Val Lys Ser Gly Glu Lys
        515                 520                 525

Gly Gly Arg Ala Ser Glu Lys Asp Glu Gly Asp Arg Glu Ala Glu Lys
    530                 535                 540
```

-continued

```
Lys Pro Ile Asp Gly Glu Trp Glu Val Glu Ala Gln Arg Lys Ala
545                 550                 555                 560

Leu Gln Ala Pro Ala Ser Ser Pro Ala Gly Trp Gln Thr Asn Ala Pro
                565                 570                 575

Leu Glu Ile Ala Val Asp Pro Ser Thr Arg Val His Ser Pro Ser Pro
                580                 585                 590

Pro Cys Ser Ser Ala Ala Phe Pro Ser Phe Leu Pro Asp Ser Ile Ser
                595                 600                 605

Ser Phe Ala Thr Lys Ser Glu Ser Leu Ser Leu His Lys Ile His Asn
                610                 615                 620

Pro Thr Leu Gln Arg Tyr Tyr Gln Leu Leu Val Tyr Arg His Tyr Asn
625                 630                 635                 640

Pro Ala Ser Pro Pro Val Ala Leu Gly Glu Gly Ser Glu Thr Gln
                645                 650                 655

Ala Gln Thr Thr Trp Arg Glu Ala Glu Glu Ser His Gln His Arg Leu
                660                 665                 670

His His Met Trp Ala Arg Gly Ser Pro Val Glu Arg Leu Phe Thr Val
                675                 680                 685

Arg Thr Pro Gly Cys Leu Asp Ser Glu Gln Pro Asp Ala Ser Val Glu
                690                 695                 700

Gln Thr Lys Glu Ala Gly Gln Arg Glu Thr Gln Val Asp Ala Ala Leu
705                 710                 715                 720

Lys Ala Ala Phe Pro Gln Ala Thr Ser Leu Glu Ala Gln Thr Ala Gly
                725                 730                 735

Arg Arg Gln Arg Glu Val Gln Gln Lys Leu Leu Phe Gly Glu Val Val
                740                 745                 750

Arg Lys Gln Lys Glu Leu Val Val Arg Asp Val Lys Val Ser Gly Glu
                755                 760                 765

Trp Thr Glu Pro His Phe Asp Thr Pro Gly Glu Glu Pro Arg Met Thr
770                 775                 780

Ala Glu Ala Arg Arg Glu Glu Thr Glu Lys Leu Glu Arg Ala Ile Glu
785                 790                 795                 800

Glu Glu Glu Arg Gln Lys Lys Leu Glu Ala Leu Lys Ala Leu His Val
                805                 810                 815

His Ser Val Asn Pro Val Arg Asp Phe Gln Arg Leu Leu Glu Val Lys
                820                 825                 830

Glu Thr Asp Leu Thr Glu Lys Ala Ile Gln Glu Met Thr Glu Met Ile
                835                 840                 845

Phe Lys Phe Leu Arg Ala Ala Gly Pro Pro Gln Gly Ala Leu Glu Arg
850                 855                 860

Pro Thr Gly Ala Gly Arg Gly Gly Glu Thr Ser Gly Leu Gln Asn Phe
865                 870                 875                 880

Arg Arg Gln Gln His Leu Gly Lys Ala Leu Val Cys Val Glu Ala Leu
                885                 890                 895

Arg Glu Gly Cys Arg Arg Glu Leu Glu Gly Glu Lys Phe Asn Glu Phe
                900                 905                 910

Leu Ala Glu Val Lys Ala Glu Gln Cys Arg Ala Asp Ala Ala Ala Asp
                915                 920                 925

Asp Ser Phe Arg Thr Phe Trp Asn Leu Leu Lys Ser Arg Lys Ile Gly
                930                 935                 940

Leu Ile Thr His Ala Glu Asp Pro Arg Val Asp Leu Glu Pro Ala Gln
945                 950                 955                 960

Ser Leu Arg Ile Tyr Glu Asp Glu Ser Val Gln Glu Leu Ser Thr Gln
```

```
                    965                 970                 975
Thr Ala Met Thr Ala Ala Arg Pro Leu Asp Pro His Asp Val Asp Asp
            980                 985                 990

Leu Leu Asp Leu Val Glu
        995

<210> SEQ ID NO 3
<211> LENGTH: 680
<212> TYPE: PRT
<213> ORGANISM: Arabidopsis thaliana

<400> SEQUENCE: 3

Met Ala Arg Asn Arg Glu Gly Leu Val Leu Val Leu Asp Val Gly Pro
1               5                   10                  15

Ala Met Arg Ser Val Leu Pro Asp Val Glu Lys Ala Cys Ser Met Leu
            20                  25                  30

Leu Gln Lys Lys Leu Ile Tyr Asn Lys Tyr Asp Glu Val Gly Ile Val
        35                  40                  45

Val Phe Gly Thr Glu Glu Thr Gly Asn Glu Leu Ala Arg Glu Ile Gly
    50                  55                  60

Gly Tyr Glu Asn Val Thr Val Leu Arg Asn Ile Arg Val Val Asp Glu
65                  70                  75                  80

Leu Ala Ala Glu His Val Lys Gln Leu Pro Arg Gly Thr Val Ala Gly
                85                  90                  95

Asp Phe Leu Asp Ala Leu Ile Val Gly Met Asp Met Leu Ile Lys Met
            100                 105                 110

Tyr Gly Asn Ala His Lys Gly Lys Lys Arg Met Cys Leu Ile Thr Asn
        115                 120                 125

Ala Ala Cys Pro Thr Lys Asp Pro Phe Glu Gly Thr Lys Asp Asp Gln
    130                 135                 140

Val Ser Thr Ile Ala Met Lys Met Ala Ala Glu Gly Ile Lys Met Glu
145                 150                 155                 160

Ser Ile Val Met Arg Ser Asn Leu Ser Gly Asp Ala His Glu Arg Val
                165                 170                 175

Ile Glu Glu Asn Asp His Leu Leu Thr Leu Phe Ser Ser Asn Ala Ile
            180                 185                 190

Ala Lys Thr Val Asn Val Asp Ser Pro Leu Ser Leu Leu Gly Ser Leu
        195                 200                 205

Lys Thr Arg Arg Val Ala Pro Val Thr Leu Phe Arg Gly Asp Leu Glu
    210                 215                 220

Ile Asn Pro Thr Met Lys Ile Lys Val Trp Val Tyr Lys Lys Val Ala
225                 230                 235                 240

Glu Glu Arg Leu Pro Thr Leu Lys Met Tyr Ser Asp Lys Ala Pro Pro
                245                 250                 255

Thr Asp Lys Phe Ala Lys His Glu Val Lys Val Asp Tyr Asp Tyr Lys
            260                 265                 270

Val Thr Ala Glu Ser Thr Glu Val Ile Ala Pro Glu Glu Arg Ile Lys
        275                 280                 285

Gly Phe Arg Tyr Gly Pro Gln Val Ile Pro Ile Ser Pro Asp Gln Ile
    290                 295                 300

Glu Thr Leu Lys Phe Lys Thr Asp Lys Gly Met Lys Leu Leu Gly Phe
305                 310                 315                 320

Thr Glu Ala Ser Asn Ile Leu Arg His Tyr Tyr Met Lys Asp Val Asn
                325                 330                 335
```

```
Ile Val Val Pro Asp Pro Ser Lys Glu Lys Ser Val Leu Ala Val Ser
            340                 345                 350

Ala Ile Ala Arg Glu Met Lys Glu Thr Asn Lys Val Ala Ile Val Arg
        355                 360                 365

Cys Val Trp Arg Asn Gly Gln Gly Asn Val Val Gly Val Leu Thr
370                 375                 380

Pro Asn Val Ser Glu Arg Asp Thr Pro Asp Ser Phe Tyr Phe Asn
385                 390                 395                 400

Val Leu Pro Phe Ala Glu Asp Val Arg Glu Phe Pro Phe Pro Ser Phe
                405                 410                 415

Asn Lys Leu Pro Ser Ser Trp Lys Pro Asp Gln Gln Gln Ala Val
                420                 425                 430

Ala Asp Asn Leu Val Lys Met Leu Asp Leu Ala Pro Ser Ala Glu Glu
            435                 440                 445

Glu Val Leu Lys Pro Asp Leu Thr Pro Asn Pro Val Leu Gln Arg Phe
450                 455                 460

Tyr Glu Tyr Leu Glu Leu Lys Ser Lys Ser Thr Asp Ala Thr Leu Pro
465                 470                 475                 480

Pro Met Asp Gly Thr Phe Lys Arg Leu Met Glu Gln Asp Pro Glu Leu
                485                 490                 495

Ser Ser Asn Asn Lys Ser Ile Met Asp Thr Phe Arg Gly Ser Phe Glu
            500                 505                 510

Val Lys Glu Asn Pro Lys Leu Lys Ala Ser Lys Arg Leu Leu Arg
            515                 520                 525

Asp Lys Pro Ser Gly Ser Asp Glu Asp Asn Arg Met Ile Thr Tyr
            530                 535                 540

Asp Ala Lys Glu Asn Lys Ile Asp Ile Val Gly Asp Ala Asn Pro Ile
545                 550                 555                 560

Gln Asp Phe Glu Ala Met Ile Ser Arg Arg Asp Lys Thr Asp Trp Thr
                565                 570                 575

Glu Lys Ala Ile Thr Gln Met Lys Asn Leu Ile Met Lys Leu Val Glu
                580                 585                 590

Asn Cys Thr Asp Glu Gly Asp Lys Ala Leu Glu Cys Val Leu Ala Leu
            595                 600                 605

Arg Lys Gly Cys Val Leu Glu Gln Pro Lys Gln Phe Asn Glu Phe
            610                 615                 620

Leu Asn His Leu Phe Lys Leu Cys Gln Glu Arg Asn Leu Ser His Leu
625                 630                 635                 640

Leu Glu His Phe Met Ser Lys Lys Ile Thr Leu Ile Pro Lys Ser Glu
                645                 650                 655

Ala Ala Asp Ser Asp Ile Val Asp Glu Asn Ala Gly Asp Phe Ile Val
                660                 665                 670

Lys Gln Glu Ser Met Leu Glu Ser
            675                 680

<210> SEQ ID NO 4
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 4
actagtggtg atgacgacga caagatgcct cacagtggag ggc                    43
```

```
<210> SEQ ID NO 5
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 5
gatatccacg tgtcgcggcc gcgctctc                                      28

<210> SEQ ID NO 6
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 6
gagagcgcgg ccgcgac                                                  17

<210> SEQ ID NO 7
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 7
cacgtggagg cgagacgtcg tcgtc                                         25

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
agtacttgat gaattcaccg                                               20

<210> SEQ ID NO 9
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 9
tttctgcgag atcttcttca cg                                            22

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
gcgtgaagaa gatctcgcag                                               20

<210> SEQ ID NO 11
<211> LENGTH: 35
<212> TYPE: DNA
<213> ORGANISM: Artificial sequence
<220> FEATURE:
<223> OTHER INFORMATION: Synthetic oligonucleotide
```

```
<400> SEQUENCE: 11
atcgatcacg tgatttttga ggccagtatt catcc                                    35

<210> SEQ ID NO 12
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 12
gctagcgtgg acccccatta tccttcgc                                            28

<210> SEQ ID NO 13
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 13
actagtcact cgtcgaatgg ttgcgtctg                                           29

<210> SEQ ID NO 14
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 14
gctagcgtgg acccccatta tccttcgc                                            28

<210> SEQ ID NO 15
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 15
actagtgaaa tcgcgatcaa cgcgacag                                            28

<210> SEQ ID NO 16
<211> LENGTH: 57
<212> TYPE: DNA
<213> ORGANISM: Artificial sequence
<220> FEATURE:
<223> OTHER INFORMATION: Synthetic oligonucleotide

<400> SEQUENCE: 16
agtacttgca ccaccaccac caccactaat ttccaatact ttcgccaaaa acgttcc            57

<210> SEQ ID NO 17
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 17
gcgcacgtgg ttgagagctt gacccgcatg ca                                       32

<210> SEQ ID NO 18
<211> LENGTH: 40
```

```
<212> TYPE: DNA
<213> ORGANISM: Artificial sequence
<220> FEATURE:
<223> OTHER INFORMATION: Synthetic oligonucleotide

<400> SEQUENCE: 18
cgctagatct aaaatgtcga ataacgcttt acaaacaatt                              40

<210> SEQ ID NO 19
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 19
cgctatgcat tcaacgtttg tagtcgatgg cttc                                    34

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
gtgaagacga cggctgagcg                                                    20

<210> SEQ ID NO 21
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 21
gtgaattcct caccggttga gacc                                               24

<210> SEQ ID NO 22
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 22
ggtctcaacc ggtgaggaat tcac                                               24

<210> SEQ ID NO 23
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 23
gcctcgagct atgacgtcga ttgctagcag tgc                                     33

<210> SEQ ID NO 24
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 24
```

```
gaagtacatt caggatcctg ggtca                                            25
```

<210> SEQ ID NO 25
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 25

```
cctgaggata tcccagctgt acg                                              23
```

<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 26

```
gaagcgcgac aagcttcgct g                                                21
```

<210> SEQ ID NO 27
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 27

```
cagcgaagct tgtcgcgctt c                                                21
```

<210> SEQ ID NO 28
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 28

```
gctctagaca gttgttcatg cagcttcaca aggt                                  34
```

<210> SEQ ID NO 29
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 29

```
ggagctcgag catatcttct gcca                                             24
```

<210> SEQ ID NO 30
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 30

```
ccgtttaaac tttgattgtg cgtccacagg taca                                  34
```

<210> SEQ ID NO 31
<211> LENGTH: 38
<212> TYPE: DNA
<213> ORGANISM: Artificial Sequence

```
<220> FEATURE:
<223> OTHER INFORMATION: Synthetic oligonucleotide

<400> SEQUENCE: 31
gcgctagcgg taccgagagc cagtagtgac agaacggt                              38

<210> SEQ ID NO 32
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 32
gcgctagctc tagaagatct tttcatgtat cggggact                              38

<210> SEQ ID NO 33
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 33
gccacgtgaa ggagttacca cccatgacga gc                                    32

<210> SEQ ID NO 34
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 34
gtttaaacga taagcttgat cagcacgaaa ccttg                                 35

<210> SEQ ID NO 35
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 35
gtttaaaccc gctctagaac tagtggatcc c                                     31

<210> SEQ ID NO 36
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 36
gtcgacaccg gtttcaccct ca                                               22

<210> SEQ ID NO 37
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 37
gtcgacgcaa aaatggaagt accgg                                            25
```

<210> SEQ ID NO 38
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 38
gcagtacttg tcaatctttc gcgacaagca c                              31

<210> SEQ ID NO 39
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 39
gcgatatccg tattctggaa agatttccgg tg                             32

<210> SEQ ID NO 40
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 40
gcagtactat gtccgcctga agtcctacc                                 29

<210> SEQ ID NO 41
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 41
ggcacgtgat cggtattctc ctagacggc                                 29

<210> SEQ ID NO 42
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 42
gcagtactat gtgcattcgc gacatttgga ag                             32

<210> SEQ ID NO 43
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 43
ggcacgtgtc aaatgaatag gcgggagtgg                                30

<210> SEQ ID NO 44
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 44
gcagtactta cttcggcgag gagttgcac                                29

<210> SEQ ID NO 45
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 45
ggcacgtggg aagacggtaa ccacagtg                                 28

<210> SEQ ID NO 46
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 46
gcagtacttg aacggctatt gccgcct                                  27

<210> SEQ ID NO 47
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 47
ggcacgtgtc gcctcttgct ctgcc                                    25

<210> SEQ ID NO 48
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 48
aaaccagtac atcgttaact tctgtcgt                                 28

<210> SEQ ID NO 49
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 49
gatgattttc tgacttggga gcaactg                                  27

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
ggaactgcat ccgttccatg                                          20

<210> SEQ ID NO 51

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
tctttaaagc gttcgtggtc                                              20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
ggcacaaaca acttggaggg                                              20

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 53
ttcagagcgg catcaacctg                                              20

<210> SEQ ID NO 54
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 54
acgtctgtac gcgtaccgat acg                                          23

<210> SEQ ID NO 55
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 55
gcgacaagct tcgctggata gc                                           22

<210> SEQ ID NO 56
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 56
ttccagcttt gcgacgaagt cg                                           22

<210> SEQ ID NO 57
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 57
```
cttccagcga cgttgcctga g                                    21

<210> SEQ ID NO 58
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 58
gagagggctg gtcggaaagt c                                    21

<210> SEQ ID NO 59
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 59
atctgccgat cgtacaatca gtga                                 24

<210> SEQ ID NO 60
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 60
ctgggcaaag cttcaagcga gtg                                  23

<210> SEQ ID NO 61
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 61
gacaagtccg tcaatggcgt cac                                  23

<210> SEQ ID NO 62
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 62
cgcgagaccc ttagatccgc a                                    21

<210> SEQ ID NO 63
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 63
tgcgcagtgc tacactaact gg                                   22

<210> SEQ ID NO 64
<211> LENGTH: 26
<212> TYPE: DNA

```
<213> ORGANISM: Artificial Sequence
<220> FEATURE:
<223> OTHER INFORMATION: Synthetic oligonucleotide

<400> SEQUENCE: 64
cgtctggatc gttggttgct gctacg                                    26

<210> SEQ ID NO 65
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 65
accacttctc gtactatggc cggtcga                                   27

<210> SEQ ID NO 66
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 66
ccacgattta cgtcctgtag ctgc                                      24

<210> SEQ ID NO 67
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 67
gtgaatacgg cgtggagtcg ctgca                                     25

<210> SEQ ID NO 68
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 68
cagcaagcgg aacaggcgtg aggt                                      24

<210> SEQ ID NO 69
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 69
gggcatgcct tatgccgtga ccga                                      24

<210> SEQ ID NO 70
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 70
cgcagccagc atagccaggt cca                                       23
```

<210> SEQ ID NO 71
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 71
tgacgtcggg tgcctacgtt c                                           21

<210> SEQ ID NO 72
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 72
cgacagctgc actcgaagac ac                                          22

<210> SEQ ID NO 73
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 73
ccgtttaaac tttgattgtg cgtccacagg taca                             34

<210> SEQ ID NO 74
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 74
gcgcagttga caaattgtct gagg                                        24

<210> SEQ ID NO 75
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 75
gttggcctac gtgacttgct gatg                                        24

<210> SEQ ID NO 76
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 76
acaaacgcac cacatgcgtt ctg                                         23

<210> SEQ ID NO 77
<211> LENGTH: 19
<212> TYPE: DNA
<213> ORGANISM: Artificial Sequence
<220> FEATURE:

```
<223> OTHER INFORMATION: Synthetic oligonucleotide

<400> SEQUENCE: 77
gcggaggcct tgaggctga                                                   19

<210> SEQ ID NO 78
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 78
actgcgaaca gcagcaagat cg                                               22

<210> SEQ ID NO 79
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 79
ggtgggagca gcaaagacag ct                                               22

<210> SEQ ID NO 80
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 80
ggtcttcaac agcgcgcagt c                                                21

<210> SEQ ID NO 81
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 81
cactgtaagc gtgtgcggta cg                                               22

<210> SEQ ID NO 82
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 82
gctggattac gtcgtcacca agg                                              23

<210> SEQ ID NO 83
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 83
ccagattcga ttcggtgacg gac                                              23
```

```
<210> SEQ ID NO 84
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 84
ccggtgaaat tcgtcaagga gcc                                               23

<210> SEQ ID NO 85
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 85
aacaccagca ttgcaggtct cag                                               23

<210> SEQ ID NO 86
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 86
agtgctccta cgggcgttca tga                                               23
```